United States Patent
Halevy et al.

(10) Patent No.: US 11,794,073 B2
(45) Date of Patent: Oct. 24, 2023

(54) SYSTEM AND METHOD FOR GENERATING MOVEMENT BASED INSTRUCTION

(71) Applicant: Altis Movement Technologies, Inc., Fort Lauderdale, FL (US)

(72) Inventors: Jeff Halevy, Fort Lauderdale, FL (US); Constantine Goltsev, Kyiv (UA); Oleksii A. Bulgakov, Staten Island, NY (US); Aleksandr V. Tselousov, Kovrov (RU); Fedor G. Savchenko, Krasnador (RU)

(73) Assignee: Altis Movement Technologies, Inc., Fort Lauderdale, FL (US)

( * ) Notice: Subject to any disclaimer, the term of this patent is extended or adjusted under 35 U.S.C. 154(b) by 0 days.

(21) Appl. No.: 17/592,444

(22) Filed: Feb. 3, 2022

(65) Prior Publication Data

US 2022/0241642 A1 Aug. 4, 2022

Related U.S. Application Data

(63) Continuation-in-part of application No. 17/538,631, filed on Nov. 30, 2021.
(Continued)

(51) Int. Cl.
*A63B 24/00* (2006.01)
*A63B 71/06* (2006.01)

(52) U.S. Cl.
CPC ...... *A63B 24/0006* (2013.01); *A63B 24/0062* (2013.01); *A63B 71/0622* (2013.01);
(Continued)

(58) Field of Classification Search
CPC ............ A63B 24/0006; A63B 24/0062; A63B 71/0622; A63B 71/0669; A63B 2024/0009; A63B 2024/0015; A63B 2024/0065; A63B 2071/0636; A63B 2071/0647; A63B 2220/17; A63B 2220/807

See application file for complete search history.

(56) References Cited

U.S. PATENT DOCUMENTS 8,918,162 B2 12/2014 Prokoski
9,011,293 B2 4/2015 Shavit et al.
(Continued)

FOREIGN PATENT DOCUMENTS

| KR | 20190055434 A | 5/2019 |
| WO | 2020023421 A1 | 1/2020 |
| WO | 2020144175 A1 | 7/2020 |

OTHER PUBLICATIONS

Dickey, M.R., "Tonal Launches At-Home Digital Strength-Training System," as accessed Jan. 7, 2021, at https://techcrunch.com/2018/08/16/tonal-launches-at-home-digital-strength-training-system/?ncid=txtlnkusaolp00000616, 10 pages.
(Continued)

*Primary Examiner* — Xin Sheng
(74) *Attorney, Agent, or Firm* — Alliance IP, LLC

(57) ABSTRACT

A method, comprising providing playback of one or more sets of three dimensional positional data of a subject performing an activity; detecting input from an editor respective to the playback of the one or more sets of three dimensional positional data; and storing parameters of the activity based on the detected input in an activity profile for use in movement based instruction.

19 Claims, 26 Drawing Sheets

Related U.S. Application Data

(60) Provisional application No. 63/168,790, filed on Mar. 31, 2021, provisional application No. 63/145,244, filed on Feb. 3, 2021.

(52) U.S. Cl.
CPC .. *A63B 71/0669* (2013.01); *A63B 2024/0009* (2013.01); *A63B 2024/0015* (2013.01); *A63B 2024/0065* (2013.01); *A63B 2071/0636* (2013.01); *A63B 2071/0647* (2013.01); *A63B 2220/17* (2013.01); *A63B 2220/807* (2013.01)

(56) References Cited

U.S. PATENT DOCUMENTS

| | | |
|---|---|---|
| 9,865,176 B2 | 1/2018 | Tran |
| 10,529,137 B1 | 1/2020 | Black et al. |
| 10,540,483 B2 | 1/2020 | Hardee et al. |
| 10,661,112 B2 | 5/2020 | Orady et al. |
| 10,799,760 B2 | 10/2020 | Canavan et al. |
| 2013/0324857 A1 | 12/2013 | Kurillo et al. |
| 2014/0228985 A1 | 8/2014 | Elliott et al. |
| 2015/0269860 A1* | 9/2015 | Shaw ............... G09B 9/08 434/30 |
| 2016/0081594 A1 | 3/2016 | Gaddipati et al. |
| 2016/0235323 A1 | 8/2016 | Tadi et al. |
| 2017/0039480 A1 | 2/2017 | Bitran et al. |
| 2017/0136296 A1 | 5/2017 | Barrera et al. |
| 2017/0368413 A1 | 12/2017 | Shavit |
| 2018/0184947 A1 | 7/2018 | Richards et al. |
| 2018/0374383 A1 | 12/2018 | Thielen et al. |
| 2020/0126284 A1* | 4/2020 | Garofalo ............ G16H 40/67 |
| 2020/0160044 A1 | 5/2020 | Sur et al. |
| 2020/0222757 A1 | 7/2020 | Yang et al. |
| 2020/0353314 A1 | 11/2020 | Messinger |
| 2020/0372245 A1 | 11/2020 | Juhas et al. |

OTHER PUBLICATIONS

Rehouma, H. et al., "Advancements in Methods and Camera-Based Sensors for the Quantification of Respiration," MDPI Sensors Journal, Dec. 2020; 55 pages.

PCT International Search Report and Written Opinion issued in PCT/US2022/015154, dated Jul. 14, 2022; 22 pages.

* cited by examiner

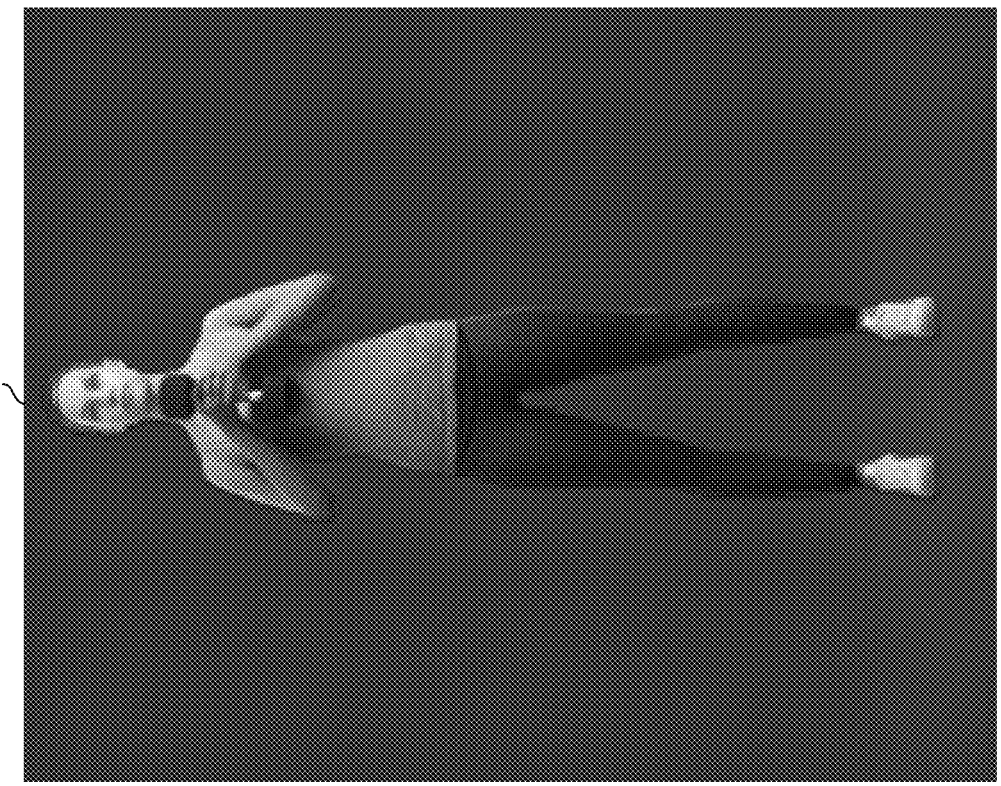
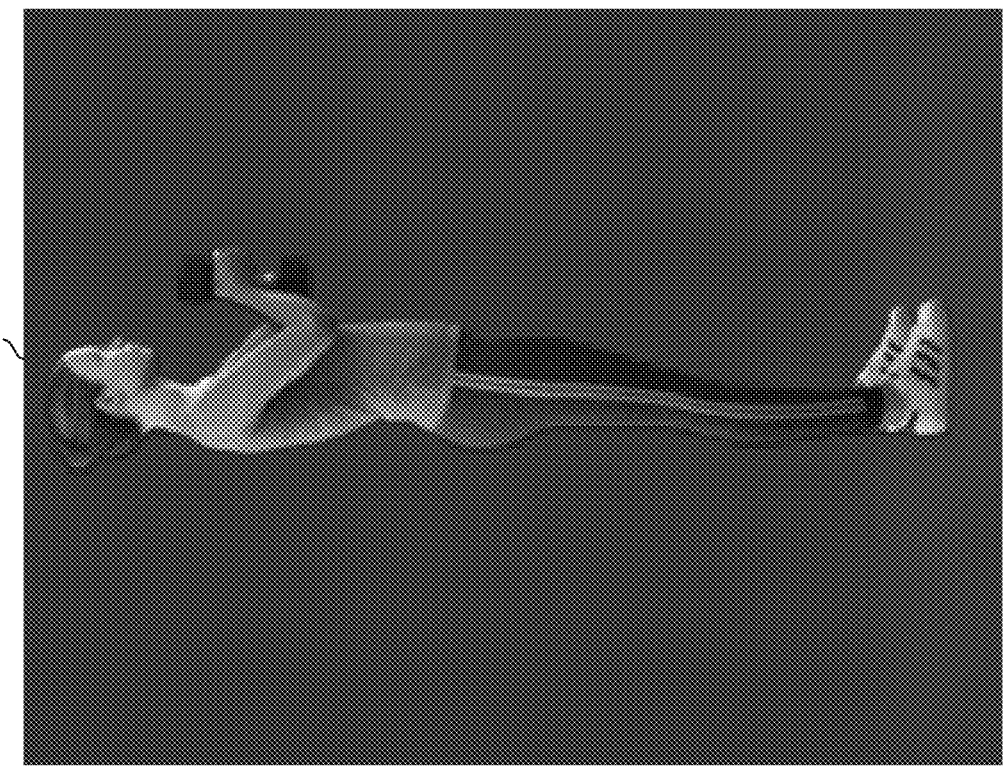
FIG 2B

PASSIVE STEREO

ACTIVE STEREO

STRUCTURED LIGHT

TIME OF FLIGHT

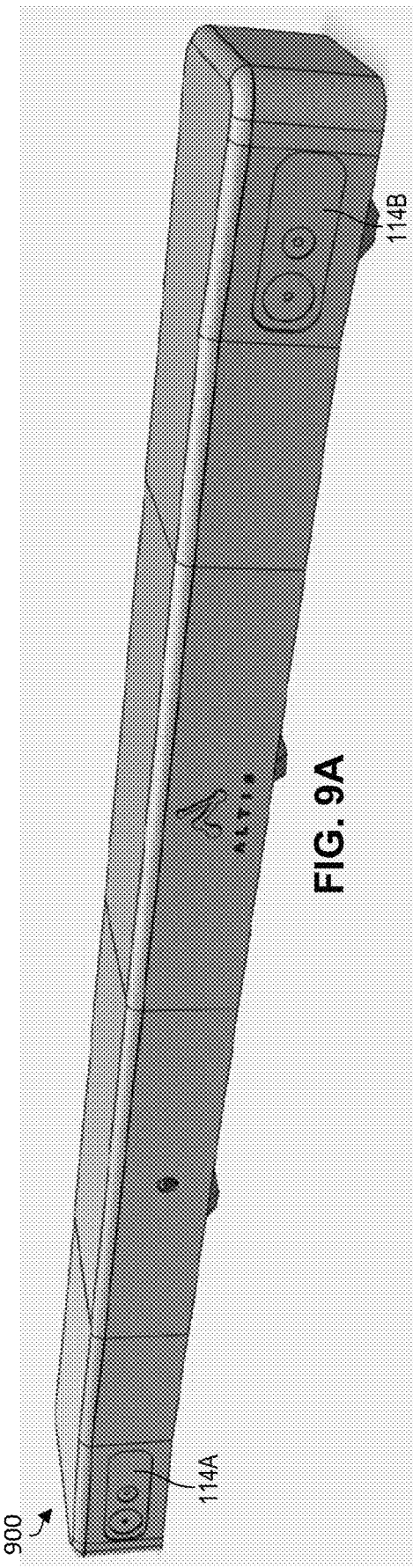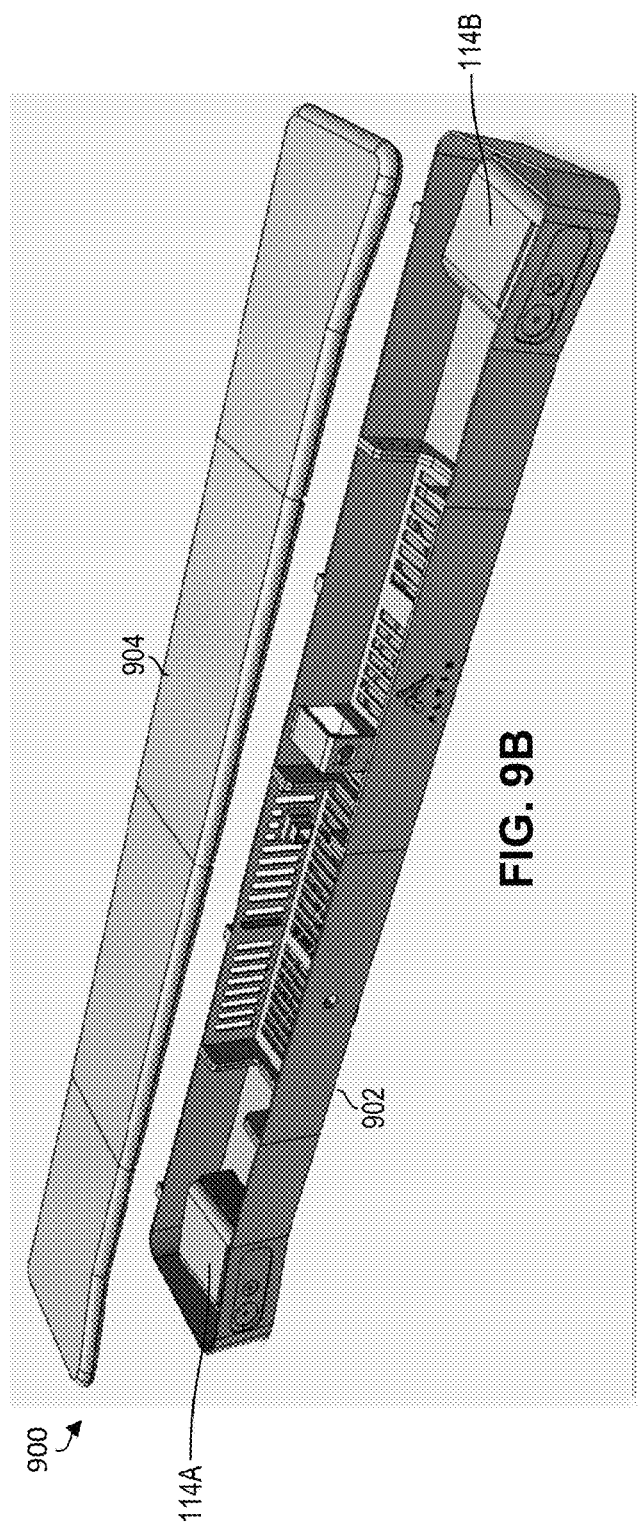

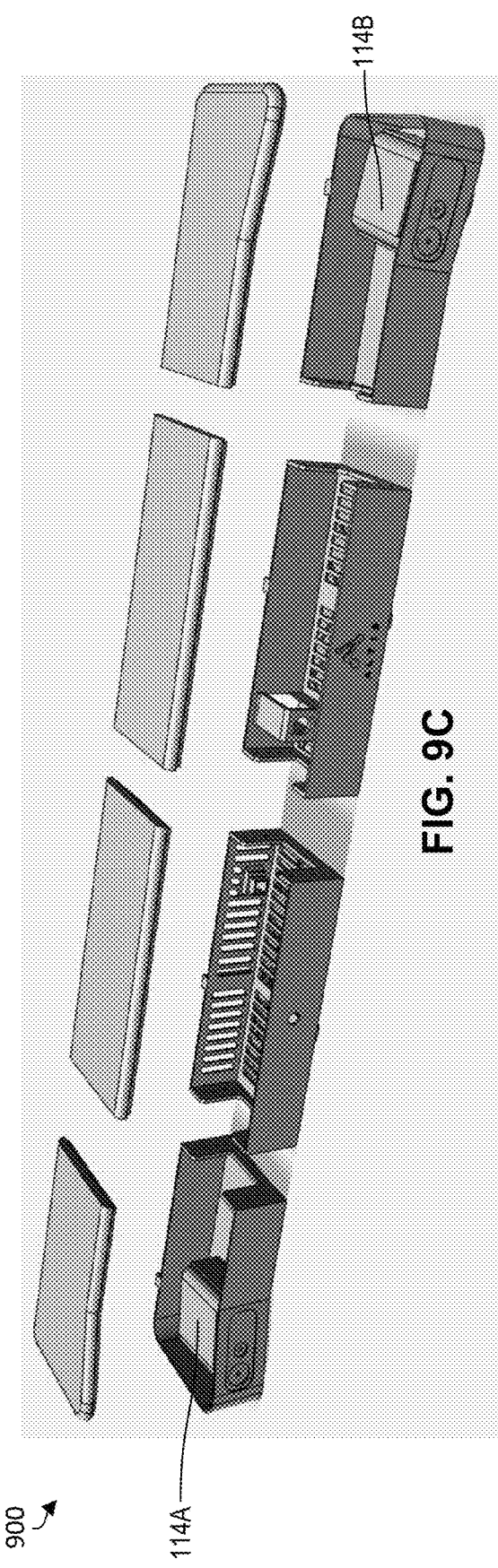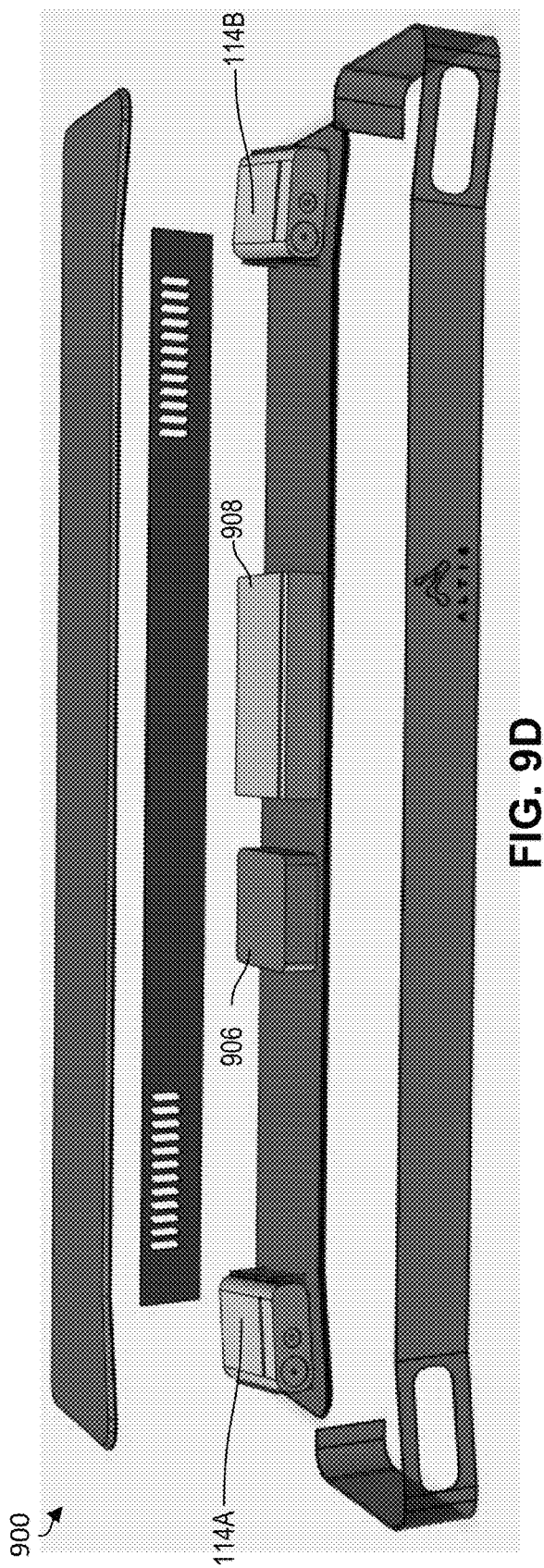

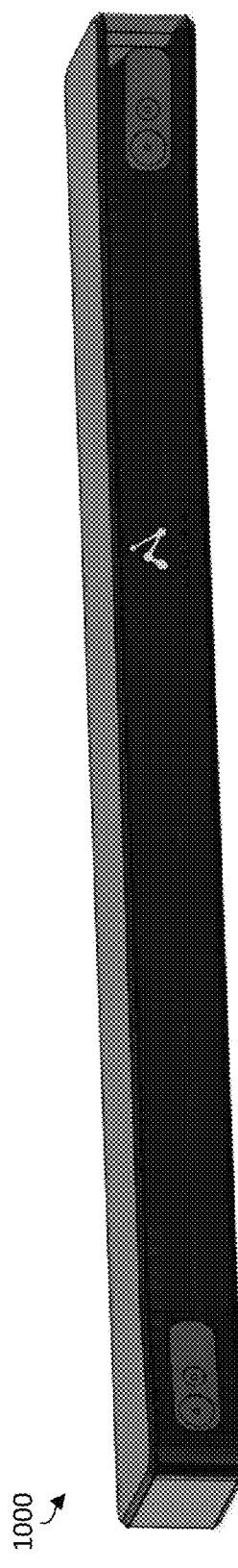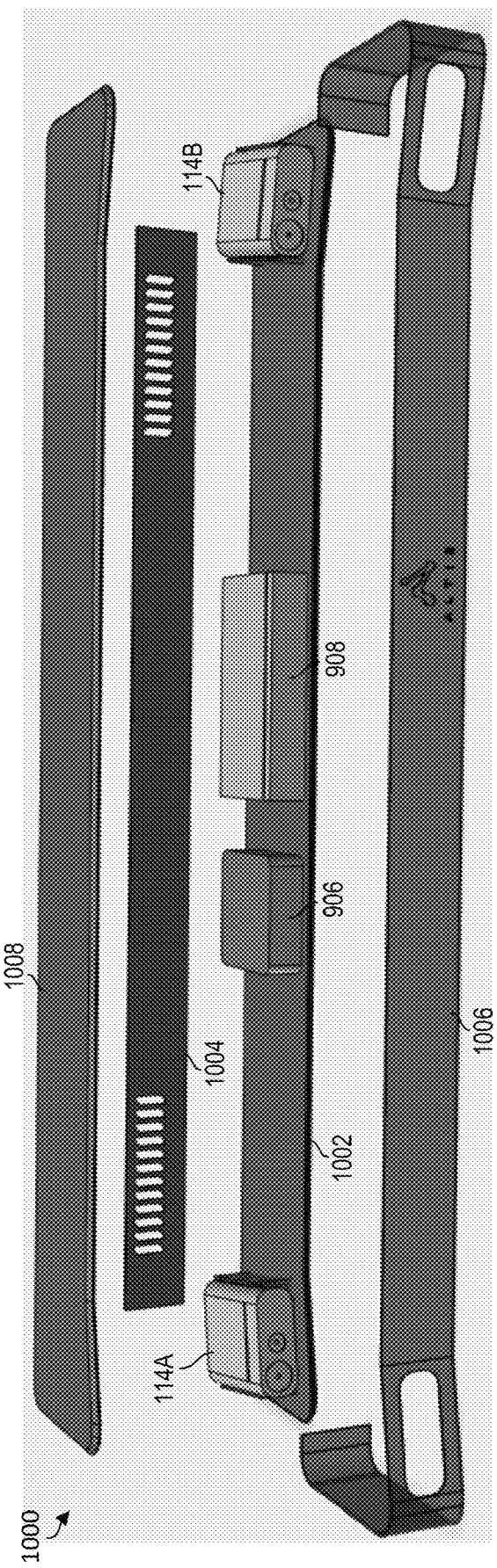
FIG. 10A
FIG. 10B

SYSTEM AND METHOD FOR GENERATING MOVEMENT BASED INSTRUCTION

RELATED APPLICATIONS

This application is a continuation-in-part of U.S. patent application Ser. No. 17/538,631, filed Nov. 30, 2021 and titled "SYSTEM AND METHOD FOR PROVIDING MOVEMENT BASED INSTRUCTION", which claims the benefit of priority to U.S. Provisional Patent Application Ser. No. 63/145,244, filed Feb. 3, 2021 and titled "SYSTEM AND METHOD FOR GENERATING MOVEMENT BASED INSTRUCTION", and U.S. Provisional Patent Application Ser. No. 63/168,790, filed Mar. 31, 2021 and titled "SYSTEM AND METHOD FOR GENERATING MOVEMENT BASED INSTRUCTION". The disclosures of these prior Applications are considered part of and are incorporated by reference in the disclosure of this Application.

BACKGROUND

Motion capture devices comprise image sensors that capture positional data within the view of the image sensors. Image data is processed to provide novel systems and methods for movement based instruction as described herein.

BRIEF DESCRIPTION OF THE DRAWINGS

FIG. 2B illustrates a representation of a user from multiple points of view in accordance with certain embodiments.

FIGS. 9A-9D illustrate various views of a computing device incorporating various components of a motion capture and feedback system in accordance with certain embodiments.

FIGS. 10A-10B illustrate various views of another computing device incorporating various components of a motion capture and feedback system in accordance with certain embodiments.

DETAILED DESCRIPTION

Figure 1:
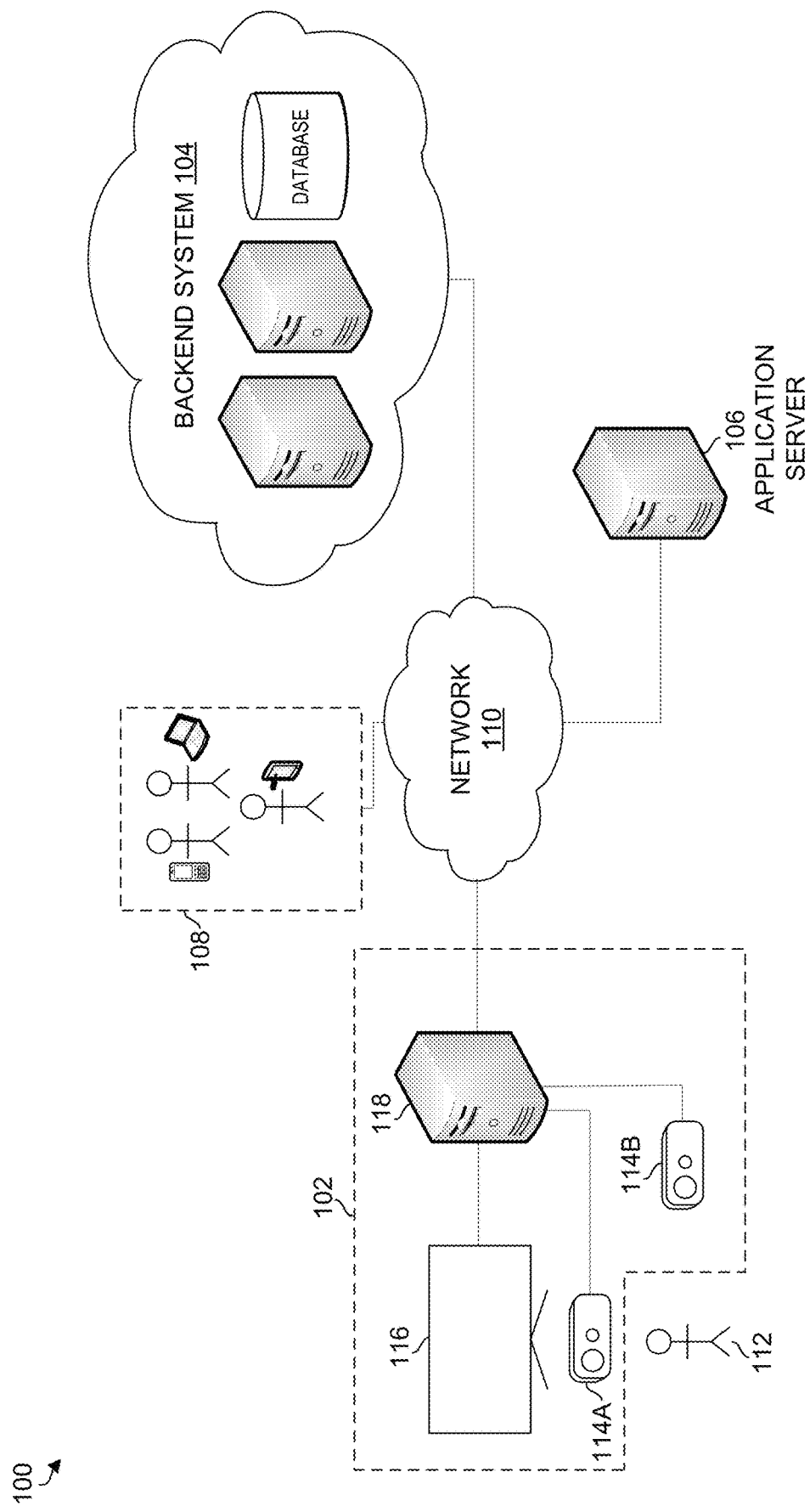
FIG. 1 illustrates a system to provide movement based instruction to a user in accordance with certain embodiments.

FIG. 1 illustrates a system 100 to provide movement based instruction to a user 112 in accordance with certain embodiments. System 100 includes a motion capture and feedback system 102, backend system 104, application server 106, and expert network system 108 coupled together through network 110. The system 102 includes motion capture devices 114 (e.g., 114A and 114B), display 116, and computing device 118. Other embodiments of system 100 may include other suitable components or may omit one or more of the depicted components.

Many individuals find fulfillment and/or enjoyment in movement based activities such as physical fitness exercises like calisthenics, plyometrics, weightlifting, and the like, as well as sports activities (such as pitching or hitting a baseball, dribbling or shooting a basketball, swinging a golf club, and the like), dance, and the like, as a means to reduce stress, increase muscle mass, improve bone strength, increase overall fitness, and to otherwise enhance quality of life. However, learning new movements and correctly performing these movements may be difficult, particularly for a beginner. In many instances, movement based activities may be difficult to optimally or safely perform without specialized training. A typical way to obtain this specialized training is through an in-person lesson with a personal trainer, coach, or other instructor. However, such training is subject to availability of a suitable instructor and may be cost prohibitive, depending on the trainee's situation and the duration of the training. Moreover, the quality of such instruction is highly variable as it is dependent on the ability, knowledge, and temperament of the instructor. Indeed, finding a properly qualified and reasonably priced instructor who has a schedule that aligns with an individual may be difficult or impracticable in many situations. One could alternatively seek to self-train by learning about a movement through print or video instruction and then attempting to implement the instruction. However, it may be difficult, time consuming, and/or potentially dangerous to learn and improve movements in this manner without real time feedback on proper performance of the movement.

In various embodiments of the present disclosure, system 100 may function as a computer-based, or artificially intelligent, personal trainer. System 100 may provide general instruction regarding movement based activities and may utilize motion capture devices 114 to record the movement of a user 112 performing an activity in order to provide personalized feedback to the user in real time. In various embodiments, the system 100 may provide information to correct the movement form of the user to promote health, safety, and optimal results. In some embodiments, the movement of a user may be mapped into a three-dimensional space and compared to a model movement form in the three-dimensional space in order to generate personalized instruction for the user 112. In various embodiments, system 100 may utilize multiple motion capture devices 114 in order to enable display of the user from a point of view that is adapted to the particular corrective instruction (e.g., based on the movement errors committed), enabling the user to quickly visualize and improve movement form. Thus, various embodiments may provide one or more advantages over other methods of movement instruction, such as improved instruction quality utilizing artificial intelligence (AI) techniques to provide hyper-personalized expert instruction, on-demand training, cost effective instruction, or real-time feedback.

Various embodiments of the present disclosure include a system 100 providing an intelligent personal trainer to provide instruction and real-time feedback for movement activities. The system 100 includes a motion capture and feedback system 102 operable to track the motion of a user 112 performing a movement activity, analyze the motion with respect to model movement patterns, and provide real-time feedback and encouragement to the user 112 to promote healthy and optimal movement patterns.

In operation, the system 100 may display (e.g., via display 116) a demonstration of an example movement pattern (e.g., a video or other visual representation) for a movement activity to be performed by the user 112. After viewing the demonstration (or independent of the demonstration), the user 112 may perform one or more repetitions of the movement activity. The system 100 may utilize a mapping of a movement activity in a three dimensional (3D) space and compare it against the movement pattern of the user during these repetitions. The system 100 may then provide real-time feedback to the user, including confirmation that the movement activity was performed correctly or specific instruction as to how to improve the movement pattern. When providing feedback, the system 100 may display (e.g., via display 116) the feedback from an optimal point of view that is selected by the system 100 based on the feedback being provided, allowing the user to clearly discern the portion of the user's movement that should be improved. In various embodiments, the system 100 may be capable of displaying any arbitrary point of view around the user as the optimal view to provide feedback, thus the user need not rotate his or her body in order to see a portion of the body that is the subject of the feedback (as would be required if a user were looking at a mirror for visual feedback). For example, the user may maintain a single orientation, while different feedback provided by the system 100 may display the user from the front, side, back, or other suitable point of view with accompanying corrective feedback.

In this manner, system 100 may function as an on-demand expert personal trainer, teaching the user 112 new movement activities and aiding the user in performing movement activities in a safe and effective manner, while lowering the cost and increasing the convenience of a workout session with expert instruction. The system 100 may provide the personal training functionality described herein for any number of users 112. For example, the system 100 may be used privately in a home gym, publicly in a commercial gym, or in any other suitable setting.

While this disclosure will focus on application of the system 102 to movement activities such as weightlifting exercises, the system 100 may be configured to provide instruction for any suitable movement activities, such as plyometrics (e.g., a box jump, a broad jump, a lunge jump, etc.), dancing, running, playing musical instruments, or sport-specific athletic movements such as pitching or hitting a baseball, dribbling or shooting a basketball, throwing a football, swinging a golf club, spiking a volleyball, and the like.

Various embodiments of the present disclosure further provide an editor system to generate movement based instruction programs based on motion data, which may be used to instruct end users using a motion capture and feedback system. For example, a subject performing one or more activities may be recorded and the captured data (or data processed therefrom) may be provided to the editor system. An editor utilizing the editor system may review visual representations (e.g., based on the captured data) of the subject performing the activities and may configure parameters in association with the visual representations to generate activity profiles. These activity profiles may then be used, e.g., by any number of motion capture and feedback systems to provide feedback based on the motion of users performing the same activities (e.g., by counting repetitions performed, judging the quality of movements of the users, showing the users and/or a trainer from an optimal viewpoint when suboptimal movement is detected, or providing corrective prompts).

Various embodiments of the present disclosure further provide velocity based dynamic workout adjustments (e.g., via system 100 or other logic). The human central nervous system output is affected significantly by readiness, where readiness may be based on numerous physical and psychological factors such as sleep and stress. Velocity measurements of a user performing an activity may indicate the readiness of a user and may be used to determine (1) how much of an exercise an individual should perform (e.g., the number of sets and repetitions) and (2) the weight (also referred to as load) used during a specific exercise. Velocity measurements may also be used to modulate, in real time, one or both of the volume (sets×repetitions) and load (e.g., weight) in an exercise training session.

Further embodiments of the present disclosure may provide a system to generate customized workout plans for users based on parameters of a profile of a user, such as a fitness goal, workout history, physical attributes, availability, or other suitable parameters. In some embodiments, the system may utilize machine learning based on data associated with one or more other users to predict the activities and/or parameters associated with activities for the user.

In system 100 of FIG. 1, motion capture devices 114A and 114B may capture multiple images (e.g., 2D or 3D images) of the user 112 over a time period to produce a video stream (e.g., a temporally ordered sequence of 2D or 3D images). In order to capture the images, a motion capture device 114 may include one or more image sensors, e.g., light detection and ranging (LIDAR) sensors, two-dimensional (2D) cameras (e.g., RGB cameras), ultrasonic sensors, radars, or three-dimensional (3D) or stereo cameras (e.g., depth sensors, infrared illuminated stereo cameras, etc.).

Figure 8A:
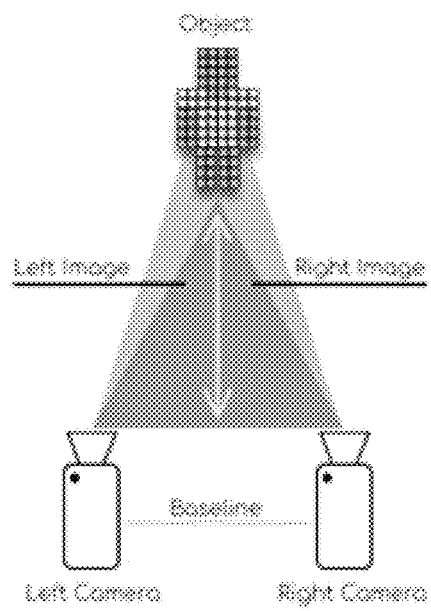
FIGS. 8A-8D illustrate example configurations utilizing various motion capture techniques in accordance with certain embodiments.
Figure 8B:
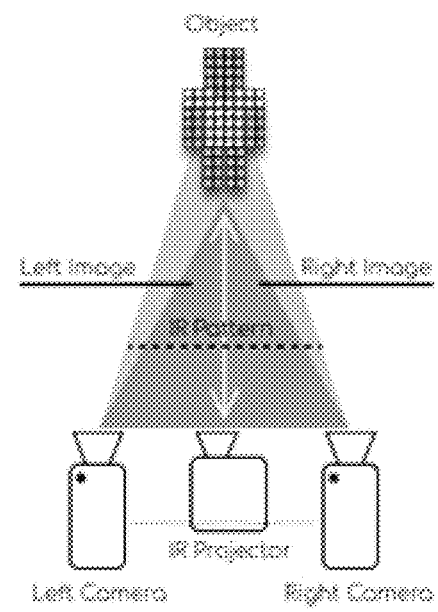
Figure 8C:
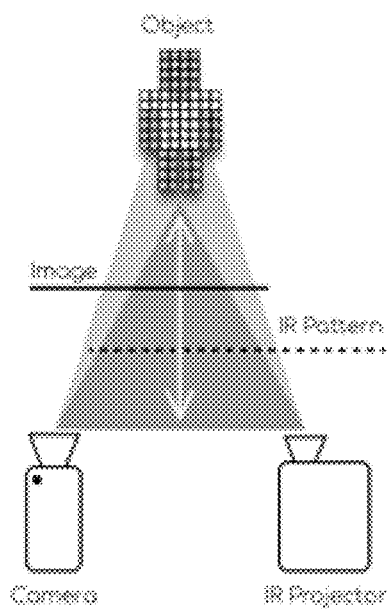
Figure 8D:
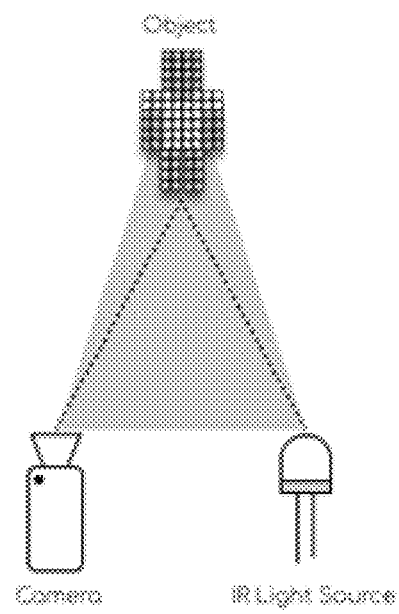

In various embodiments, the motion capture devices 114 of system 100 may utilize one or more of passive stereo, active stereo, structured light, or time of flight image acquisition techniques (if more than one technique is used, the acquired images may be fused together). FIGS. 8A-8D illustrate example configurations utilizing such techniques. FIG. 8A illustrates a passive stereo configuration and FIG. 8B illustrates an active stereo configuration. In both configurations, two cameras (depicted as a right camera and a left camera) capture slightly different images which may be used to generate a depth map. In a passive stereo configuration, an active light source is not used, while in an active stereo configuration, an active light source (e.g., a projector) is employed. FIG. 8C illustrates a structured light configuration in which a modulated light pattern is transmitted (e.g., by a projector) to the surface of a scene and an observed light pattern deformed by the surface of the scene is compared with the transmitted pattern and the image is obtained based on the disparity determined by the comparison. Although a single camera is depicted in FIG. 8C, in other structured light configurations, multiple (e.g., at least two) cameras may be used. FIG. 8D illustrates a time of flight configuration. In this configuration, the distance between the camera and an object is calculated by measuring the time it takes a projected light to travel from the infrared light source emitter, bounce off the object surface, and return to the camera receiver (based on the phase shift of the emitted and returned light). The object may then be reconstructed in an image based on such measurements.

Returning to FIG. 1, in various embodiments, a motion capture device 114 may include more than one image sensor. For example, a motion capture device 114 comprising a stereo camera may include two RGB cameras to capture 2D images. As another example, a motion capture device 114 may comprise two calibrated RGB cameras with a random infrared pattern illuminator. As another example, a motion capture device 114 may include a depth sensor as well as an RGB camera. In various embodiments, when multiple motion capture devices 114A and 114B are used, the sensors of the motion capture devices may be of the same type (e.g., the same one or more image sensors are resident on each motion capture device 114) or of different types (e.g., 114A may include an RGB camera and 114B may include a LIDAR sensor).

In the embodiment depicted, two discrete motion capture devices 114 (114A and 114B) are shown as being located in different positions so as to capture the user 112 at multiple different angles (whereas multiple image sensors on the same motion capture device 114 would capture the subject from substantially the same angle unless the motion capture device 114 is relatively large). In other embodiments, one or more additional motion capture devices 114 may be employed. In general, motion capture and feedback system 102 includes any suitable number and types of motion capture devices placed at different poses relative to the user 112 to enable capture of sufficient data to allow position determination of a group of body parts (which in some embodiments may be arranged into a skeleton) of the user 112 in 3D space, where a pose refers to the position and orientation of a motion capture device with respect to a reference coordinate system. For example, in the embodiment depicted, a motion capture device 114A is placed directly in front of the user 112 and a second motion capture device 114B is placed to the side of the user 112 (such that the angle formed between the first device, the user 112, and the second device is roughly 90 degrees in a horizontal plane). As another example, two motion capture devices may be placed at least a threshold distance apart (e.g., 5 feet) and may each be oriented towards the subject (e.g., one at a 45 degree angle and one at a −45 degree angle in a horizontal plane with respect to the user 112). As another example, two motion capture devices may be placed about 50 inches apart and each motion capture device may be angled inwards (e.g., towards the subject) by roughly 10 degrees. As another example, four motion capture devices may be placed as vertexes of a square and may be oriented towards the center of the square (e.g., where the user 112 is located). In various embodiments, the motion capture devices 114 or image sensors thereof may be placed at the same height or at different heights. FIGS. 9A-9D and 10 (to be discussed in further detail below) illustrate example configurations of motion capture devices 114. In some embodiments, multiple image sensors (e.g., cameras) may be placed at substantially the same horizontal position while each camera has its own vertical inclination. In some embodiments, a mechanism such as a scissor lift mechanism may be used to incline an apparatus containing one or more image sensors.

In various embodiments, each motion capture device 114 may be discrete from each other motion capture device 114. For example, a motion capture device 114 may have its own housing, power supply, or its own connection (e.g., wired or wireless) to the computing device 118 to send data captured by its image sensor(s) (or data processed therefrom) to the computing device 118 (or other computing device performing operations for the system 102).

In some embodiments, the user 112 may wear special clothing or other wearable devices and locations of these wearable devices may be tracked by system 102 in order to capture the position of various segments (e.g., body parts) of user 112. In some embodiments, the wearable devices may be used to estimate the 3D positions of various segments of user 112 to supplement data captured by one or more motion capture devices 114 in order to improve the accuracy of the position estimation. In yet other embodiments, the wearable devices may be used to estimate the 3D positions of the segments of user 112 without the use of passive sensors such as cameras.

Figure 11:
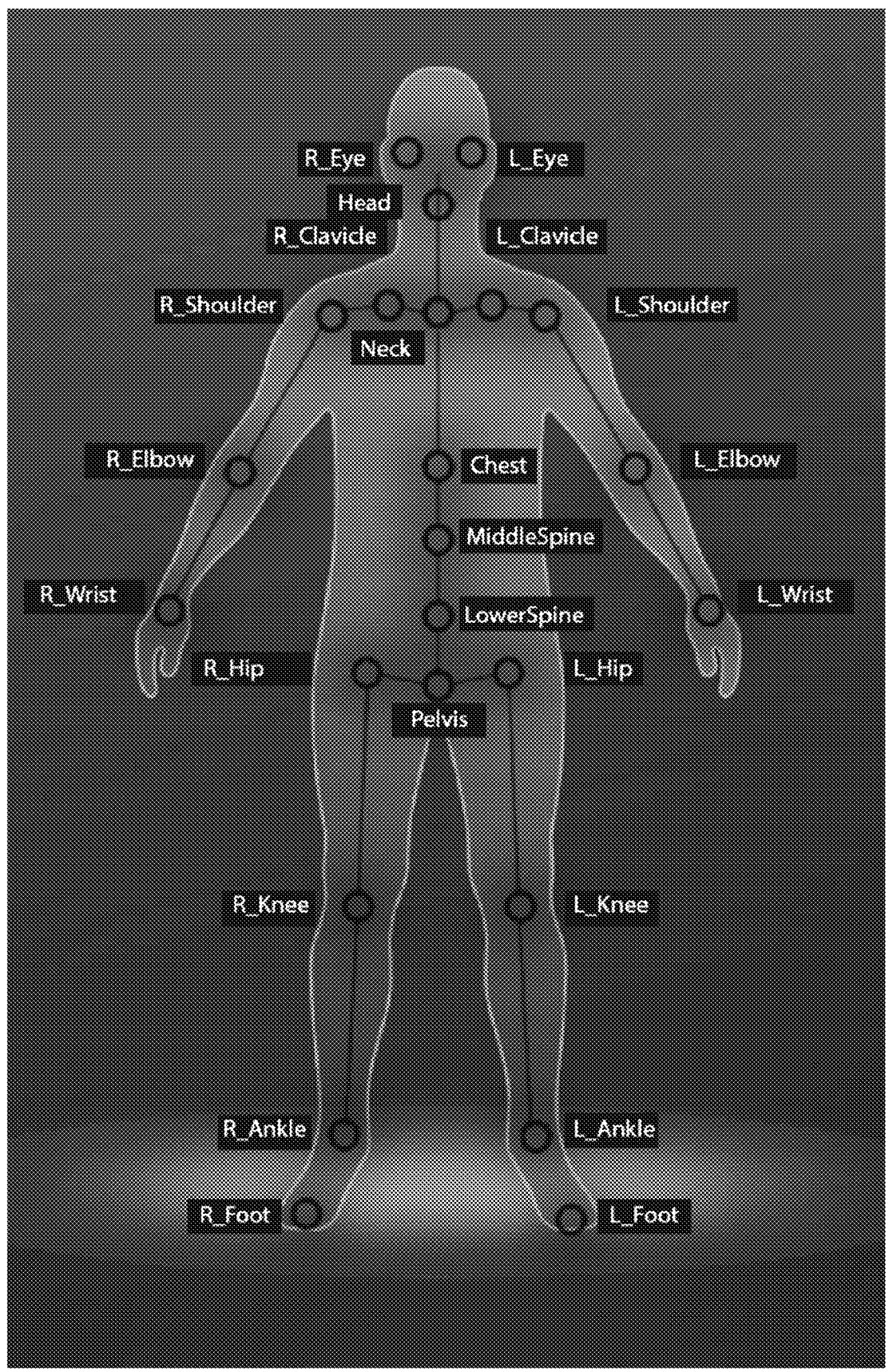
FIG. 11 illustrates example segments of a body in accordance with certain embodiments.

Motion capture and feedback system 102 (either by itself or in conjunction with one or more other devices of system 100) may track the movement of the user 112 by obtaining data from motion capture devices 114 and/or wearable devices and transforming or translating the captured data into representations of three dimensional (3D) positions of one or more segments (e.g., body parts) of the user 112. For example, as illustrated in FIG. 11, such segments may include one or more of a head, right and left eyes, right and left clavicles, right and left shoulders, neck, right and left elbows, right and left wrists, chest, middle spine, lower spine, right and left hips, pelvis, right and left knees, right and left ankles, and right and left feet. Other embodiments may include determining positions of additional, fewer, or other body parts.

Data captured by motion capture devices 114 may be processed by the system 102 (e.g., via computing device 118 or processing logic of one or more motion capture devices 114) and/or other system (e.g., backend system 104) to form a 3D model of the user's position as a function of time. Such processing may utilize any suitable collection of information captured by system 102, such as 2D images, 3D images, distance information, position information, or other suitable information.

In one embodiment, system 102 captures 3D point clouds that may be input into a neural network (e.g., that executes an artificial intelligence (AI) function) or other logic to reconstruct the user's body segments (e.g., in the form of a skeleton) in 3D space. In another embodiment, system 102 uses two or more motion capture devices 114 each comprising at least one RGB sensor and provides captured data to a neural network or other logic to construct a 3D skeleton directly. The neural network or other logic used to determine the user's position in 3D space may be implemented in whole or in part by computing device 118, one or more motion capture devices 114 (e.g., by processing logic resident thereon), or other system (e.g., backend system 104). In one embodiment, the computing device 118 may communicate captured data (e.g., raw image data and/or processed image data) to one or more other computing devices (e.g., within backend system 104) for processing. Various embodiments may employ different types of processing locally (e.g., by computing device 118) or remotely (e.g., by backend system 104). For example, in one embodiment, the computing device 118 may compress the raw image data and send it to a remote system for further processing. As another example, the computing device 118 may locally utilize a neural network to execute an AI function that identifies the user's segments (e.g., skeleton) without involving a remote system for the segment detection.

In various embodiments, display 116 (which may, e.g., comprise any suitable electronic display) may provide instruction associated with movement of the user 112. In various embodiments, the determination and/or generation of the instruction to provide to the user via display 116 may be performed by computing device 118, backend system 104, or a combination of computing device 118 and backend system 104. In some instances, the user 112 may be oriented in a forward position (e.g., facing the display 116) during an activity so that the user can view instruction provided via the display 116. In some embodiments, display 116 may be integrated with computing device 118 or coupled thereto.

A user 112 may issue commands to control the system 102 using any suitable interface. In a first example, user 112 may issue commands via body movements. For example, the user 112 may raise an arm to initiate a control session and then move the arm to select a menu item, button, or other interface element shown on the display 116. The display may update responsive to movement of the user 112. For example, a cursor may be displayed by the display 116 and movement of the user may cause the cursor to move. When a user's hand position (e.g., as indicated by the cursor) corresponds with the location of an interface element on the display 116, the interface element may be activated (e.g., via enlargement or highlighting of the interface element) and then the user may perform a gesture (e.g., make a first or wave a hand) to cause the system 102 to initiate the action that corresponds to the interface element. Thus, in one example, the user 112 may control the system 102 using contactless gestures. As another example, the system 102 may comprise a directional microphone (e.g., the microphone may be integrated with computing device 118 and/or display 116) that accepts voice commands from the user 112 to control the system 102. In one such example, the user 112 may initiate control by saying a key word which prompts the system 102 to listen for a voice command. As yet another example, a user 112 may control the system 102 by using an application on a mobile or other computing device that is communicatively coupled (e.g., by network 110 or a dedicated connection such as a Bluetooth connection) to the computing device 118. In this example, the device may be used to control the system 102 (e.g., navigate through an interface, enter profile information, etc.) as well as receive feedback from the system (e.g., workout statistics, profile information, etc.). In various embodiments, system 102 may implement any one or more of the above examples (or other suitable input interfaces) to accept control inputs.

In various embodiments, system 102 renders the dynamic posture of the user 112 on the display 116 in real-time during performance of an activity by the user. Thus, when the user views the display 116, the user may monitor his or her movement as if the display 116 were a mirror.

In various embodiments, display 116 may display a trainer performing an example movement pattern for an activity to the user 112. The example movement pattern may take any suitable form (such as any of the representation formats described below with respect to a trainer or user 112). In some embodiments, the display of the trainer may be video (or a derivation thereof) of one or more experts of expert network system 108 (or another user 112 of the system 100 that is deemed to have acceptable form) performing the movement.

In various embodiments, the trainer may be displayed simultaneously with the user 112 or the system 102 may alternate between display of the trainer and the user. The trainer may be displayed at any suitable time, such as before the user 112 performs a repetition of the activity, responsive to a request from the user 112, and/or responsive to a movement error by the user 112 performing the activity.

Any suitable representation of the user 112 or trainer may be displayed. For example, display 116 may display a visual representation of a 3D positional data set of a user 112 or trainer performing an activity, where a 3D positional data set may include any suitable set of data recorded over a time period allowing for the determination of positions of segments of a user 112 or trainer in a 3D space as a function of time. For example, a 3D positional data set may include a series of point clouds. As another example, a 3D positional data set may include multiple sets of 2D images that may be used to reconstruct 3D positions. As yet another example, a 3D positional data set may include a set of 2D images as well as additional data (e.g., distance information). The visual representation may include a video or an animation of the user 112 or trainer based on a respective set of 3D positional data (e.g., point clouds).

In some embodiments, when a 3D positional data set is displayed, a representation of the user 112 or trainer may be displayed along with detected parts of the body of the user 112 or trainer. For example, particular joints and/or body segments of the user 112 or trainer may be displayed. In some embodiments, a skeleton may be constructed from the detected body parts and may be displayed. In various embodiments, the processing to detect body parts from the raw image and/or positional data may be done in whole or in part by the computing device 118 or may be performed elsewhere in system 100 (e.g., by backend system 104, and/or one or more motion capture devices 114).

Figure 2A:
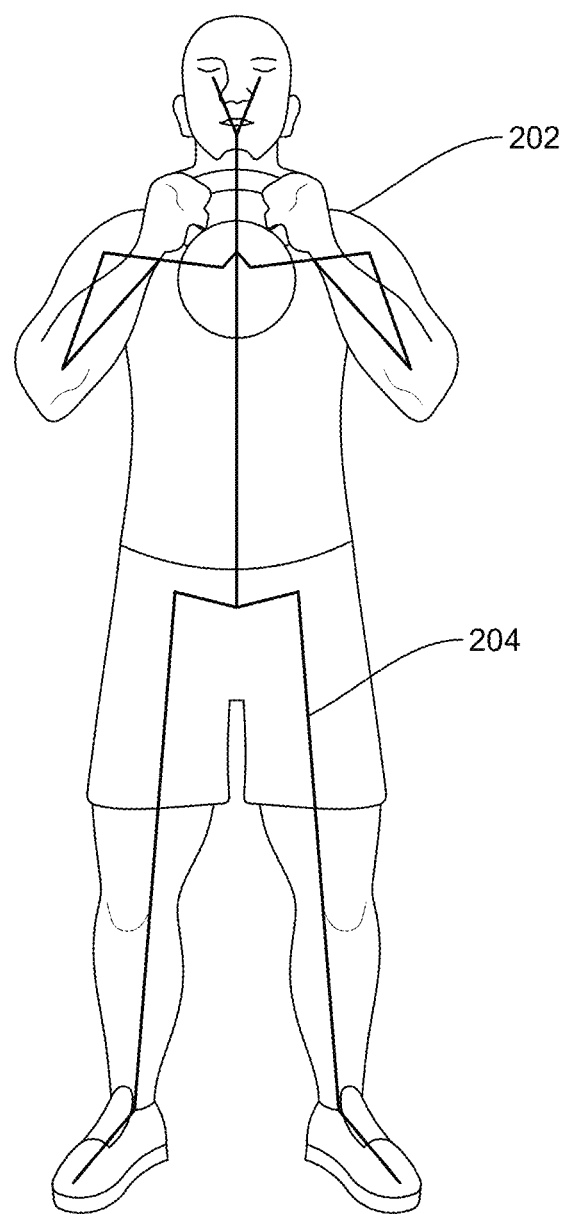
FIG. 2A illustrates a display of a representation of a user in accordance with certain embodiments.

FIG. 2A illustrates a display of a representation 202 of a user 112 in accordance with certain embodiments. In the embodiment depicted, the representation 202 of the user 112 as well as a skeleton 204 of detected body parts (e.g., joints or other body segments) along with connections between the body parts of the user 112 is displayed (where the skeleton may be overlaid on the representation 202 of the user 112). In some embodiments, the skeleton 204 is displayed in the same 3D space along with the representation 202. In other embodiments, the skeleton of the subject 112 may be displayed separately from the representation 202 or the representation 202 of the subject 112 may be omitted altogether and only the skeleton 204 displayed in some embodiments (and thus the skeleton itself could be the representation of the user 112 that is displayed).

In some embodiments, the representation 202 may comprise a series (in time) of colored images of the user 112. In one embodiment, the representation 202 may include only the joints of the subject. In another embodiment, the representation 202 may include the joints as well as additional visual data, such as connections between the joints. In various embodiments, a representation 202 may include a view of the entire user 112 as captured by the motion capture devices 114 and transformed (e.g., via a matrix) to the desired orientation, a view of a skeleton or other key points of the user 112, an avatar of the user 112 or superimposed on a representation of the user 112 (e.g., the representation 202 may be a simulated human or avatar with movements governed by the 3D positional data set), or an extrapolation of the images captured by motion capture devices 114 (e.g., a view of the user's back may be extrapolated from the captured data even when respective motion capture devices do not capture an image of the user's back directly). As described above, the form of any of the example representations of the user 112 may also be used as the form of representation of the trainer when the trainer is displayed.

FIG. 2B illustrates a representation of a user 112 from multiple points of view in accordance with certain embodiments. When the user 112 is performing an activity, the system may display the user from a default point of view as depicted in representation 252. Responsive to a determination that the movement of the user 112 is suboptimal, the system may change the point of view of the displayed representation based on the type of mistake made by the user. Representation 254 shows the user from a different point of view. The point of view in representation 254 may be displayed by the system, e.g., until the user 112 corrects the mistake or the system otherwise determines that a different point of view should be shown. More detail on how the system may determine which point of view to display is provided below.

Figure 3:
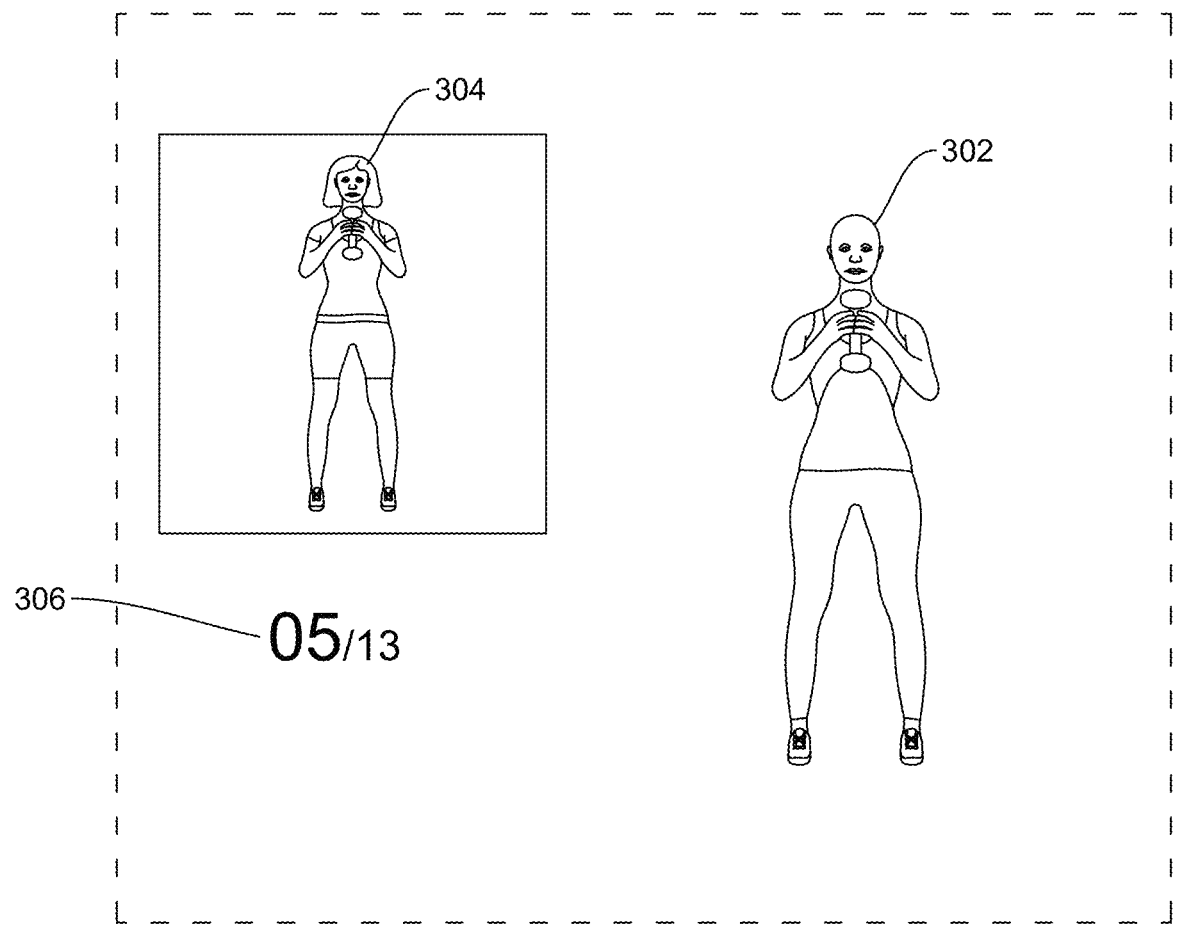
FIG. 3 illustrates a display comprising a representation of a user, a representation of a trainer, and a repetition tracker in accordance with certain embodiments.

FIG. 3 depicts a display comprising a representation 302 of a user 112, a representation 304 of a trainer, and a repetition tracker 306 in accordance with certain embodiments. In the depicted embodiment, system 102 may display, via repetition tracker 306, a number of repetitions of an activity that have been performed by the user 112. In some embodiments, the repetition tracker 306 may also display the number of target repetitions to be performed by the user 112 (and when the number of target repetitions is reached, the system 102 may transition, e.g., to the next activity or next set of the same activity).

In various embodiments, in order to enable counting of repetitions, an activity may be associated with one or more phases. A phase may be associated with one or more segments (e.g., body parts such as a joint or other portion of the subject 112) and corresponding positions of the one or more segments in a 3D space. For example, as illustrated in FIG. 11, such segments may include one or more of a head, right and left eyes, right and left clavicles, right and left shoulders, neck, right and left elbows, right and left wrists, chest, middle spine, lower spine, right and left hips, pelvis, right and left knees, right and left ankles, and right and left feet. Other embodiments may include additional, fewer, or other body parts that may be associated with a phase. The illustrated segments (or variations thereof) may similarly be used for any of the skeletons (e.g., detected skeleton, guide skeleton, etc.) described herein.

A 3D position associated with a segment for a phase may be represented as an absolute position in a coordinate system, as a relative position within a range of positions (so that the data may be used for subjects or users of various shapes and sizes), or in other suitable manner. These position(s) may be used for comparison with corresponding positions of 3D positional data of a user 112 to determine how closely the body positions of the users 112 match the stored body positions of the phases in order to determine when a phase has been reached during movement of the user 112.

As one example, for an activity such as a squat type, the activity may have a top phase and a bottom phase. When the system detects that the user 112 has reached the bottom phase and then the top phase, the system 102 may increment the counter. Thus, the configured phases may be utilized by the system 100 to implement a counter that tracks the number of repetitions of the activity that have been performed. In some embodiments, an activity may include a single phase or more than two phases.

In some embodiments, the phases set for an activity may additionally or alternatively be used to determine how closely the form of the user 112 matches a model movement form (in other embodiments the form of the user 112 may be compared with the model movement form without using such phases).

The comparison between the movement of the user 112 and the model movement form may be performed using any suitable collection of data points representing one or more positions of body parts of a user 112. For example, joints, segments coupled to one or more joints, and/or angles between segments of a detected skeleton of the user may be compared with corresponding joints, segments, and/or angles in a piecewise fashion (or a combination of certain joints, segments, or angles may be compared against corresponding combinations) of a model movement pattern.

In various embodiments, the difference between the user's movement and the model movement pattern may be quantified using any suitable techniques (e.g., linear algebra techniques, affine transformation techniques, etc.) to determine the distances between the model 3D positions of the selected body parts (e.g., as defined by the phases of the activity or otherwise defined) versus the detected 3D positions during a repetition performed by user 112. In various embodiments, the difference may be determined based at least in part on Euclidean distances and/or Manhattan distances between model 3D positions and detected 3D positions. In some embodiments, a relative marker such as a vector from a detected body part towards the model 3D position may be used in conjunction with the distance between the detected body part and the model 3D position to determine a difference between the user's movement and the model movement pattern.

In various embodiments, the comparisons may be made for any number of discrete points in time over the course of the movement. For example, in some embodiments, the comparisons may be made for each defined phase of the activity. As another example, the comparisons may be made periodically (e.g., every 0.1 seconds, every 33.3 milliseconds, etc.) or at other suitable intervals. In some embodiments, the comparisons may involve comparing a value based on positions detected over multiple different time points (e.g., to determine a rate and/or direction of movement) with a corresponding value of a model movement pattern.

Figure 4:
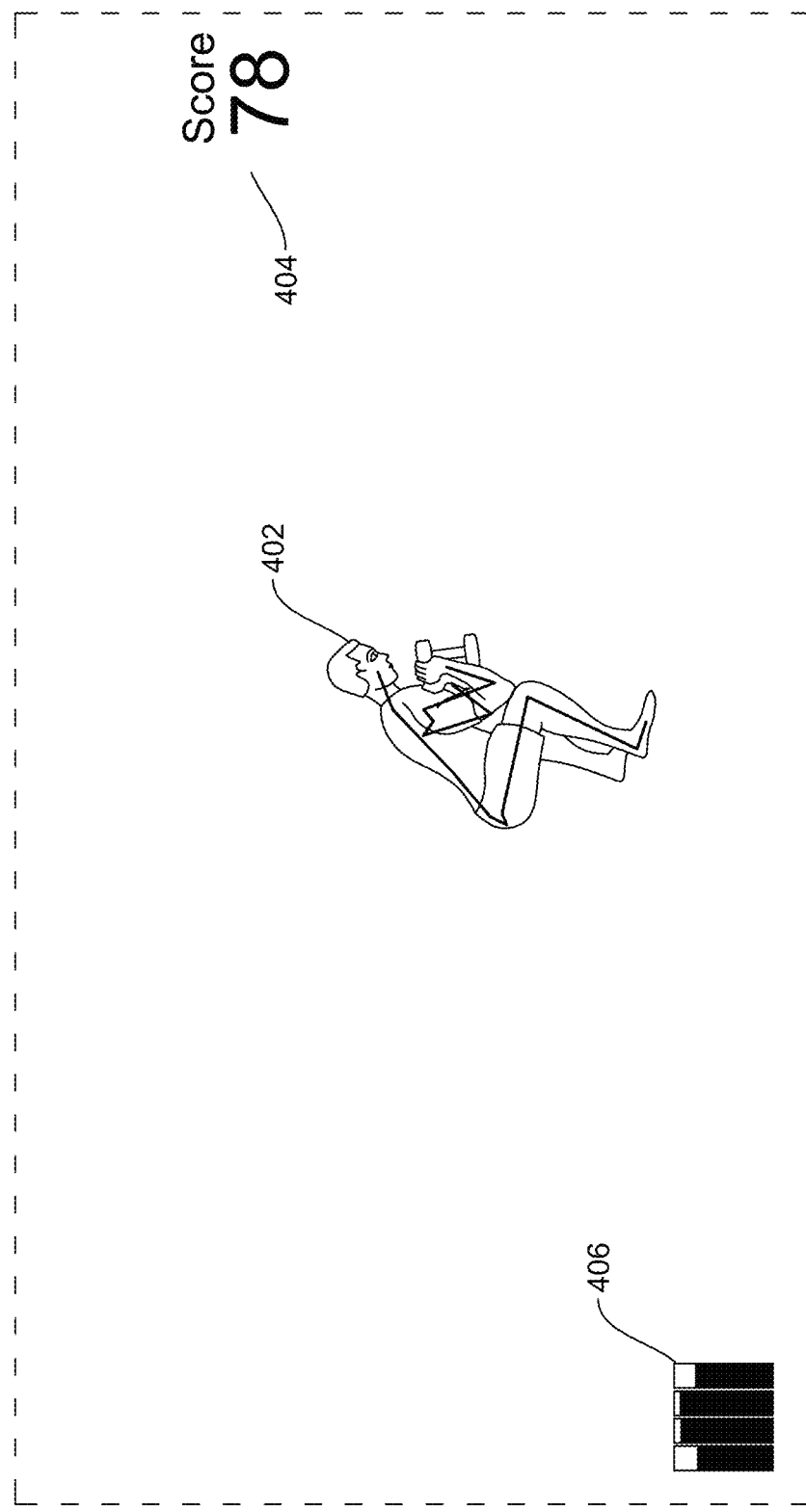
FIG. 4 illustrates a display comprising a representation of a user, a most recent score, and a score history in accordance with certain embodiments.

FIG. 4 depicts a display comprising a representation 402 of a user 112, a most recent score 404, and a score history 406 in accordance with certain embodiments. In various embodiments, system 102 may determine a score for a user's performance of a repetition of an activity. A score (e.g., 404) may indicate how closely the movement of the user 112 aligns with the model movement pattern which may be determined in any suitable manner, such as using any techniques described above. In the embodiment of FIG. 4, the score 404 of the latest repetition is shown in the upper right corner, while a bar graph representation of a score history 406 is shown in the lower left corner. The scores may provide instant feedback to a user 112 as well as allow a user 112 to see progress over time. In some embodiments, score histories from different activity sessions (e.g., performed on different days) are stored by the system 102 and the scores (or metrics based thereon, such as score averages) are made available to the user 112 (e.g., via display 116).

In various embodiments, system 102 may analyze movement form of the user 112 performing an activity and determine that the user has suboptimal movement form (also referred to herein as a "movement error" or "mistake"). In response, system 102 may alert the user 112 of the movement error. The determination that the user has suboptimal movement form may be made at any suitable granularity. For example, the determination may be made in response to the user committing a movement error during a repetition of an activity, a user committing a movement error for multiple consecutive repetitions of the activity, or a user committing a movement error for a certain percentage of repetitions of the activity.

The determination that the user has suboptimal movement form may be based on comparison of the movement of the user 112 with data representing a model movement pattern and/or data representing improper movement patterns (e.g., provided by expert network system 108). In various embodiments, deviations between the user's movement and a model movement pattern may indicate suboptimal movement form. For example, differences determined using any of the methods above (e.g., using comparisons between body parts of the user and the model movement form in a piecewise or aggregate fashion) that are above a certain threshold may indicate a suboptimal movement form. As another example, a similarity between the user's movement and an improper movement pattern may indicate a deviation from the model movement pattern and may thus indicate that a movement error has been committed. The determination that the user has suboptimal movement form may utilize any of the methods described above for comparing the user's form to the model movement pattern (and such methods may be adapted for comparing the user's form to one or more improper movement patterns).

A particular movement error may be associated with one or more body parts. When the position of these one or more body parts of the user 112 deviate from the position of the model movement pattern in a manner consistent with the movement error, the system 102 may detect that the user 112 has committed the movement error.

As an example, a movement error in which a user has a curved back during an activity (e.g., a squat) may be associated with the chest and the neck. As another example, a movement error in which a user has feet that are too narrow during the activity may be associated with the left and right feet. As yet another example, a movement error in which a user's knees cave outward during the activity may be associated with the left and right knee.

In some embodiments, the system 102 may also associate a weight with each body part associated with a movement error. The weight of a body part may indicate the relative importance of the body part in comparison of the user's movement form with a model movement pattern and/or one or more improper movement patterns. For example, if weights are used for a particular movement error and the chest is assigned a greater weight than the neck, then the position of the chest of the user 112 will be given greater relevance than the position of the neck in determining whether the user 112 has committed the movement error.

Different types of movement errors may have different thresholds for determining whether the movement error has been committed by the user 112, where one or more thresholds may be used in comparing the movement of the user 112 to the model movement pattern or one or more improper movement patterns. As various examples, a first movement error may be detected when a first body part deviates by more than a first threshold relative to a model movement pattern, a second movement error may be detected when a second body part deviates by more than a second threshold, a third movement error may be detected when a third body part deviates by more than a third threshold and a fourth body part deviates by more than a fourth threshold, and so on (similarly a threshold may be met when a user's body part deviates by less than the threshold from an improper movement pattern).

In some embodiments, system 102 may detect one or more of several types of movement errors associated with an activity. As just one example, a goblet squat activity may have detectable movement errors including "Not Utilizing the Full Squat", "Feet too narrow", "Rounded Back", "Feet too wide", "Knees Caving Outward", and "Knees Caving Inward." Each movement error could be associated with one or more different body parts, weights for the body parts, or comparison thresholds for determining whether the particular movement error has been committed by user 112. In some embodiments, each type of movement error may be associated with a distinct improper movement pattern that may be compared with the user's movement form.

Responsive to a determination that the user 112 has committed a movement error, the system 102 may provide instruction regarding how to improve the movement form. The instruction may be visual (e.g., displayed on display 116) and/or auditory (e.g., played through computing device 118 or display 116). In various embodiments, the system 102 may provide real time prompts to the user 112 to assist the user in achieving proper movement form. Alternatively or in addition, system 102 may store indications of prompts and provide the prompts at any suitable time. For example, the system 102 may provide prompts automatically when the corresponding movement errors are detected or provide the prompts responsive to a request from the user, e.g., after a workout set is completed, after an entire workout is completed, or prior to beginning a workout set (e.g., the prompts may be from a previous workout and the user 112 may desire to review the prompts for an activity prior to performing the activity again).

In some embodiments, the instruction provided may include a representation (e.g., an example movement pattern) of a trainer performing the activity (e.g., which may or may not be derived from a model movement pattern that is compared against the user's movement pattern). In various embodiments, responsive to a detection of a movement error, an example movement pattern of the trainer performing the activity is shown (e.g., from an optimal point of view) to illustrate how the movement error may be corrected. In some embodiments, the displayed example movement pattern of the trainer may include a full repetition of the activity or a portion of a repetition (e.g., to focus on the portion of the repetition in which the movement error was detected). In various embodiments, the specific movement and/or body parts associated with the movement error may be highlighted on the view of the trainer as the trainer moves through the particular activity.

In some embodiments, system 102 may provide an onscreen representation of the user 112 from an optimal point of view to highlight and correct the user's form. In one embodiment, when a user begins an exercise, the system 102 may display the user from a default point of view associated with the activity (different activities may have different default points of view). The system 102 may then change the point of view of the user 112 responsive to a determination that the user has committed a movement error (and that the optimal point of view is different from the default point of view). This may be performed without requiring the user 112 to change an orientation with respect to the motion capture devices 114 (e.g., the representation of the user 112 at the optimal point of view may be constructed from the data captured by motion capture devices 114).

In some embodiments, when a movement error is detected, the display of both the trainer and the user may be rotated to the same point of view associated with the particular movement error in order to illustrate the prescribed correction. The system may display the representation of the trainer or user in any suitable format (e.g., any of those described above with respect to representation 202 or in other suitable formats). Thus, in various embodiments, the system 102 may have the capability of rotating the user's image in 3D space to any suitable point of view and displaying an example movement pattern (e.g., of the trainer) alongside the user's actual movement at the same point of view (or a substantially similar point of view) in real time. In some embodiments, different points of view may be used for the representations of the trainer and for the user 112 for particular movement errors.

The particular point of view to be used to illustrate the correction of the error (e.g., by displaying the representation of the user 112 and/or the trainer) may be determined based on the type of movement error committed by the user 112. Each activity may be associated with any number of possible movement errors that are each associated with a respective optimal point of view of the user or trainer. Thus, when a movement error is detected, the associated optimal point of view is determined, and the representation of the user 112 or trainer is then displayed from that optimal point of view. For example, for a first type of movement error, the point of view may be a first point of view; for a second type of movement error, the point of view may be a second point of view; and so on. As just one example, if the movement error is an incorrect angle of the spine, the point of view may be a side view of the user or trainer, whereas if the movement error is an incorrect spacing of the feet, the point of view may be a front or back view of the user or trainer.

In some embodiments, a movement error may be associated with more than one optimal point of view. For example, the first time a movement error is detected, a first optimal view associated with the movement error is used to display the representation of the user or trainer while the second time (or some other subsequent time) the movement error is detected, a second optimal view associated with the movement error is used.

Figure 5:
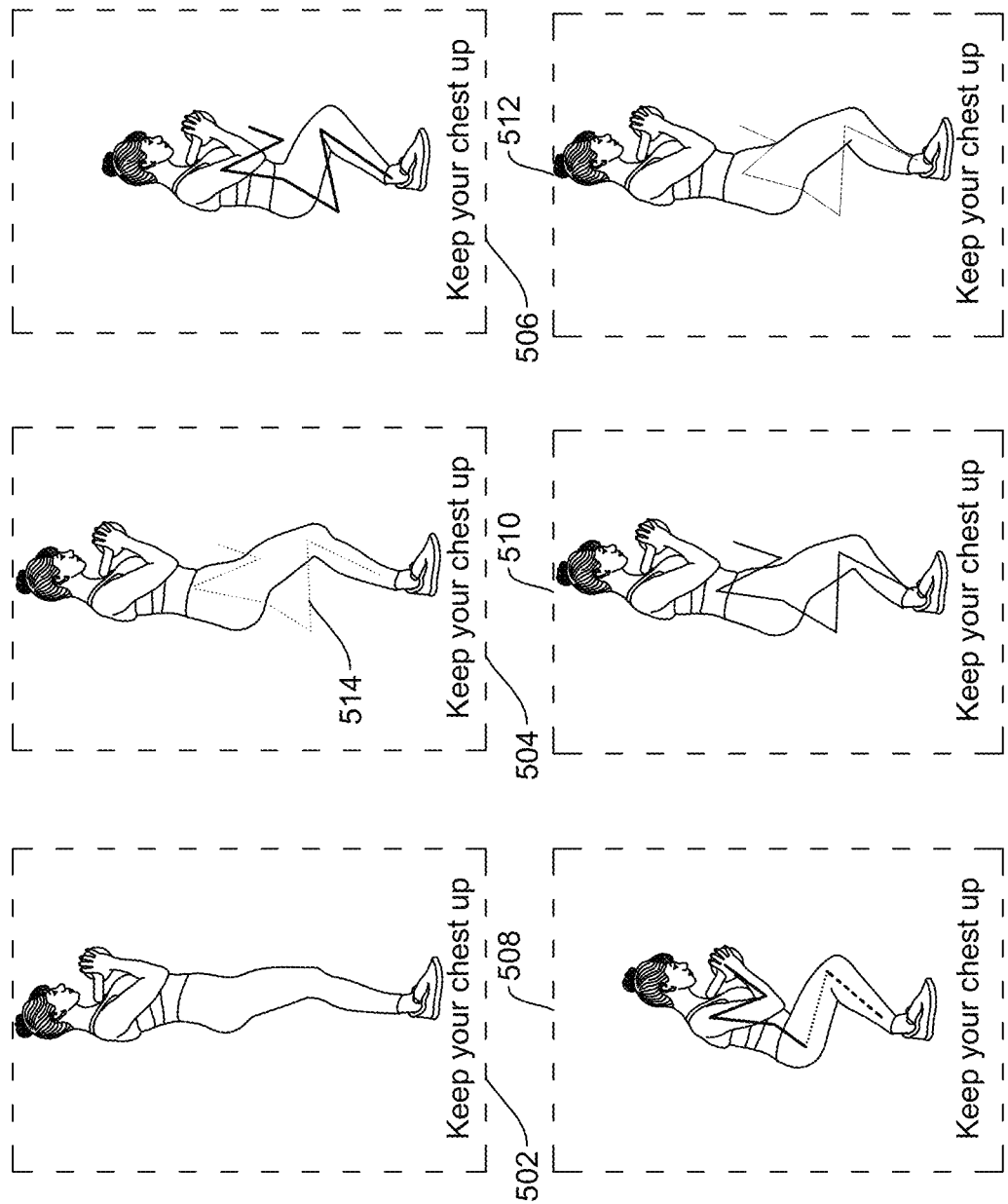
FIG. 5 illustrates a series of images that may be generated by system and displayed to provide movement instruction to user.

FIG. 5 illustrates a series of images that may be generated by system 102 and displayed (e.g., by display 116) to provide movement instruction to user 112. The images may be part of a video stream that is displayed by the display 116. In 502, the user 112 is beginning a repetition of an exercise. Because a suboptimal movement pattern has been detected (e.g., in a previous repetition of the exercise), the system 102 displays a corrective message: "Keep your chest up".

In some embodiments, system 102 may display a guide skeleton 514 to preview the correct movement form. This guide skeleton 514 may be grounded at (e.g., anchored to) a base position equal to the user's current position (e.g., standing in the same spot as the user or otherwise aligned with the user), so that the user 112 does not need to change location to line up with the guide skeleton. In one embodiment, once the base position of the guide skeleton is established, the base position of the guide skeleton does not change for the remainder of an instance of the activity being performed (e.g., for a repetition or a set of repetitions of the activity).

In some embodiments, the guide skeleton may be selected based on the type of detected movement error as a fixed position depicted by the guide skeleton may be selected to illustrate a position that needs correction. As another example, the guide skeleton may be oriented from the optimal point of view associated with the movement error. In various embodiments, the guide skeleton is oriented from the same point of view as the representation of the user 112.

In some embodiments, the guide skeleton 514 will fade in gradually as a user gets close to a target position of the correction (e.g., as represented by a model position). For example, in 504, the user 112 begins squatting down and the guide skeleton 514 starts to fade in (illustrated by dotted lines). In 506, the user 112 is closer to the target position and the lines of the guide skeleton 514 are brighter than at 504.

In one embodiment, the guide skeleton 514 is a particular color (e.g., blue) by default and a portion or all of the guide skeleton may change color (e.g., to green) or brightness when the position of the detected skeleton of the user matches up with the guide skeleton. In one example, the guide skeleton may include multiple segments and each segment may individually change color when the corresponding segment of the user's detected skeleton matches up with the respective segment. In some embodiments, the color change is gradual and is based on a difference between the position of a segment of the guide skeleton and the corresponding segment of the user's detected skeleton. When the difference is larger, the color of the segment of the guide skeleton may include a larger component of the original color and as the difference decreases, the guide skeleton may include decreasing amounts of the original color (e.g., blue) and increasing amounts of the new color (e.g., green). When the difference is below a threshold (e.g., indicating that the position of that segment is correct), an additional color effect may be displayed (e.g., the segment may flash brightly or the skeleton segment may become thicker).

In 508, part of the user's body (e.g., the calf, fibula, and/or tibia) is aligned with the corresponding segment of the guide skeleton, another part (e.g., the femur or thigh) is almost aligned with the corresponding segment of the guide skeleton (and may be displayed differently, such as in a slightly different color and/or brightness which is represented by different dashing of the lines in 508), and the remaining portion of the user's body is not as closely aligned. The target position is not achieved by the user 112 in this illustration. At 510 and 512, the user returns towards an initial position and the guide skeleton fades away.

Figure 6:
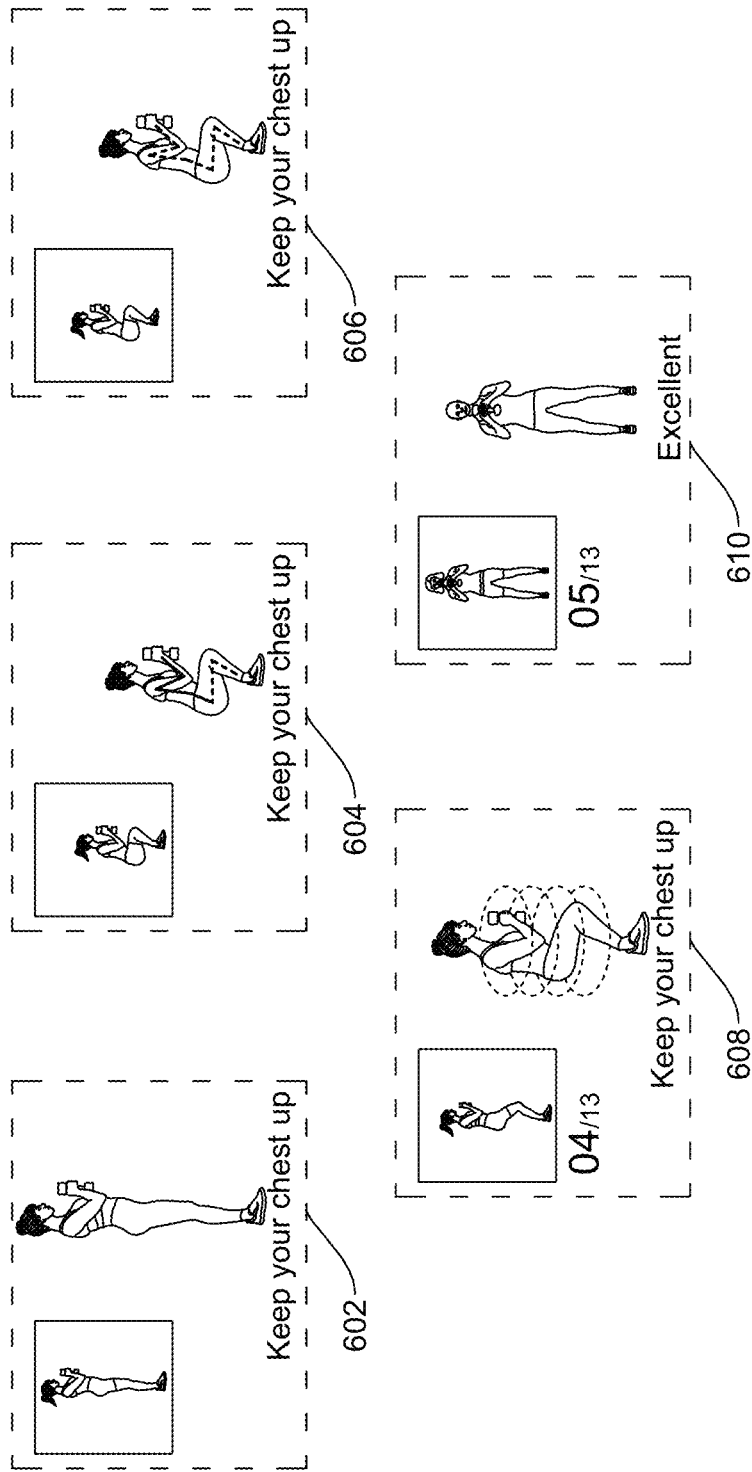
FIG. 6 illustrates an example series of images that may be generated by system and displayed to provide movement instruction to user.

FIG. 6 illustrates an example series of images that may be generated by system 102 and displayed (e.g., by display 116) to provide movement instruction to user 112. The images may be part of a video stream that is displayed by the display 116. At 602, the user begins a repetition of an exercise. The display 116 shows the example movement pattern in the upper left corner and the representation of the user 112 in the middle. Because a suboptimal movement pattern has been detected (e.g., in a previous repetition of the activity), the point of view of the display of the user 112 (and the trainer) has been changed from the default point of view (which is shown at 610) to a side view to allow the user to view her chest in association with the personalized feedback ("Keep your chest up") displayed by the system 102.

At 604, the user 112 has squatted down and is at or near the target position to be corrected. While the lower half of the user is correctly aligned with the guide skeleton, the upper half is still misaligned (in various embodiments, the misaligned segments may be a different color from the aligned segments, illustrated here by different dashing in the segments). At 606, the user has corrected position and the entire guide skeleton has turned the same color (illustrated by each segment having the same dashing). At 608 an animation is played wherein the guide skeleton disappears to indicate that the correct form has been attained and an encouraging message (e.g., "Excellent!") is presented at 610.

In one embodiment, once all of the guide skeleton and user segments are successfully aligned (or it is otherwise determined that the movement error has been corrected), the point of view may transition back to the default view. For example, the point of view may be changed back to the initial point of view of the display of the user (e.g., a frontal point of view).

As depicted in FIGS. 5 and 6, the view showing the user 112 at the optimal point of view may also include one or more visual targets for the user's body parts so that the user can align with the proper form. The visual targets may include one or more of a written message with movement instruction such as "keep your chest up" or "bend your knees more", an auditory message with movement instruction, or the guide skeleton showing a target position.

In some embodiments, system 102 may detect multiple errors in the user's movement over one or more repetitions. For example, during a repetition, system 102 may detect that a user's knees should bend more and the user's chest should be kept higher. In one embodiment, when multiple errors are detected, system 102 may focus its feedback on the most egregious error and utilize that error's associated optimal point of view and/or visual or audio prompt(s). Which movement error is most egregious could be determined in any suitable manner. For example, the movement error that is the most dangerous of the detected movement error could be selected as the most egregious movement error. As another example, the movement error that represents the furthest deviation from the model movement pattern may be selected as the most egregious movement error. In another example, the movement error that occurs earliest in a repetition may be corrected first, as subsequent movement errors may result from this movement error.

In some embodiments, instruction regarding one or more other detected errors may be provided at a later time (e.g., after the user has corrected the most egregious error). In other embodiments, system 102 may show correction for the multiple errors simultaneously or for multiple errors in succession. When correction is shown for multiple errors and the errors have different optimal viewpoints, the view could transition through optimal viewpoints associated with the movement errors (e.g., an optimal viewpoint associated with a first movement error may alternate with an optimal viewpoint associated with a second movement error). Alternatively, a viewpoint that is based on both optimal viewpoints may be used (e.g., a viewpoint that is in between the two optimal viewpoints that provides a balance between the two optimal viewpoints may be identified and used).

In various embodiments, system 102 may store activity profiles, where an activity profile includes configuration information that may be used to provide instruction for a specific activity, such as a weightlifting exercise (e.g., clean and jerk, snatch, bench press, squat, deadlift, pushup, etc.), a plyometric exercise (e.g., a box jump, a broad jump, a lunge jump, etc.), a movement specific to a sport (e.g., a baseball or golf swing, a discus throw), a dance move, a musical technique (e.g., a bowing technique for a violin, a strumming of a guitar, etc.), or other suitable movement pattern. An activity profile may be used by system 102 to provide feedback about the activity to any number of users 112.

For example, motion capture and feedback system 102 may track the motion of a user 112 performing an activity and compare positional data of the user 112 with parameters stored in the activity profile in order to provide feedback to the user 112 (e.g., by providing corrective prompts for mistakes and rotating a display of the user to an optimal point of view).

An activity profile for an activity may include one or more parameters used to provide instruction to a user 112. For example, the parameters of an activity profile may include any one or more of the following parameters specific to the activity (or any of the other information described above with respect to the features of the system 102): 3D positions for one or more specified segments of a subject (e.g., a trainer) at specified phases of a model movement pattern for an activity, 3D positions for one or more specified segments of a subject at specified phases for one or more movement errors, weights for the specified segments, parameters (e.g., thresholds) to be used in determining whether a mistake has been committed by a user 112, optimized points of view for correction of the one or more mistakes, and corrective prompts for the one or more mistakes.

Figure 7:
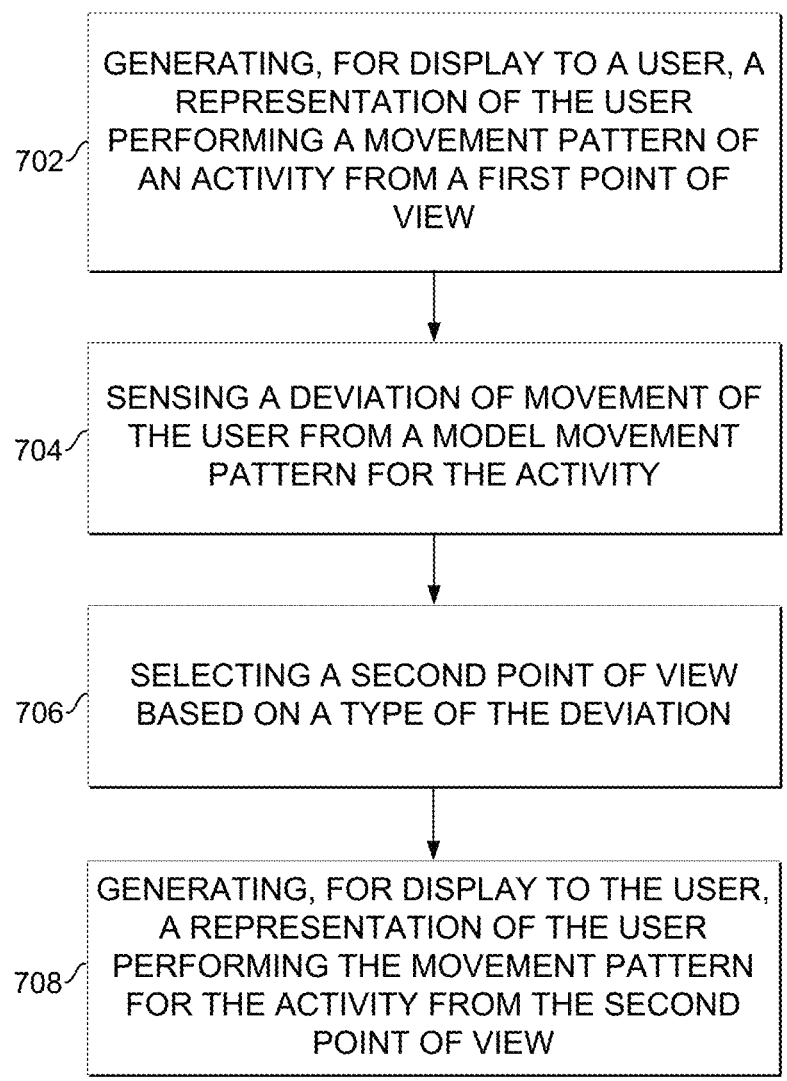
FIG. 7 illustrates a flow for providing movement based instruction in accordance with certain embodiments.

FIG. 7 illustrates a flow for providing movement based instruction in accordance with certain embodiments. At 702, a representation of the user performing a movement pattern of an activity from a first point of view is generated for display to a user. At 704, a deviation of movement of the user from a model movement pattern for the activity is sensed. At 706, a second point of view based on a type of the deviation is selected. At 708, a representation of the user performing the movement pattern for the activity from the second point of view is generated for display to the user.

FIGS. 9A-9D illustrates various views of a computing device 900 incorporating various components of system 100. For example, device 900 may include motion capture devices 114A and 114B as well as other components that may implement all or a portion of computing device 118. In the embodiments depicted, device 900 includes a housing comprising a housing base 902 and a housing lid 904 to be placed over the housing base. The housing encloses the components of the device 900. The housing base includes vents on the bottom and the rear for airflow and apertures for power and video cabling.

In some embodiments (e.g., as depicted in FIG. 9C), the housing base 902 and housing lid 904 may each comprise a plurality of sections that may be coupled together to form the housing.

Various computing components may be placed within the housing of device 900. In the embodiments depicted in FIGS. 9A-9D, motion capture devices 114A and 114B are placed proximate opposite ends of the housing and are angled slightly inwards (e.g., roughly 10 degrees) relative to the length of the housing. In one embodiment, the motion capture devices 114A and 114B are placed roughly 5 feet apart. In one embodiment, motion capture devices 114 are Azure Kinect or Kinect 2 devices utilizing time of flight imaging techniques.

As depicted in FIG. 9D, additional computing components 906 and 908 may be placed within the housing. Components 906 and 908 may include any suitable circuitry to provide functionality of the device 900 (which may implement at least a portion of computing device 118). For example, component 906 may be a power supply and component 908 may include a computing system comprising one or more of a processor core, graphics processing unit, hardware accelerator, field programmable gate array, neural network processing unit, artificial intelligence processing unit, inference engine, data processing unit, or infrastructure processing unit.

FIGS. 10A-10B depict another example computing device 1000 which may have any of the characteristics of computing device 900. FIG. 10A depicts the assembled computing device 1000 while FIG. 10B depicts an exploded view of the computing device 1000.

As FIG. 10B shows, the housing of computing device 1000 may comprise a bottom panel 1002, a rear panel 1004 with fins for airflow and apertures for power and video cabling, a front panel 1006 with apertures for light sources and/or camera lenses of motion capture devices 114A and 114B, and a top panel 1008.

Referring again to FIG. 1, computing device 118 may include any one or more electronic computing devices operable to receive, transmit, process, and store any appropriate data. In various embodiments, computing device 118 may include a mobile device or a stationary device capable of connecting (e.g., wirelessly) to one or more networks 110, motion capture devices 114, or displays 116. As examples, mobile devices may include laptop computers, tablet computers, smartphones, and other devices while stationary devices may include desktop computers, televisions (e.g., computing device 118 may be integrated with display 116), or other devices that are not easily portable. Computing device 118 may include a set of programs such as operating systems (e.g., Microsoft Windows, Linux, Android, Mac OSX, Apple iOS, UNIX, or other operating system), applications, plug-ins, applets, virtual machines, machine images, drivers, executable files, and other software-based programs capable of being run, executed, or otherwise used by computing device 118.

Backend system 104 may comprise any suitable servers or other computing devices that facilitate the provision of features of the system 100 as described herein. In various embodiments, backend system 104 or any components thereof may be deployed using a cloud service such as Amazon Web Services, Microsoft Azure, or Google Cloud Platform. For example, the functionality of the backend system 104 may be provided by virtual machine servers that are deployed for the purpose of providing such functionality or may be provided by a service that runs on an existing platform. In one embodiment backend system 104 may include a backend server that communicates with a database to initiate storage and retrieval of data related to the system 100. The database may store any suitable data associated with the system 100 in any suitable format(s). For example, the database may include one or more database management systems (DBMS), such as SQL Server, Oracle, Sybase, IBM DB2, or NoSQL databases (e.g., Redis and MongoDB).

Application server 106 may be coupled to one or more computing devices through one or more networks 110. One or more applications that may be used in conjunction with system 100 may be supported with, downloaded from, served by, or otherwise provided through application server 106 or other suitable means. In some instances, the applications can be downloaded from an application storefront onto a particular computing device using storefronts such as Google Android Market, Apple App Store, Palm Software Store and App Catalog, RIM App World, etc., or other sources. As an example, a user 112 may use an application to provide information about physical attributes, fitness goals, or other information to the system 100 and use the application to receive feedback from the system 100 (e.g., workout information or other suitable information). As another example, experts in the expert network system 108 may use an application to receive information about a user 112 and provide recommended workout information to the system 100.

In general, servers and other computing devices of backend system 104 or application server 106 may include electronic computing devices operable to receive, transmit, process, store, or manage data and information associated with system 100. As used in this document, the term computing device, is intended to encompass any suitable processing device. For example, portions of backend system 104 or application server 106 may be implemented using servers (including server pools) or other computers. Further, any, all, or some of the computing devices may be adapted to execute any operating system, including Linux, UNIX, Windows Server, etc., as well as virtual machines adapted to virtualize execution of a particular operating system, including customized and proprietary operating systems.

In some embodiments, multiple backend systems 104 may be utilized. For example, a first backend system 104 may be used to support the operations of system 102 and a second backend system 104 may be used to support the operations of expert network 108.

Servers and other computing devices of system 100 can each include one or more processors, computer-readable memory, and one or more interfaces, among other features and hardware. Servers can include any suitable software component or module, or computing device(s) capable of hosting and/or serving a software application or services (e.g., services of backend system 104 or application server 106), including distributed, enterprise, or cloud-based software applications, data, and services. For instance, servers can be configured to host, serve, or otherwise manage data sets, or applications interfacing, coordinating with, or dependent on or used by other services. In some instances, a server, system, subsystem, or computing device can be implemented as some combination of devices that can be hosted on a common computing device, server, server pool, or cloud computing environment and share computing resources, including shared memory, processors, and interfaces.

Computing devices used in system 100 (e.g., computing devices 118 or computing devices of expert network system 108 or backend system 104) may each include a computer system to facilitate performance of their respective operations. In particular embodiments, a computer system may include a processor, memory, and one or more communication interfaces, among other components. These components may work together in order to provide functionality described herein.

A processor may be a microprocessor, controller, or any other suitable computing device, resource, or combination of hardware, stored software and/or encoded logic operable to provide, either alone or in conjunction with other components of computing devices, the functionality of these computing devices. For example, a processor may comprise a processor core, graphics processing unit, hardware accelerator, application specific integrated circuit (ASIC), field programmable gate array (FPGA), neural network processing unit, artificial intelligence processing unit, inference engine, data processing unit, or infrastructure processing unit. In particular embodiments, computing devices may utilize multiple processors to perform the functions described herein.

A processor can execute any type of instructions to achieve the operations detailed herein. In one example, the processor could transform an element or an article (e.g., data) from one state or thing to another state or thing. In another example, the activities outlined herein may be implemented with fixed logic or programmable logic (e.g., software/computer instructions executed by the processor) and the elements identified herein could be some type of a programmable processor, programmable digital logic (e.g., FPGA), an erasable programmable read only memory (EPROM), an electrically erasable programmable ROM (EEPROM)), or an ASIC that includes digital logic, software, code, electronic instructions, or any suitable combination thereof.

Memory may comprise any form of non-volatile or volatile memory including, without limitation, random access memory (RAM), read-only memory (ROM), magnetic media (e.g., one or more disk or tape drives), optical media, solid state memory (e.g., flash memory), removable media, or any other suitable local or remote memory component or components. Memory may store any suitable data or information utilized by computing devices, including software embedded in a computer readable medium, and/or encoded logic incorporated in hardware or otherwise stored (e.g., firmware). Memory may also store the results and/or intermediate results of the various calculations and determinations performed by processors.

Communication interfaces may be used for the communication of signaling and/or data between computing devices and one or more networks (e.g., 110) or network nodes or other devices of system 100. For example, communication interfaces may be used to send and receive network traffic such as data packets. Each communication interface may send and receive data and/or signals according to a distinct standard such as an IEEE 802.11, IEEE 802.3, or other suitable standard. In some instances, communication interfaces may include antennae and other hardware for transmitting and receiving radio signals to and from other devices in connection with a wireless communication session.

System 100 also includes network 110 to communicate data between the system 102, the backend system 104, the application server 106, and expert network system 108. Network 110 may be any suitable network or combination of one or more networks operating using one or more suitable networking protocols. A network may represent a series of points, nodes, or network elements and interconnected communication paths for receiving and transmitting packets of information. For example, a network may include one or more routers, switches, firewalls, security appliances, antivirus servers, or other useful network elements. A network may provide a communicative interface between sources and/or hosts, and may comprise any public or private network, such as a local area network (LAN), wireless local area network (WLAN), metropolitan area network (MAN), Intranet, Extranet, Internet, wide area network (WAN), virtual private network (VPN), cellular network (implementing GSM, CDMA, 3G, 4G, 5G, LTE, etc.), or any other appropriate architecture or system that facilitates communications in a network environment depending on the network topology. A network can comprise any number of hardware or software elements coupled to (and in communication with) each other through a communications medium. In some embodiments, a network may simply comprise a transmission medium such as a cable (e.g., an Ethernet cable), air, or other transmission medium.

The functionality described herein may be performed by any suitable component(s) of the system. For example, certain functionality described herein as being performed by system 102 may be performed by backend system 104 or by a combination of system 102 and backend system 104. Similarly, certain functionality described herein as being performed by computing device 118 may be performed by backend system 104 or by a combination of computing device 118 and backend system 104.

Figure 12:
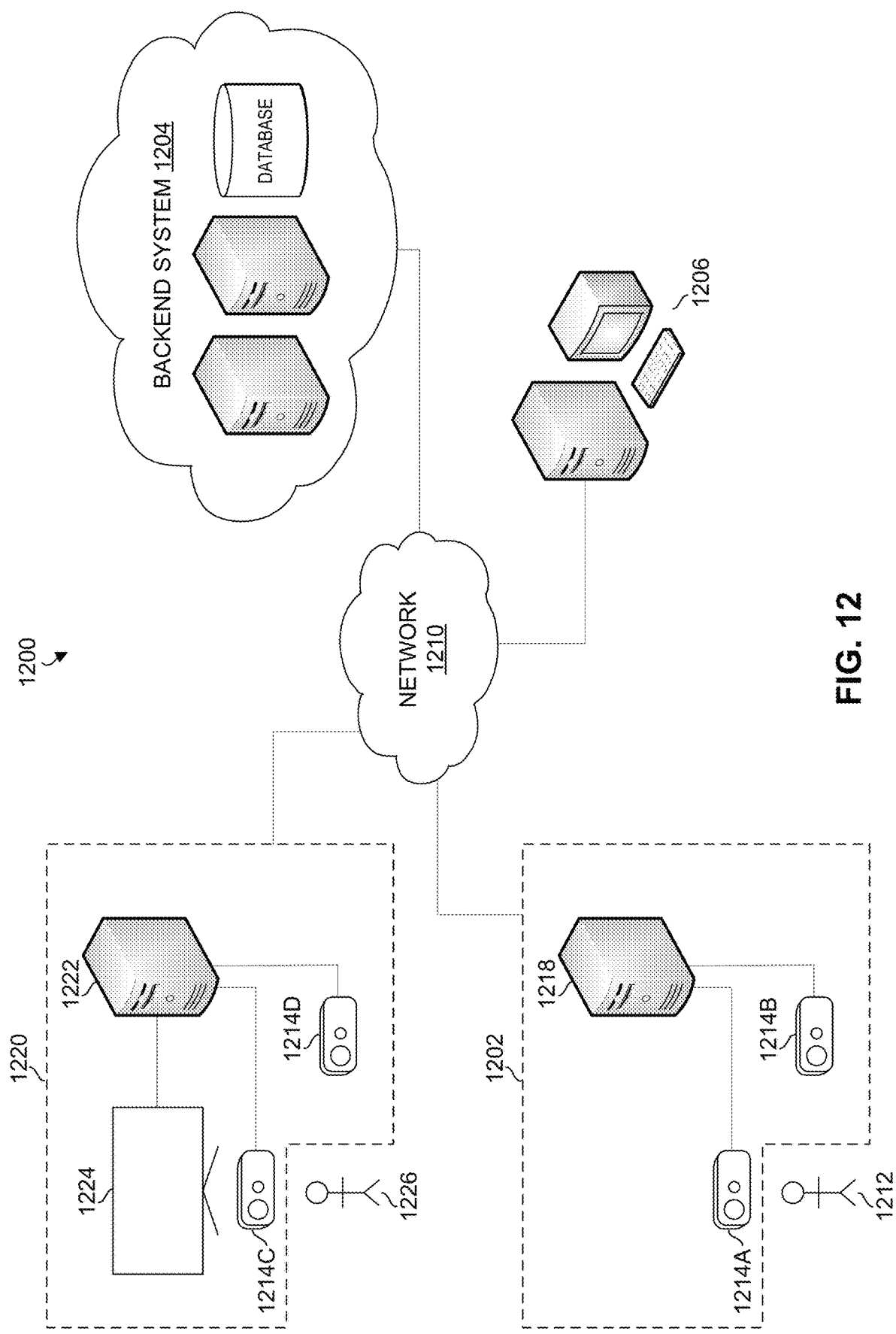
FIG. 12 illustrates a system to generate movement based instruction in accordance with certain embodiments.

FIG. 12 illustrates a system 1200 to generate movement based instruction in accordance with certain embodiments. System 1200 comprises a system for generating and providing movement based instruction. System 1200 includes a motion capture system 1202, backend system 1204, editor system 1206, and motion capture and feedback system 1220 coupled together through network 1210. The motion capture system 1202 includes motion capture devices 1214 (e.g., 1214A and 1214B), and computing device 1218. Other embodiments of system 1200 may include other suitable components or may omit one or more of the depicted components. System 1200 enables the generation, e.g., using editor system 1206, of movement based instruction programs based on motion data (e.g., captured by motion capture system 1202), which may be used to instruct end users using motion capture and feedback system 1220. For example, system 1202 may record a subject 1212 performing various activities and the captured data (or data processed therefrom) may be provided to editor system 1206. An editor utilizing the editor system 1206 may review visual representations (based on the captured data) of the subject 1212 performing the activities and may configure parameters in association with the visual representations to generate activity profiles. These activity profiles may then be used, e.g., by any number of motion capture and feedback systems 1220 to provide feedback (e.g., in a manner such as that described above in connection with FIGS. 1-7) based on the motion of users 1226 performing the same activities (e.g., by judging the quality of movements of the users 1226, showing the users and/or a trainer from an optimal viewpoint when suboptimal movement is detected, or other feedback described herein). Accordingly, system 1200 may be used to provide an editing platform for generating and providing movement based instruction. Although the system 1200 may be used to generate and provide movement based instruction for any suitable activity (e.g., such as any of the activities described herein), this disclosure will focus on application of the system 1200 to physical exercises.

In various embodiments, motion capture and feedback system 1220 may have any suitable characteristics of motion capture and feedback system 102. Similarly, motion capture system 1202 may have any suitable characteristics of the motion capture and feedback system 102 (e.g., the motion capture system 1202 may capture motion data using any of the methodologies used by motion capture and feedback system 102). In some embodiments, motion capture devices 1214, computing devices 1218 and 1222, display 1224, network 1210, or backend system 1204 may have any suitable characteristics of motion capture devices 114, computing device 118, display 116, network 110, or backend system 104 respectively. In some embodiments, the motion capture system 1202 and/or editor system 1206 may be utilized within an expert network system (e.g., 108) to generate movement based instruction.

Motion capture system 1202 is operable to record the motion of a subject 1212 performing an activity. The subject 1212 may be an entity capable of performing ideal and/or non-ideal movement patterns (also referred to herein as mistakes) for one or more activities. The movement of any one or more subjects 1212 may be recorded using motion capture devices 1214. The recorded data may then be used to generate movement based instruction. In one example, subject 1212 is a human (e.g., an expert trainer). In other embodiments, subject 1212 could be an animal, a mechanical object, or other suitable system with movement capability.

Motion capture devices 1214a and 1214b may capture multiple images (e.g., 2D or 3D images) of the subject 1212 over a time period to produce a video stream. In order to capture the images, a motion capture device 1214 may include one or more image sensors, such as any of those described above with respect to motion capture devices 114.

In the embodiment depicted, two discrete motion capture devices 1214 (1214A and 1214B) are shown as being located in different positions so as to capture the subject 1212 at multiple different angles. In other embodiments, any suitable number of motion capture devices 1214 may be employed. As in system 100, motion capture system 1202 includes any suitable number and types of motion capture devices placed at any suitable poses relative to the subject 1212 to enable capture of sufficient data to allow modeling of the skeleton of the subject 1212 in 3D space.

In some embodiments, the subject 1212 may wear special clothing or other wearable devices and locations of these wearable devices may be tracked by system 1202 in order to capture the position of various segments (e.g., body parts) of subject 1212. In some embodiments, the wearable devices may be used to estimate the 3D positions of various segments of subject 1212 to supplement data captured by one or more motion capture devices 1214 in order to improve the accuracy of the position estimation. In yet other embodiments, the wearable devices may be used to estimate the 3D positions of the segments of subject 1212 without the use of passive sensors such as cameras.

Motion capture system 1202 (either by itself or in conjunction with one or more other devices of system 1200) may track the movement of the subject 1212 by capturing data from motion capture devices 1214 (such as those listed above) and/or wearable devices and transforming or translating the captured data into representations of three dimensional (3D) positions of one or more segments (e.g., body parts) of the subject 1212. Data captured by motion capture devices 1214 may be processed by the system 1202 (e.g., via computing device 1218 or processing logic of one or more motion capture devices 1214) or other system (e.g., backend system 1204 or editor system 1206) to form a 3D model of the subject's position as a function of time. Such processing may utilize any suitable collection of information captured by system 1202, such as 2D images, 3D images, distance information, position information, or other suitable information.

In one embodiment, system 1202 captures 3D point clouds that may be input into a neural network (e.g., that executes an AI function) or other logic to reconstruct the subject's segments (e.g., skeleton) in 3D space. In another embodiment, system 1202 uses two or more motion capture devices 1214 each comprising at least one RGB sensor and provides captured data to a neural network or other logic to construct a 3D skeleton directly. The neural network or other logic may be implemented in whole or in part by computing device 1218, one or more motion capture devices 1214 (e.g., by processing logic resident thereon), or other system (e.g., backend system 1204 or editor system 1206). In one embodiment, the computing device 1218 may communicate captured data (e.g., raw image data and/or processed image data) to one or more other computing devices (e.g., within backend system 1204 or editor system 1206) for processing. Various embodiments may employ different types of processing locally (e.g., by computing device 1218) or remotely (e.g., by backend system 1204 or editor system 1206). For example, in one embodiment, the computing device 1218 may compress the raw image data and send it to a remote system for further processing. As another example, the computing device 1218 may locally utilize a neural network to execute an AI function that identifies the subject's segments (e.g., skeleton) without involving a remote system for the segment detection.

Editor system 1206 may provide (e.g., display directly or generate data to be used for displaying) a visual representation (referred to herein as a playback) of a 3D positional data set of a subject 1212 performing an activity to an editor of the editor system 1206, where a 3D positional data set may include any suitable set of data recorded over a time period allowing for the determination of positions of segments of a subject 1212 in a three dimensional space as a function of time. For example, a 3D positional data set may include a series of point clouds. As another example, a 3D positional data set may include multiple sets of 2D images that may be used to reconstruct 3D positions. As yet another example, a 3D positional data set may include a set of 2D images as well as additional data (e.g., distance information). In various embodiments, the playback may include a plurality of frames, wherein a frame may refer to the 3D positional data that is displayed at a particular instance of time and where the playback comprises a sequence of frames displayed at any suitable rate (e.g., 30 frames per second, 60 frames per second, etc.). In some embodiments, the frame rate of the playback matches the frame rate at which the 3D positional data is captured, though in other embodiments the frame rates may differ.

An editor may refer to any suitable user of the editor system 1206. For example, the editor may be an operator, programmer, or other suitable individual capable of providing input to the editor system 1206.

The editor may use a graphical user interface provided by the editor system 1206 to provide input relative to the playback of the 3D positional data or other suitable input in order to set parameters for a profile for the activity. The input relative to the playback may include any suitable input aided by viewing of the playback, such as a time position of the playback (e.g., to capture one or more parameters at that time position such as one or more positions of one or more segments of the subject 1212), a zoom level or point of view of the playback, one or more positions of one or more segments of the subject 1212, one or more positions of one or more segments of the subject 1212 extrapolated from the playback (e.g., the editor may manually select a position for a segment that is different from a displayed position of the segment to set a position of the segment for an ideal or non-ideal movement), or other suitable input received in association with the playback. This activity profile may be saved by the editor system 1206 and may be used by other systems (e.g., motion capture and feedback system 102 and/or 1220) to provide movement based instruction to any number of users performing the activity. For example, a motion capture and feedback system 102 or 1220 may track the motion of a user 112 or 1226 performing the activity and compare positional data of the user 112 or 1226 with parameters stored in the activity profile in order to provide feedback to the user 112 or 1226 (e.g., by providing corrective prompts for mistakes, rotating a display of the user to an optimal point of view, or providing other feedback described herein).

System 1220 may include motion capture devices 1214 (e.g., 1214C and 1214D) or other suitable devices (e.g., devices that may communicate with wearable sensors) that capture positional data representative of the movement of the user 1226 (e.g., using any of the techniques described above for tracking the motion of user 112 or subject 1212 or other suitable techniques). The positional data may be processed by computing device 1222 and/or other computing devices in the network (e.g., backend system 1204) and feedback that is based on the user's movement and the movement based instruction included in the activity profile may be provided to the user (e.g., via display 1224). The movement based instruction may be used to provide feedback to any suitable number of users 1226 utilizing respective motion capture and feedback systems 1220 (and/or 102).

Editor system 1206 may access 3D positional data of a subject 1212 performing an activity and provide editing capabilities to enable an editor of the editor system 1206 to create an activity profile that may be used by the system 1200 to provide feedback about the activity to, e.g., any number of users 1226. Editor system 1206 may be used to generate any suitable number of activity profiles, where each activity profile may include configured movement based instruction for a respective activity.

Editor system 1206 may be utilized to create activity profiles for any suitable movement based activities, such as any of those activities described above with respect to system 100 or other suitable movement patterns. Various examples below will focus on weightlifting activities.

In one embodiment, editor system 1206 may execute a software development kit (SDK) that provides the editing capabilities described herein. In other embodiments, editor system 1206 may execute any other suitable software application(s) to provide these capabilities.

In various embodiments, editor system 1206 may function as a platform upon which editors may develop movement based instruction applications (e.g., by utilizing an SDK or other software application providing the features described here) for use by end users. For example, one or more human editors associated with a first organizational entity may supply (e.g., upload) proprietary 3D positional data to the editor system 1206, utilize the editor system 1206 to generate activity profiles, and then deliver movement based instruction to subscribers or other users associated with the first organizational entity through one or more systems (e.g., 102, 1220) or other means (e.g., a software application) associated with (e.g., developed or controlled by) the first organizational entity. Similarly, a second organizational entity (e.g., through one or more human editors associated with the second organizational entity) may supply other 3D positional data to the editor system 1206 (or to a separate instance of editor system 1206), utilize the editor system to generate activity profiles, and then deliver movement based instruction to subscribers or other users associated with the second organizational entity through one or more other systems (e.g., 102, 1220) or other means (e.g., a software application) associated with (e.g., developed or controlled by) the second organizational entity.

In various embodiments, separate instances of a software application (e.g., SDK) providing the functionalities described herein with respect to the editor system 1206 may be provided to various entities such that each entity may utilize the software application (e.g., by running the software application on a computing device owned by or otherwise accessible to the respective entity) to develop movement based instruction specific to that entity. For example, an entity may generate or otherwise obtain 3D positional data of one or more subjects performing activities, provide that data to an instance of the software application specific to that entity, and use the instance of the software application to generate activity profiles as described herein.

In other embodiments, the editor system 1206 may be provided by a particular entity but may be accessible to multiple different entities (e.g., each having their own account) such that each entity may utilize the same editor system 1206 to generate activity profiles specific to that entity. For example, the editor system 1206 may be hosted in a cloud based environment and accessed by multiple different entities. In such embodiments, the editor system 1206 may include dedicated resources for storage, e.g., of 3D positional data and activity profiles, for the various entities so as to keep the data of the various entities isolated from each other.

Thus, editor system 1206 allows an editor to create an activity profile with information based on one or more sets of 3D positional data of a subject performing the activity (in some embodiments the 3D positional data may be captured by system 1202 or through another suitable motion capture system or data processed based on captured data) or other information associated with the activity. In various embodiments, the editor system 1206 may display or otherwise provide a playback of a 3D positional data set of a subject performing an activity. The playback may include a sequence of images that each provide a visual representation of segments of a subject at a particular point in time. Thus, the playback may be an animation or video of the subject based on a set of 3D positional data (e.g., point clouds or other suitable positional data).

The displayed playback may depict a subject 1212 demonstrating an activity any suitable number of times. In some embodiments, one or more 3D positional data sets that are played back by the editor system 1206 may include data of the subject 1212 demonstrating the activity using correct form (e.g., ideal movement patterns) and/or demonstrating the activity using incorrect form (i.e., mistakes).

In various embodiments, when a 3D positional data set is played back by editor system 1206, a representation of the subject 1212 may be displayed along with detected segments (e.g., joints or other body parts) of the subject's body. For example, particular joints and/or other body segments of the subject 1212 may be displayed. In some embodiments, a skeleton may be constructed from the detected body parts and may be displayed. In various embodiments, the processing to detect body parts from the raw image and/or positional data may be done by the editor system 1206 or may be performed elsewhere in system 1200 (e.g., by computing device 1218, backend system 1204, and/or one or more motion capture devices 1214). The processing to detect body parts may occur during capture of the subject 1212, during editing of the 3D positional data set within the editor system 1206 (after the subject 1212 has already been recorded), or at another suitable time (e.g., after the capture but before the editor system 1206 plays back the 3D positional data set).

Figure 13:
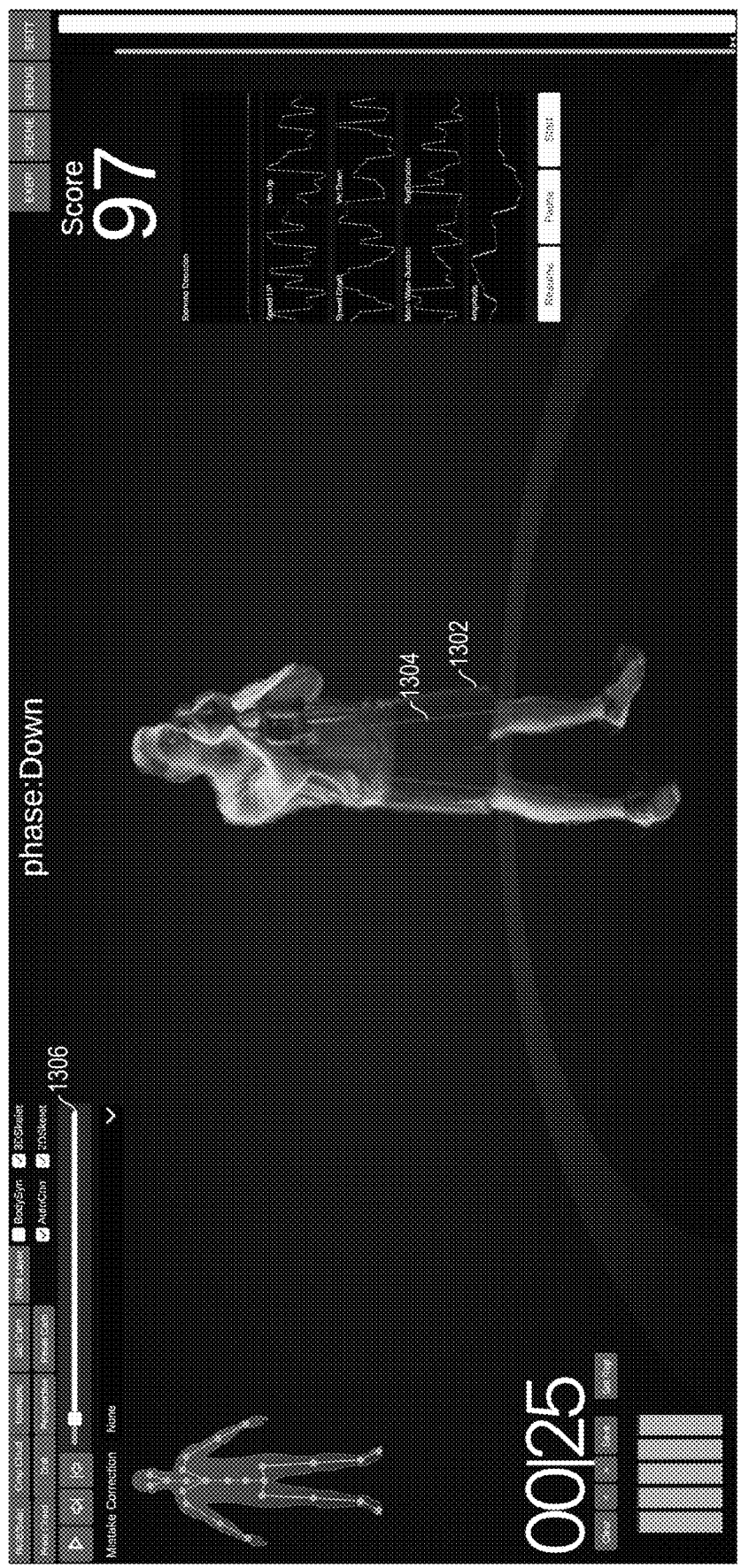
FIG. 13 illustrates a view of playback of a subject provided by an editor system in accordance with certain embodiments.

FIG. 13 depicts an example view of playback of a subject 1212 that may be provided by the editor system 1206 (where provision of a view may refer, e.g., to generation of display data including the view and/or the actual display of the view). In the embodiment depicted, a representation 1302 of the subject 1212 as well as a skeleton 1304 (or other grouping) of detected body parts of the subject 1212 is displayed. In some embodiments, the skeleton 1304 is displayed in the same 3D space along with the representation 1302. In other embodiments, the skeleton of the subject 1212 may be displayed separately from the representation 1302 or the representation 1302 of the subject 1212 may be omitted altogether in some embodiments. In various embodiments, any suitable segments of the subject 1212 may be displayed during the playback. In some embodiments, an editor may be able to select which segments are displayed during playback (e.g., using a control setting in editor system 1206). In some embodiments, the representation 1302 includes one or more color images or black and white images of the subject 1212. As another example, the representation 1302 may include only the joints of the subject. In yet other embodiments, the representation 1302 may be a simulated human or avatar with movements governed by the 3D positional data set. In various embodiments, a representation 1302 may be a view of the entire subject 1212 as captured by motion capture devices 1214 transformed (e.g., via a matrix) to the desired orientation, a view of a skeleton or other key points of the subject, an avatar superimposed on the subject, or an extrapolation of the images captured by motion capture devices 1214 (e.g., a view of the subject's back may be extrapolated from the captured data even when the motion capture devices 1214 do not capture an image of the subject's back directly).

The view illustrated in FIG. 13 may be referred to herein as a "main view". The main view may also include playback controls 1306. Any suitable playback controls may be included, such as a play button, a pause button, a fast forward button (which may move forward a single frame or any other number of frames), a rewind button (which may rewind a single frame or any number of frames), and a position slider (to show and allow manipulation of the position within the video). As the playback proceeds, the representation 1302 and skeleton 1304 are updated as a function of time based on the 3D positional data set.

Figure 14:
FIG. 14 illustrates a view of a representation and skeleton provided by the editor system of a subject after a change in a point of view in accordance with certain embodiments.

Editor system 1206 may allow an editor to rotate the point of view or the zoom level of the representation 1302 and/or skeleton 1304. For example, a simple click and drag operation performed in the display window by a mouse (or other suitable input device manipulation) could rotate the point of view of the representation 1302 and skeleton 1304. As another example, a scroll of a mouse wheel or other input device manipulation could change the zoom level. The change in the point of view or zoom level may be performed at any suitable time, such as before the playback begins, during playback, or while the playback is paused. In various embodiments, the editor system 1206 may be capable of providing a point of view from any suitable angle (e.g., from either side of the subject 1212, from the front of the subject 1212, from the back of the subject 1212, or from other point in between any of these as well as from variable elevations). FIG. 14 depicts an example view of the representation 1302 and skeleton 1304 of subject 1212 after the point of view has been changed by the editor.

Playback may enable a concept referred to herein as capture. At any suitable point of the playback, an editor may capture a skeleton (or other arrangement of one or more segments of the subject 112), e.g., by clicking a button, pressing one or more keys, or otherwise providing input to the editor system 1206. A capture may refer to a position for each of one or more body segments (e.g., joints) of subject 112 at a particular point in time of the playback. In some embodiments, one or more positions of a capture may be modified manually by an editor after they are captured from the position(s) of the subject 112 during playback (e.g., an editor could select a body part after it is captured and modify a captured position of the body part to a new position by entering a new coordinate for the new position, dragging the body part to a new position, or otherwise modifying the captured position or may shift a group of positions of different body parts concurrently). The captured positions (including modified captured positions in some examples) may be used as (or otherwise form the basis of) parameters of an activity file that are used to provide feedback to a user (e.g., 112, 1226).

Captures may be used, e.g., to define phases of activities for use in counting or scoring repetitions of the activity, to provide parameters for error detection, and/or to provide parameters for error correction. In various embodiments, a capture may be associated with a phase or a mistake. As an example, a capture may be defined by an editor as either a phase capture, a mistake detection capture, or a mistake correction capture. A phase, error detection scheme, or error correction scheme may each be based on any number of captures (including a single capture in some examples).

Figure 15:
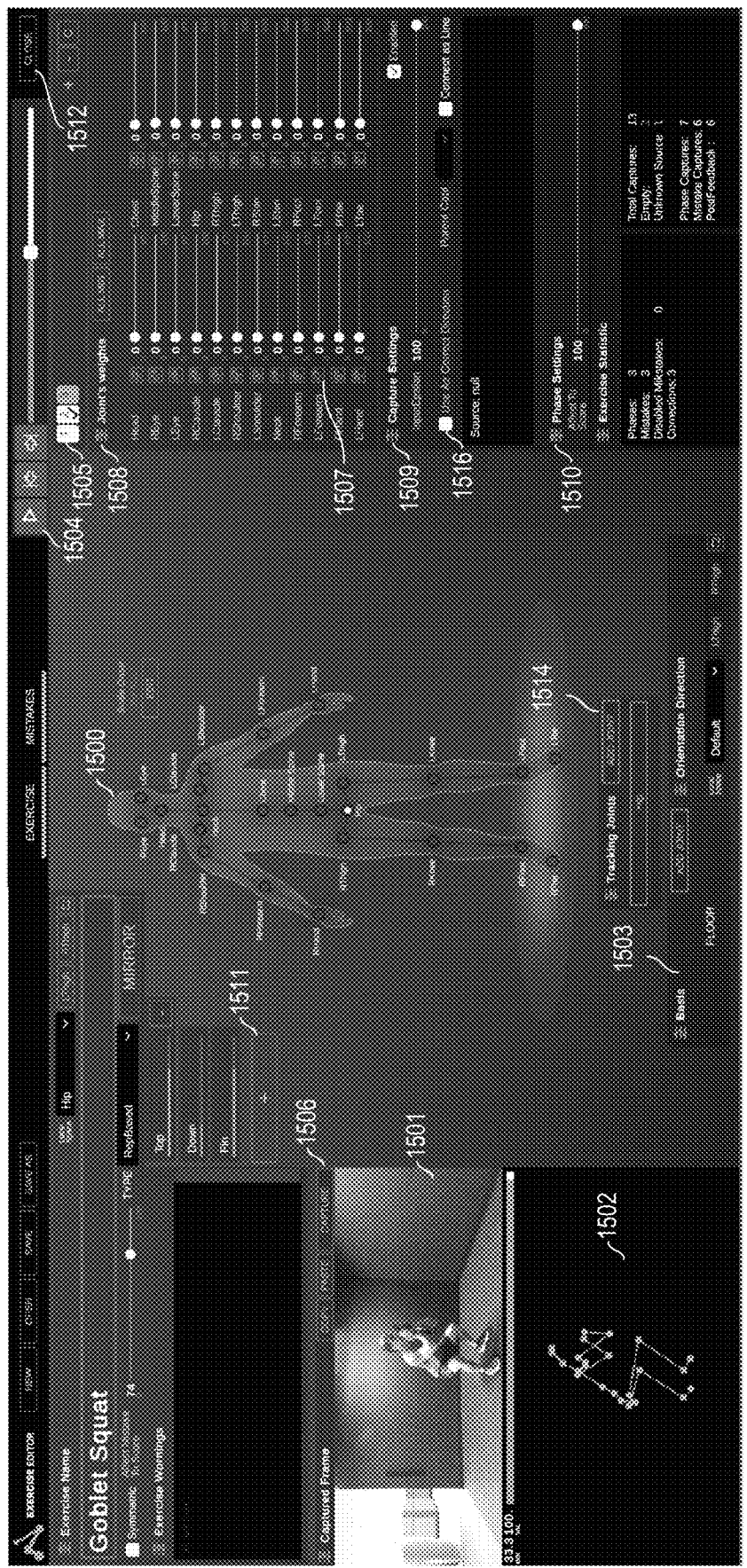
FIG. 15 illustrates a phase setting view provided by the editor system in accordance with certain embodiments.

FIG. 15 depicts a "phase setting view" provided by editor system 1206. Editor system 1206 allows an editor to define phases of an activity in association with the playback of the 3D positional data (e.g., based on captures associated with the phases). These phases may be used, e.g., to count the number of repetitions of an activity that have been performed or to compare positional data of subject 1212 with a positional data set (e.g., 3D data) of a user (e.g., 112, 1226) performing the activity in order to determine how closely the form of the user matches the form of the subject 1212. In the embodiment depicted, an editor has created three phases: "Top", "Down", and "Fin" (final) for an activity labeled "Goblet Squat." Additional phases may be added using the button 1511.

Each phase may be defined by one or more captures. Element 1505 shows that three captures are used to define a particular phase (e.g., the Down phase). Each capture may be selected in turn using element 1505 to modify settings specific to the capture. For example, such settings may include weight settings for different body parts in weights window 1508 as well as capture settings 1509.

In the phase setting view, the editor system 1206 may also display a skeleton window 1502 that includes a skeleton corresponding to the position of the subject 1212 and/or a representation of the subject in a captured frame window 1501. In various embodiments, the skeleton of the skeleton window 1502 may correspond to the skeleton 1304 of the main view (e.g., it may be shown at the same point of view and/or zoom level as skeleton 1304). Similarly, the representation of the subject in the captured frame window 1501 may correspond to the representation 1302.

The phase setting view may also provide playback controls 1504 (e.g., a play button, a rewind button, a fast forward button, and a slider) that allow the editor to move forward and backward in the playback. As the position in the playback is changed via the playback controls 1504, the position of the skeleton in window 1502 and the position of the representation of captured frame window 1501 are updated according to the subject's position at the particular time position in the playback. In various embodiments, the point of view for the captured frame window 1501 and/or skeleton window 1502 in the phase setting view may be modified by the editor within the phase setting view.

In some embodiments, the editor may be able to switch between the phase setting view and the main view (e.g., by selecting the setting button 1402 in the main view or the close button 1512 in the phase setting view). In some embodiments, when the editor switches between the phase setting view and the main view, the position (e.g., frame) of the video does not change, thus moving the playback forward or backward in the main view will correspond to an equal shift in the time position of the playback in the phase setting view. Thus, the main view and the phase setting view may be synced together in time.

In one example, the editor may create phases in the phase setting view and then switch to the main view to move the playback to the frame that the editor would like to capture and associate with a phase and then switch back to the phase setting view and make a selection (e.g., by selecting the capture button 1506 or other suitable action) to associate the capture of the phase with the position of the selected body part(s) at that frame (alternatively, the frame may be set and then the body part(s) may be selected). Alternatively, the editor may stay within the phase setting view to move the playback to the desired position for the capture.

Figure 16:
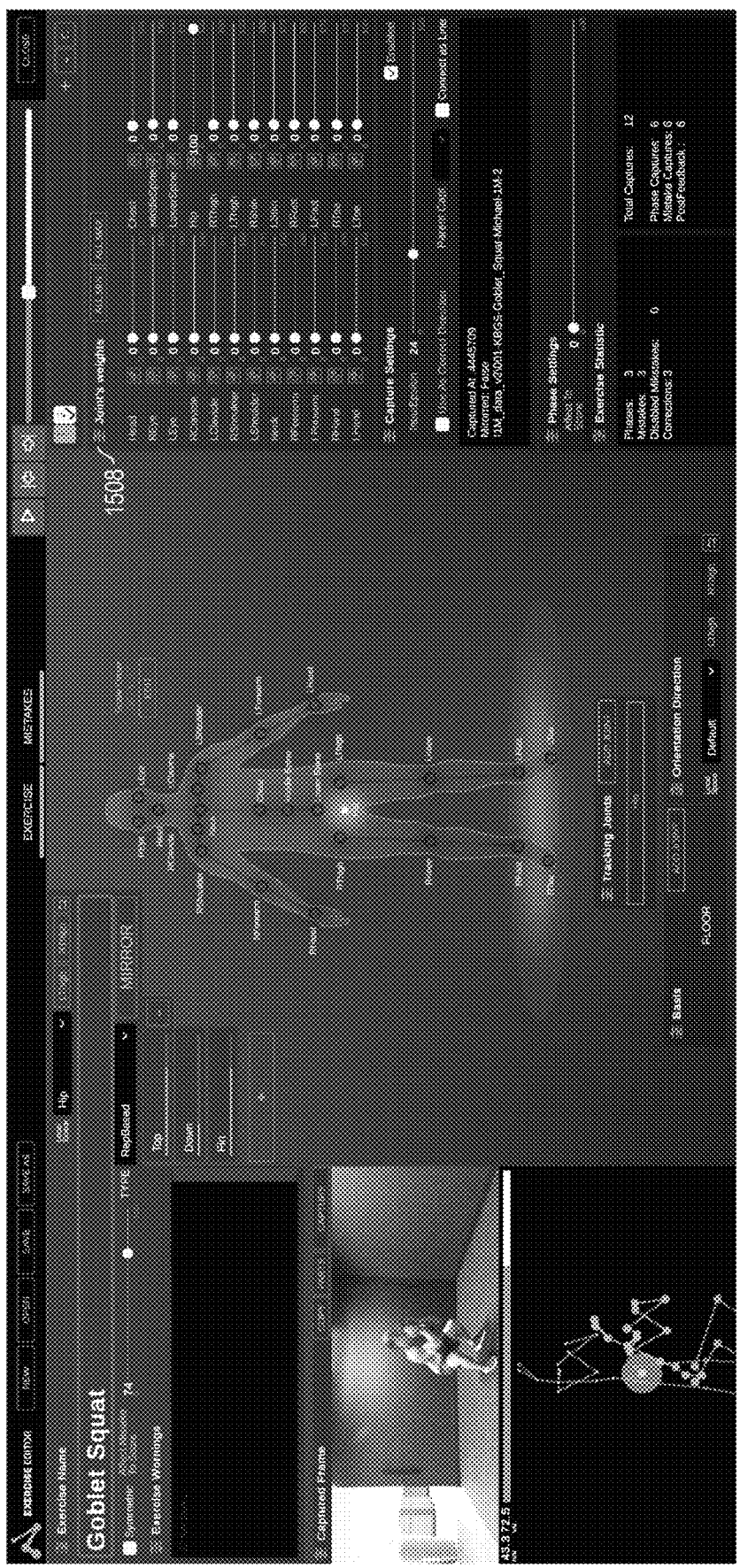
FIG. 16 illustrates a plurality of body parts and associated weights in accordance with certain embodiments.

When a frame is captured (e.g., via capture button 1506) and associated with a particular phase, the skeleton at that frame may be frozen within window 1502 (e.g., at least when that particular capture is actively selected). For example, in the embodiment depicted in FIG. 15, the editor has captured a frame and associated the capture with a phase (e.g., Down) of the Goblet Squat activity. Thus, the skeleton in window 1502 and the representation in window 1501 correspond to the lowest point of the goblet squat performed by the subject 1212. In some examples, after a frame has been captured for a particular phase, the skeleton at that frame may be persistent within the window 1502 (or the editor may be provided with an option to display or not display the skeleton) and a new skeleton associated with the current frame of the playback may also be displayed. For example, in FIG. 16, an additional skeleton is depicted in the skeleton window. In some embodiments, the skeleton window may simultaneously display the skeleton of the current frame and the skeleton of the captured frame in different colors or other formats. In some embodiments, playback of only a single skeleton is depicted during the setting of the captures of multiple phases.

A capture and/or frame may be associated with one or more segments of the subject 1212 (e.g., body parts such as a joint or other portion of the subject 1212) in any suitable manner. Although the illustrations below focus on segments comprising body parts, the teachings may be applied to any suitable segments (e.g., wearable devices). In various embodiments, the body parts to associated with the capture may be selected from a body part diagram 1500.

In the embodiment depicted, the body parts of diagram 1500 that may be associated with a capture or phase include a head, right and left eyes, right and left clavicles, right and left shoulders, neck, right and left forearms, right and left hands, chest, middle spine, lower spine, hip, right and left thighs, right and left knees, right and left feet, and right and left toes. Other embodiments may include additional, fewer, or other body parts (e.g., the body parts depicted in FIG. 11) that may be associated with a capture or phase.

The body parts may be associated with a capture or phase using one or more types of association. For example, in a first type of association, the body parts selected for association may be used to indicate that positions of the body parts should be determined for a user for comparison to corresponding positions of the subject 1212. As another example, in a second type of association, the body parts selected for association (e.g., in basis window 1503) may indicate parameters for a transformation to be applied to a representation (e.g., skeleton) of a user before comparison between positions of a user and the subject 1212 (this is described below in more detail in connection with FIG. 20). As yet another example, in a third type of association (e.g., in tracking joints window 1514), the association may provide one or more body parts to be tracked in order to facilitate synchronization between a user's movement and a subject's movement.

An editor may associate one or more body parts with a capture of a phase by selecting the phase (e.g., "Top", "Down", "Fin"), the relevant capture, and then selecting the body part(s) to be associated with the capture. In various embodiments, when one or more body parts are associated with a capture or phase of an activity by the editor, the same body part(s) may be associated automatically by the editor system 1206 with the other capture(s) or phase(s) of the activity. In other embodiments, the editor may associate one or more different body parts with the other phase(s) or capture(s). For example, the body parts may be independently selectable for each capture of each phase.

The editor system 1206 (e.g., in the phase setting view) may also provide a weights window 1508 allow the editor to set a weight for any segment (e.g., body part) that is to be associated with a capture for use in positional comparison, wherein the weight of a particular segment indicates the relative importance of that segment during positional comparison between a user and a subject. In the embodiment of FIG. 15, a weight has not yet been set for any of the body parts for the selected capture. However, in FIG. 16, a weight of 100 has been set for the hip. Accordingly, when a positional comparison is performed based on this capture, the position of the hip of the user will be compared against a target area associated with a hip of the subject as indicated by the position of the hip of the subject according to the capture (and other body parts will be ignored, at least with respect to this particular capture). As a phase may be associated with multiple captures, each other capture of the phase could include weights for one or more other body parts. When multiple body parts are associated with a capture of a phase, the body parts with higher weights may factor more heavily in determining whether the user has reached the target area indicated by the capture during performance of the activity.

Thus, in some embodiments, an editor may select one or more body parts for a capture. The capture may include positions of the selected one or more body parts at the time position corresponding to the capture. In various embodiments, an editor may also specify a weight for each body part to be used in processes utilizing the captures (e.g., counting or scoring repetitions, detecting errors, correcting errors) to indicate the relative importance of the body part (e.g., in determining whether the form of a user matches the form of at least one subject 112).

When a capture is performed at a time position (e.g., frame) of the playback, the 3D position(s) of the segment(s) (e.g., selected segments or all segments of the skeleton) at that time position may be determined and stored in association with that capture. A 3D position may be represented as an absolute position in a coordinate system or as a relative position within a range of positions (so that the data may be used for subjects or users of various shapes and sizes). These position(s) may then be used for comparison with corresponding positions based on 3D positional data of users (e.g., 112, 1226) to determine how closely the body positions of the users match the stored body positions of the activity profile in order to provide movement based feedback to the users.

A position of a body part as indicated by a capture (or positions of a body part as indicated by multiple associated captures) may be used to generate a positional boundary area for use in comparing against positions of a user. For example, during a process (e.g., repetition counting, scoring, mistake detection, or mistake correction), a determination may be made as to whether a position of a user's body part entered or did not enter the positional boundary area.

Figure 21:
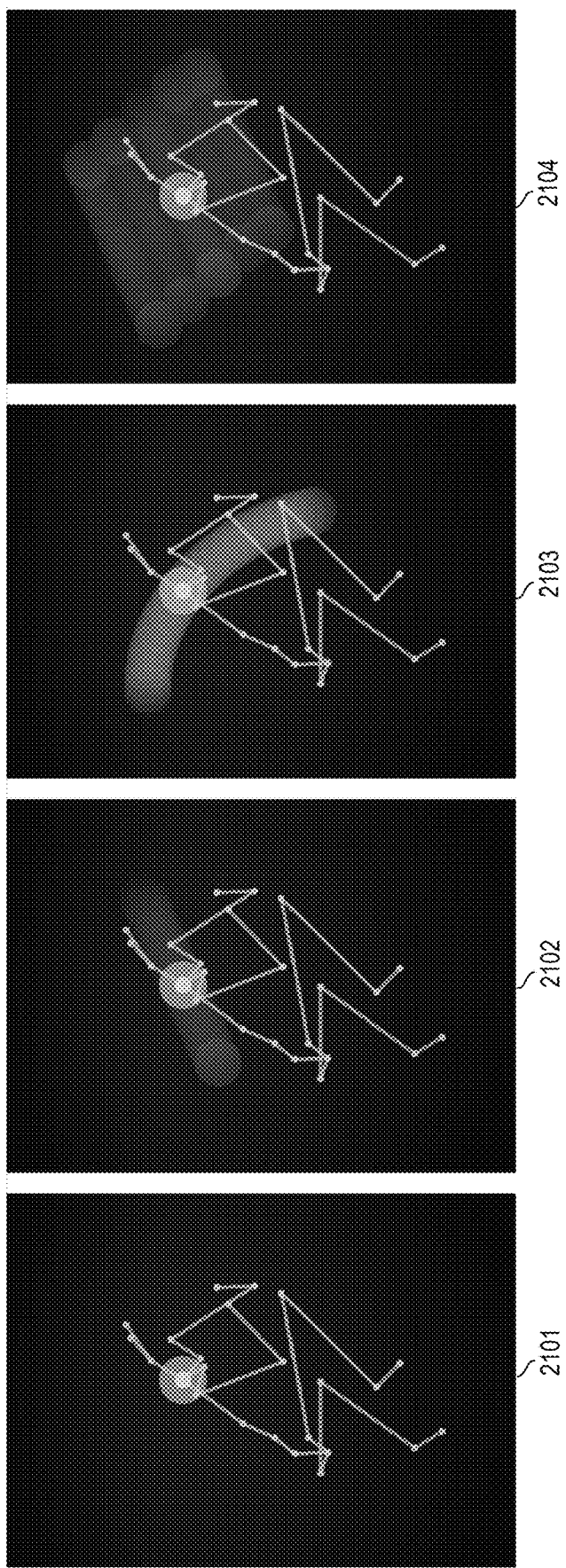
FIG. 21 illustrates example positional boundary areas based on a single capture in accordance with certain embodiments.

FIG. 21 illustrates example positional boundary areas based on a single capture. In this illustration, the positional boundary areas are based upon the position of a neck (e.g., the neck may be selected for the particular capture). In diagram 2101, the 3D position of the neck is shown in each diagram 2101-2104. In diagram 2101, the positional boundary area is shown as a sphere in which the 3D position of the neck is the center. The radius of the sphere may be configurable by the editor. Referring again to FIG. 15, the radius of the sphere may be configured, e.g., by adjusting the value of InputEpsilon (or other suitable parameter) within capture settings 1509. In some embodiments, a positional boundary area for a body part may default to a sphere, but may be changed to other suitable shape, e.g., by selecting component 1507 for a particular body part. This selection may result in display of a menu that allows an editor to manually configure the size and/or shape of the positional boundary area for the body part.

Other example positional boundary area shapes are depicted in diagrams 2102-2104. In diagram 2102, the positional boundary area represents a line of spheres (forming a shape that resembles a capsule). In diagram 2103, the positional boundary area represents an arc of spheres (forming a shape that resembles a curved capsule). In diagram 2104, the positional boundary represents a surface of spheres (effectively a series of lines of spheres).

In some embodiments, a positional boundary area may be formed based on a plurality of captures that are logically associated. For example, a first capture may be considered a parent capture and one or more other captures may be considered children captures of the parent capture. This logical grouping may allow for definition of a positional boundary area based on an interpolation between positions of different captures.

Figure 22:
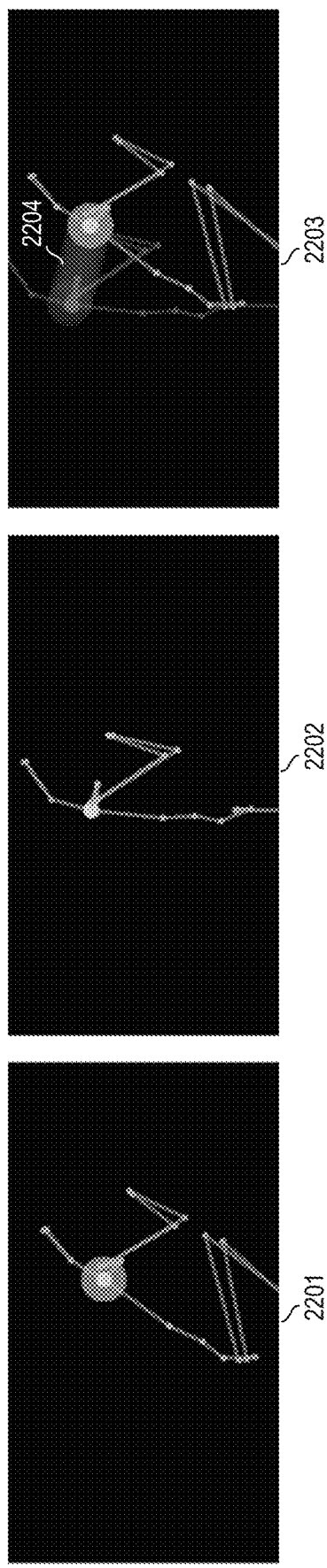
FIG. 22 illustrates merging of captures in accordance with certain embodiments.

FIG. 22 depicts a parent capture 2201 and a corresponding child capture 2202. For both captures, the selected body part is the neck. An interpolation of the parent capture 2201 and the child capture 2202 is shown in 2203. The position of the neck in the parent capture and the position of the neck in the child capture may be used as vertices of a line of spheres that defines a positional boundary area 2204.

In some embodiments, captures may be logically grouped together in a hierarchy, where a parent capture may have any number of children captures and any one or more of the children captures may be parent captures to their own one or more children captures. Lines of spheres between positions of a body part (as indicated by the various captures) may together form the positional boundary area. In other embodiments, captures may be logically grouped together and the positional boundary area may be formed that includes at least the area in between three or more positions of three or more captures (for example, positions of three or four captures could be used to create a triangular surface or a rectangular surface, in which each point inside the triangular surface or rectangular surface may be the center of a sphere and the spheres collectively define the positional boundary area).

As alluded to above, in some embodiments one or more body parts may be selected as a basis (e.g., using basis window 1503) for a comparison between one or more body parts of the subject 112 (e.g., as defined by a positional boundary area) and one or more body parts of the user. For example, one or more body parts may be selected as reference points which define the space for comparing a skeleton (or portion thereof) of the subject 1212 and a skeleton (or portion thereof) of a user (e.g., 112, 1226). In one example, if the back is the focus of an activity, the body parts selected for the basis may be hip, neck, and chest. When a motion capture and feedback system compares skeletons of a subject 1212 and a user, the position of the skeleton (or portion thereof) of the user may be translated according to one or more body parts identified in the basis selection window 1503.

Figure 20:
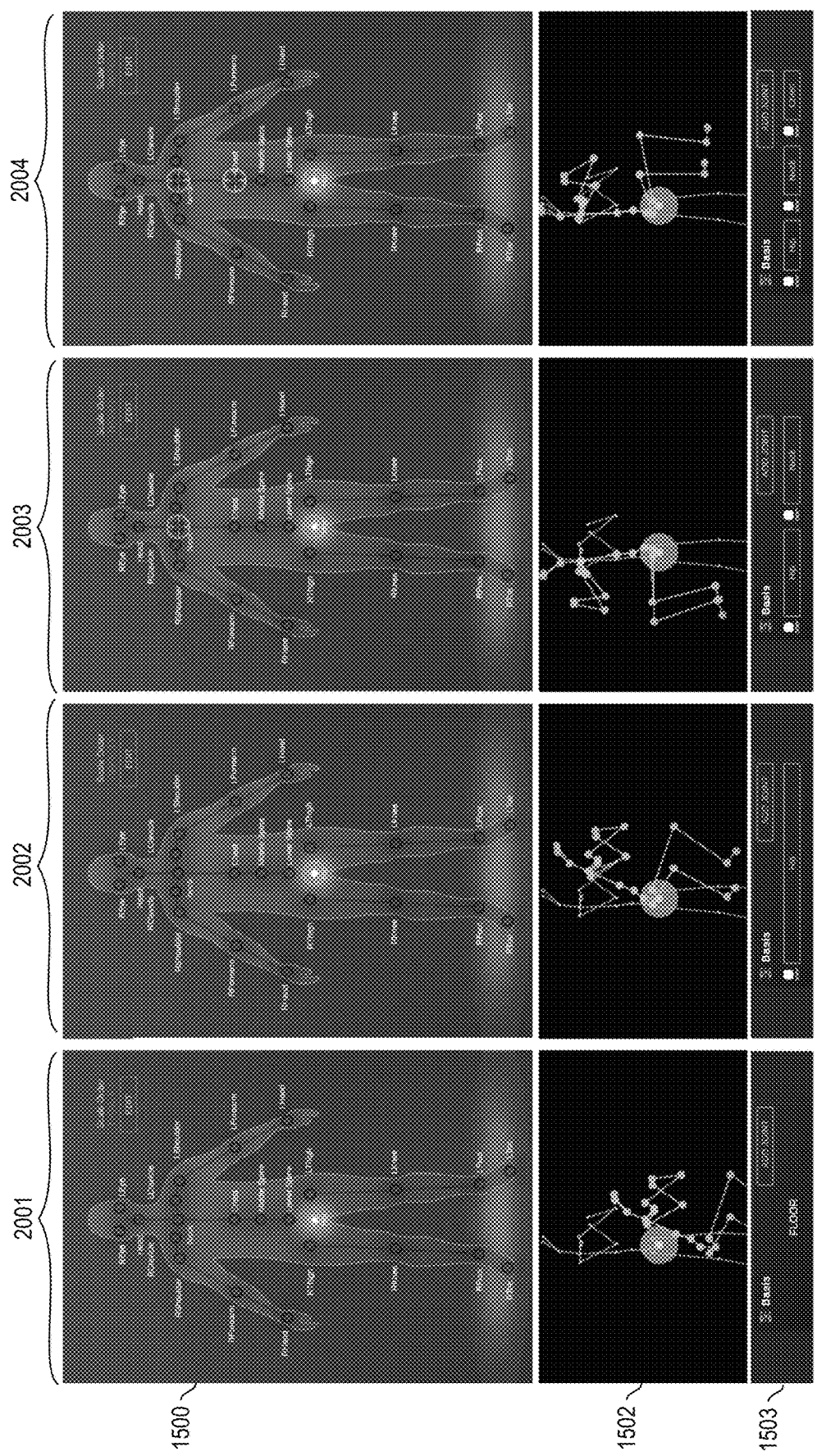
FIG. 20 illustrates an interface for skeleton alignment in accordance with certain embodiments.

FIG. 20 illustrates an interface for skeleton alignment in accordance with certain embodiments. FIG. 20 illustrates body part diagrams 1500, skeleton windows 1502, and basis windows 1503 with various different configurations 2001-2004. In configuration 2001, no body parts have been selected and thus a default basis (e.g., the floor) is used to align the two skeletons in the skeleton window 1502. In 2002, a first body part (the hip) has been added to the basis window. Consequently, the position of the first body part (hip) of the first skeleton may be translated to coincide with the position of the first body part (hip) of the second skeleton (e.g., the second skeleton may be a skeleton from a capture). In configuration 2003, the neck has been added to the basis selection 1503. The position of the first skeleton may be further translated such that the vector of the first body part (hip) to second body part (neck) vector of the first skeleton is collinear with the first body part (hip) to second body part (neck) vector of the second skeleton. In configuration 2004, a third body part (chest) is added to the basis selection 1503. This results in the rotation of the first body part (hip) to second body part (neck) vector around the directional axis coinciding with the position of the third body part (chest) in skeleton window 1502. Such translation enables the detection of back bend based on the distance between the position of the chest of subject 1212 to the chest of the user (e.g., 112, 1226) in the transformed space. Such translations may be especially useful in comparing the bend of one or more body parts between the subject and the user.

In some embodiments, the configured phases and associated captures may be utilized by the system 1200 to implement a counter that tracks the number of repetitions of the activity that have been performed. In various embodiments, the counter may be tested within the editor system 1206. For example, in FIG. 17, the counter 1702 is shown on the bottom left portion of the view and indicates that one repetition has been detected in the 3D positional data that is being played back by the editor system 1206 (which could be the same data used for the captures of the phases or different 3D positional data, e.g., which is being played back and used by the editor system 1206 to test the activity profile). The configured phases of an activity profile may also be used by motion capture and feedback systems (e.g., 102, 1220) to count repetitions of the activity performed by various users as indicated by 3D positional data captured by the respective motion capture and feedback systems.

A repetition may be detected when a determination is made that the user has passed through each phase of the activity (e.g., as defined by the captures and corresponding positions and/or positional boundary areas of the phases). For example, the counter may increment for a Goblet Squat after a determination that a user or subject has completed the Top, Down, and Fin phases. In various embodiments, a determination that a user has completed a phase may be made based on a determination that the 3D position of body parts of a user have passed constraints set by one or more captures associated with the phase. For example, if a user's body part has reached the associated positional boundary area of a capture then it may be determined that the constraints of the capture have been met. As another example, if a capture has weights for multiple body parts, a calculation may be made based on, for each of the multiple body parts, the distance between the position of the body part of the user and the ideal position defined by the capture in conjunction with the weight of the body part. For example, a weighted average of the distances from the ideal positions for the body parts may be used. The result may be compared against a threshold value for overall deviation (e.g., InputEpsilon) to determine if the constraints of the capture have been met.

Figure 17:
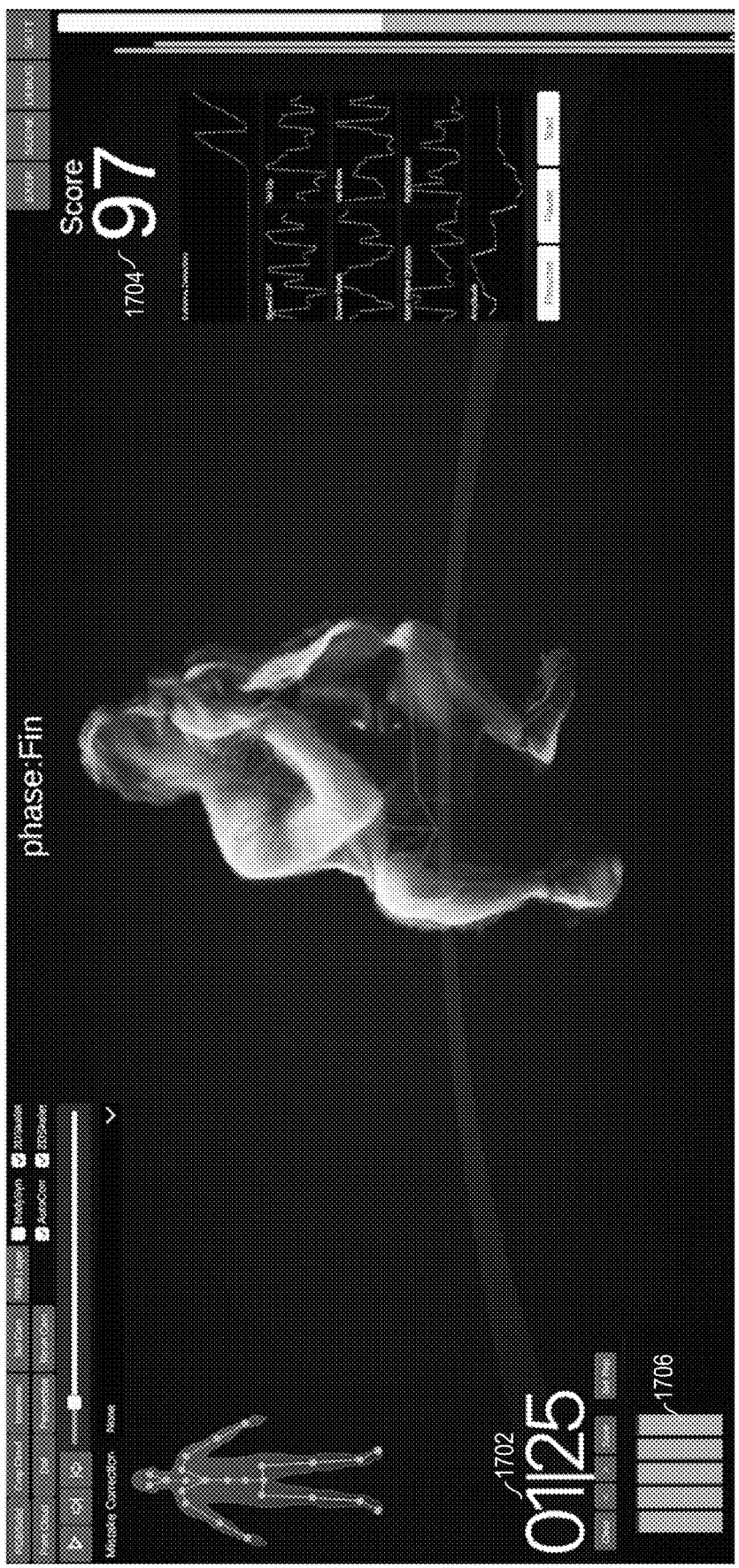
FIG. 17 illustrates a repetition counter in accordance with certain embodiments.

Similarly, the configured phases and captures may be utilized (e.g., by system 100 or 1200) to provide a score for a repetition, where the score indicates how closely the movement of the subject 1212 (e.g., when using test data) or users (e.g., 112, 1226) align with the configured phases during the repetition. In the embodiment of FIG. 17, the score 1704 of the latest repetition is shown in the upper right corner, while a bar graph representation 1706 of a history of the scores is shown in the lower left corner.

The score may be determined using any suitable techniques (e.g., linear algebra techniques, affine transformation techniques, etc.) to determine the distances between the ideal 3D positions of the selected body parts (as configured during the setting of the phases and captures as described above) versus the detected 3D positions during a repetition performed by subject 1212 (e.g., if the score is being determined during testing by the editor system 1206) or by a user (e.g., if the score is being determined by a motion capture and feedback system (e.g., 102, 1220) in order to provide feedback). In various embodiments, the score may be determined based at least in part on Euclidean distances and/or Manhattan distances between ideal 3D positions (e.g., as provided by the setting of the phases) and detected 3D positions. In some embodiments, a relative marker such as a vector from a detected body part towards the ideal 3D position may be used by itself or in conjunction with the distance between the detected body part and the ideal 3D position to determine the score.

In some embodiments, where multiple captures have been logically associated together, one of the captures may be marked (e.g., using component 1516) as the correct position. Such an embodiment may allow for a larger positional boundary area for repetition counting while still allowing for accurate reporting of the score (since the ideal 3D position will be based on the position defined by the capture which is marked as correct).

In various embodiments, the weights assigned to the body parts may also be taken into account in the scoring (thus the score will be more dependent on the distances from ideal positions for body parts that have higher weights). In some embodiments, the scores may also be affected by detection of a mistake (e.g., the score based on the distances from ideal positions may be adjusted lower responsive to a detection that a mistake was made during the repetition).

In various embodiments, the score may be based on a combination of measurements made for each capture associated with each phase (potentially excluding captures that are part of a logical combination that are not marked as having the correct form). For example, a particular phase may have multiple captures, with each capture having a weight assigned for a different body part. Thus, the positions of the various body parts of the user may be compared against the ideal positions as defined by the various captures in determining the overall score for a repetition.

In some embodiments, not all of the phases that are used to detect repetitions are used to calculate the score. Similarly, the phases may be weighted differently in calculating the score. In FIG. 15, the phase settings window 1510 includes a parameter labeled "Affect to Score" which may be used to indicate how prominently the measurements for that phase factor into the score. In the Goblet Squat example, for instance, the Down phase (where the user is descending into the squat position) may be considered more important than a phase in which the user is standing straight up and thus the Affect to Score parameter may be configured accordingly.

The exercise editor 1206 may also provide a visual encoding of one or more parameters for the activity profile (e.g., capture settings 1509 (applicable to a capture), and phase settings 1510 (applicable to the entire phase)) that may be used in performing comparisons between positional data of the subject and positional data of the users (e.g., to determine whether a phase has been reached or the score). In the embodiment depicted, these parameters are illustrated by way of example as binary checkboxes or as sliders (e.g., to indicate tolerances that may be used by transformation formulas). Such settings may include, e.g., delay, input epsilon, output epsilon, or affect to score.

Figure 18:
FIG. 18 illustrates a mistake view that may be provided by the editor system in accordance with certain embodiments.

The editor system 1206 may also be used to allow an editor to program incorrect movement patterns (mistakes) for activities. FIG. 18 depicts a "mistake view" that may be provided by the editor system 1206 in which an editor may associate one or more captures with mistake. Information associated with one or more mistakes may be programmed into an activity profile. For example, 3D positional data showing a subject 1212 performing an incorrect movement pattern may be played back by the editor system 1206 and an editor may capture time points (e.g., frames) of the 3D positional data and associate these captures with one or more mistakes. As another example, captures of 3D positional data showing a subject 1212 performing a correct movement pattern may also be associated with one or more mistakes (e.g., a mistake may be detected if the positions of one or more body parts deviates from ideal positions over a threshold amount).

The captures that are associated with a mistake may have any suitable characteristics of the captures described above with respect to captures that are associated with a phase of an activity. In addition, in some embodiments, the captures may have any other suitable attributes appropriate for use in mistake detection or mistake correction. Similarly, any suitable functionality described above for configuring a phase may be adapted for use in configuration of a mistake.

As with a phase, a mistake may be associated with one or more captures (and some of these captures could be logically connected together). In some embodiments, a capture may be classified by the editor as a detection capture or a correction capture (e.g., via component 1808). In various embodiments, different logical operations may be available (e.g., in settings window 1810) depending on whether a capture is a detection capture or a correction capture.

For example, example operations available for a detection capture may include "reached the area" (e.g., detected when one or more body parts of a user are found to be present within a positional boundary area defined by the capture), "did not reach the area" (e.g., detected when one or more body parts of a user are not found to be present within a positional boundary area defined by the capture), "left the area" (e.g., detected when one or more body parts of a user are found to be present within a positional boundary area defined by the capture but then left the positional boundary area), "did not leave the area" (e.g., detected when one or more body parts of a user are found to be present within a positional boundary area defined by the capture and did not leave the positional boundary area). The time period of a repetition over which the logical operation may perform the detection may be set according to the phases of the activity. For example, component 1806 may be used to select one or more of the phases over which the detection is to be performed. When a capture includes weights for multiple body parts, the logical operations may be more complex relative to the determinations described above (where the determination may be comparison of positions of a body part with a single positional boundary area). For example, a weighted comparison of body parts to ideal positions of body parts may be performed in conjunction with a deviation threshold (e.g., InputEpsilon) to determine if the user reached, didn't reach, never left, or left the area (for example, in a manner at least somewhat similar to that described above with respect to detection of whether a user met the constraints of a capture for a phase).

As another example, example operations available for a correction capture may include "correction for the duration of a repetition", "correction while the user is within a certain area", "correction until user reaches a certain area", "correction until user reaches a sequence of areas", other suitable operation, or combination of any of these. As with a detection for an error, a component 1812 may be used to select one or more of the phases over which the correction is to be performed.

The error and/or a detection capture of the error may also include a setting "Affect to Score" which defines how influential the error (or a particular capture associated with the error) is on the score described above.

In the embodiment depicted, a mistake labeled "Tilt Upper Spine" is being programmed for the Goblet Squat activity. In the skeleton window 1802, a first skeleton is shown squatted down and hunching over with a curved back and a second skeleton is shown standing up. One of these skeletons may correspond to the active capture (of which two captures are associated with the Tilt Upper Spine error in the embodiment depicted) which may be affected, e.g., by a selection of capture button 1804). The other skeleton may correspond to the current position of the subject in the playback.

Each capture of the mistake may also be associated with one or more body parts that may be selected in the mistake view (where the association may indicate the specific body parts that are to be considered by a motion capture and feedback system, e.g., when providing motion based instruction to determine whether the mistake was made and/or how to correct the mistake). For example, in the embodiment depicted, the active capture of the Tilt Upper Spine mistake is associated with the neck (in other embodiments, each capture could be associated with a different set of one or more body parts). In various embodiments, each body part associated with a capture may be assigned a weight specific to that capture via weights window 1906. In the embodiment depicted, the neck has been assigned a weight of 100. When the positions of the selected body parts at the particular phase are compared against corresponding positions of the same body parts of a user (e.g., 112, 1226) performing the activity, the comparison between the position of the neck of the user performing the activity and the corresponding position of the neck in the captured frame associated with the mistake may be used to determine whether the mistake has been committed. If multiple body parts are selected, the comparison may give greater relevance in the comparison to body parts having greater weights.

Figure 19:
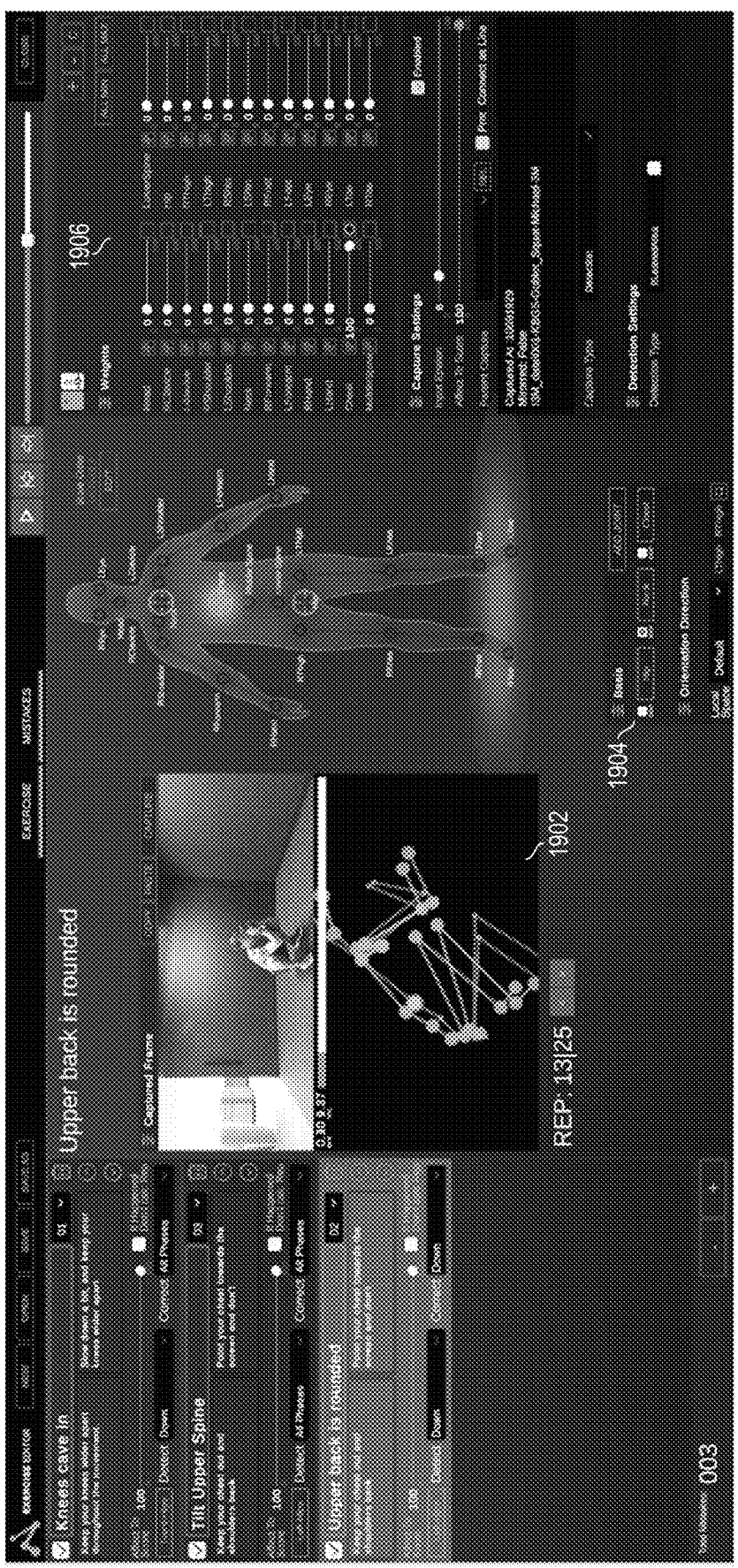
FIG. 19 illustrates another mistake view that may be provided by the editor system in accordance with certain embodiments.

FIG. 19 depicts another mistake view that may be provided by editor system 1206. In this view, multiple mistakes have been programmed for the Goblet Squat activity. These mistakes include "Knees cave in", "Tilt Upper Spine", and "Upper back is rounded." Any of these mistakes may be selected in order to modify parameters associated with the mistake. In the example depicted, "Upper back is rounded" is selected. This selection brings up a skeleton window 1902 that shows the positions of the skeletons at the time positions for the active capture and the current position of the subject in the playback. This selection also brings up a basis window 1904 which may function in a manner similar to that described above with respect to basis window 1503.

Referring again to FIG. 18, the mistake view may also provide an interface in which the editor may enter a text prompt or other media (e.g., a sound file, a video file) that is to be presented (e.g., by system 1220 to a user 1226 performing the activity) in association with a detection of the mistake. In the depicted example, the editor has entered a primary prompt of "Keep your chest out and shoulders back" and a secondary prompt of "Point your chest towards the screen and don't . . . " (the secondary prompt could be provided to the user after the primary prompt). Responsive to a determination that a user has suboptimal movement form, the system 1220 may provide instruction entered using the interface regarding how to improve the movement form. The instruction may be visual (e.g., displayed on a display, e.g., 1224) and/or auditory (e.g., played through computing device 1222 or display 1224). In various embodiments, the system 1220 may provide real time prompts to the user 1226 to assist the user in achieving proper movement form. Alternatively or additionally, device 1222 may store indications of prompts and provide the prompts at any suitable time. For example, the device 1222 may provide prompts automatically or responsive to a request from the user, e.g., after a workout set is completed, after an entire workout is completed, or prior to beginning a workout set (e.g., the prompts may be from a previous workout).

In some embodiments, the corrective feedback may be provided based on constraints associated with one or more correction captures after the mistake is detected based on one or more constraints associated with one or more detection captures (where constraints may be based, e.g., on one or more logical operators or other characteristics assigned to the captures).

The editor system 1206 may also be used to associate one or more points of view with an ideal movement or a mistake in an activity profile. For example, the editor may select a point of view and associate it with a mistake. In one example, the point of view of the skeleton within window 1802 when the frame defining the mistake is captured may be set as the point of view associated with the mistake. In other embodiments, one or more point of views may be associated with the mistake in any suitable manner (e.g., in FIG. 18, the point of view 1814 is set to left-hips). Each activity profile may include any number of possible mistakes that may each be associated with their own point of view using the editor system 1206. For example, for a first type of mistake, the point of view may be a first point of view; for a second type of mistake, the point of view may be a second point of view; and so on. In one example, if the angle of the spine is incorrect during an exercise, the point of view may be a side view of the subject, whereas if a spacing of the feet is incorrect during the exercise, the point of view may be a front or back view of the subject. In the embodiment of FIG. 19, each mistake has a point of view assigned (front-hips for knees cave in, left-hips for tilt upper spine, and left-hips for upper back is rounded).

In some implementations, responsive to a determination that a user (e.g., 112, 1226) has committed a mistake during an activity, the movement pattern of a trainer (e.g., subject 1212) may be shown by a motion capture and feedback system (e.g., 102, 1220) via a display (e.g., 116, 1224) from the point of view that has been set for the activity in the editor system 1206 in order to illustrate the correction. Additionally or alternatively, a motion capture and feedback system may provide an onscreen view of a representation of the user from the point of view associated with the mistake to highlight and correct the user's form. In some embodiments, different points of view could be set for the trainer and for the user for the mistake in the editor system 1206. The system may display the trainer or user in any suitable format (e.g., any of those described above with respect to representations 202, 1302, other representations described herein, or in other suitable formats).

Figure 23:
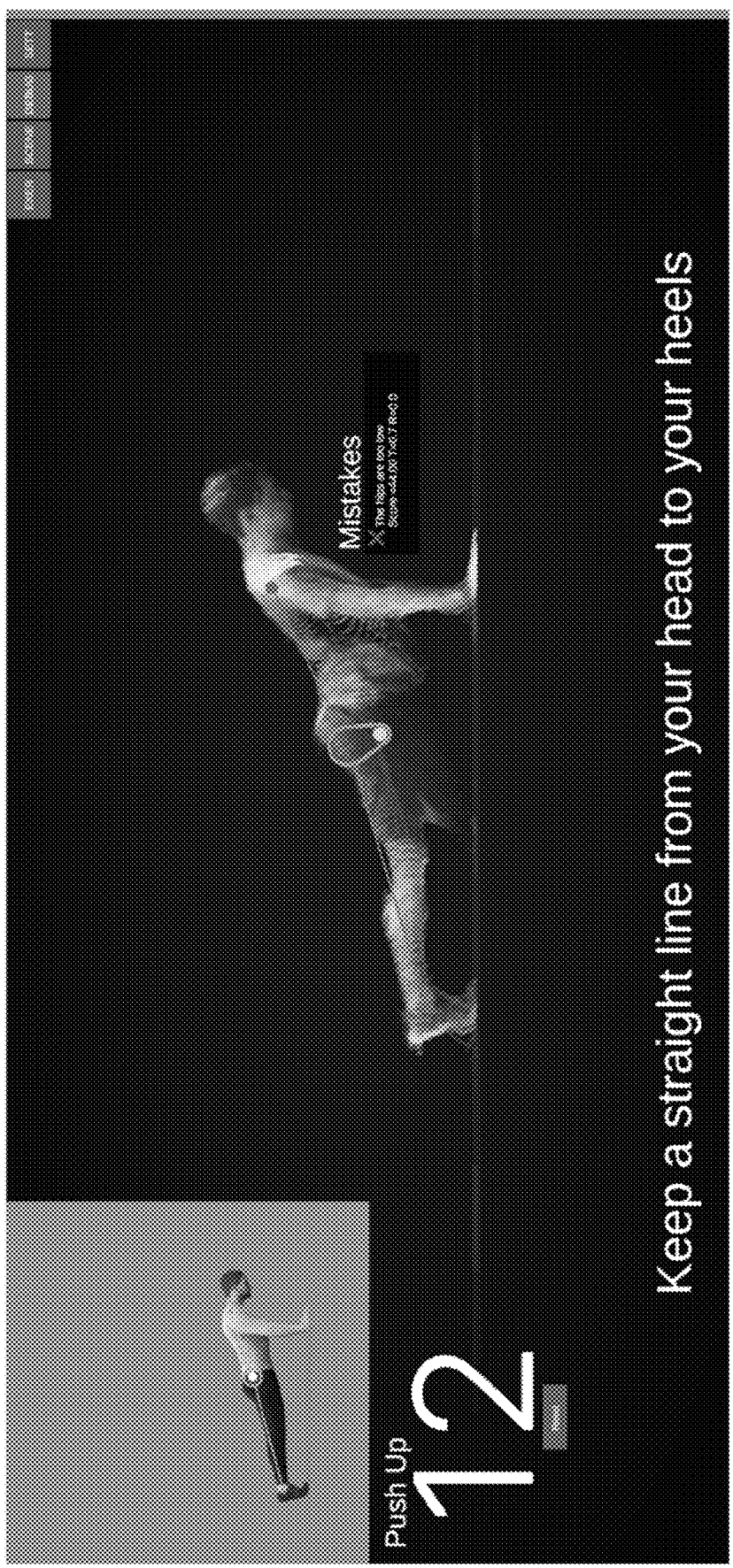
FIG. 23 illustrates correction for a push up exercise in accordance with certain embodiments.

In various embodiments, a correction capture may include a specification of one or more body parts or connections of body parts that are to be displayed in connection with a correction provided. For example, in FIG. 23, during a pushup a corrective prompt "keep a straight line from your head to your heels is shown" along with an emphasis on a body part (hip) that is too low. Thus, the associated correction capture may specify that the hip should be shown to the user. This specification of one or more body parts may apply to a model trainer displayed and/or the representation of the user (both are depicted in FIG. 23).

In one embodiment, when a user begins an activity, a motion capture and feedback system may display the user from a default point of view associated with the activity (where different activities may have different default points of view and the default points of view may be specified, e.g., in the activity profiles). The motion capture and feedback system may then change the point of view for the representation of the user based on the point of view set for a mistake in the activity profile responsive to a determination that the user has committed a mistake (assuming that the point of view set in the profile is different from the default point of view).

In some embodiments, a mistake may be associated in an activity profile with more than one point of view using the editor system 1206. For example, a first point of view may be associated with a first instance of a mistake and a second point of view may be associated with a second instance of a mistake. In such an embodiment, the first time a mistake of a user is detected (e.g., by system 1220), the first point of view associated with the mistake is used while the second time the mistake is detected, the second point of view associated with the mistake is used (or the second point of view may be used at any other suitable time, such as the third time a mistake is committed, etc.).

In various embodiments, editor system 1206 may also allow an editor to specify conditions in an activity profile defining system operation when multiple mistakes are detected. For example, the editor could rank the mistakes (e.g., based on safety concerns) such that the highest ranked mistake is communicated by a motion capture and feedback system to a user if the system detects that the user committed multiple mistakes during one or more repetitions of the activity. In another embodiment, the editor may specify that the mistake with the highest deviation from the ideal form is to be communicated to the user 1226. In some embodiments, the editor may specify that multiple mistakes may be simultaneously communicated to the user 1226. The editor could alternatively specify that multiple mistakes should be communicated in succession.

In various embodiments, editor system 1206 may allow an editor to copy parameters for one or more mistakes to one or more other mistakes of the same activity or a different activity. For example, the body parts and weights assigned to one mistake may be copied over to another mistake. As another example, the phase settings (e.g., as defined by 1806, 1812) assigned to one mistake may be copied over to another mistake. In some embodiments, the editor system 1206 may allow an editor to select a mistake and/or certain parameters for the mistake to copy and to enter the other mistakes to which the parameters should be copied. Once copied, these parameters can be modified by the editor if desired. In some embodiments, the editor system 1206 may allow an editor to build libraries of mistakes.

Once one or more mistakes have been defined for an activity, various instances of the activity may be previewed within editor system 1206 to allow the editor to see the application of the mistakes to 3D positional data input (e.g., of the subject 1212) in order to test the configuration of the activity profile.

As described above, an activity profile generated by the editor system 1206 (and provided to a system 1220 for use in movement based instruction) for an activity may include one or more parameters derived from an editor's interaction with the editor system 1206. For example, the parameters may include any one or more of the following (or any of the other information described above with respect to the features of the editor system 1206 or other information utilized by a motion and capture feedback system to provide feedback with respect to an activity): 3D positions for one or more selected segments of a subject at specified phases of an ideal movement pattern for an activity, 3D positions for one or more selected segments of a subject for one or more captures associated with mistakes, weights for the selected segments, parameters associated with captures to be used in determining whether a mistake has been committed by a user 1226, optimized points of view for correction of the one or more mistakes, and corrective prompts for the one or more mistakes. In various embodiments, an activity profile may include at least a portion of any suitable information that may form the basis for any of the feedback provided by a motion capture and feedback system described herein. Similarly, in various embodiments, any of the motion capture and feedback systems described herein may provide feedback to a user based on any of the capabilities of the editor system 1206 described herein (even if such capabilities are not explicitly described as being provided for use by the motion capture and feedback system).

As alluded to above, in various embodiments of the present disclosure, a system may provide velocity based dynamic workout adjustments. The description below will reference velocity based dynamic workout adjustments performed by system 100, although the functionality may be implemented by any suitable system, such as systems and/or devices 100, 102, 104, 118, 1200, 1204, 1206, 1220, combinations of these, or other suitable computing system or collection of logic). Human central nervous system output (e.g., force conducted through the musculoskeletal system) is affected significantly by readiness, where readiness may be affected by numerous physical and psychological factors such as sleep and stress. Velocity (change in position distance over time) can be used to determine an individual's readiness (e.g., moment-to-moment ability to exert force) as measured in velocity (of an object being moved by the individual or of one or more body parts of the individual).

Velocity measurements may inform (1) how much of an exercise an individual should perform (e.g., the number of sets and repetitions) and (2) the weight (also referred to as load) to be used during a specific exercise.

An example exercise for which velocity measurements may be taken to determine an individual's readiness is a vertical jump (where a vertical jump height is a measure of an individual's ability to displace the individual's body from a start position with maximal force, in which both mass and gravity are constant). In order to use the vertical jump as an indicator of readiness, a baseline average jump height is first established. An individual's readiness (e.g., the ability of the central nervous system of the individual to produce force) may be measured by comparing a vertical jump height (where the vertical jump height is correlated with the body's upward velocity during the jump) against the average vertical jump height prior to an exercise training session. A good night's sleep would correlate with greater velocities and heights, while poor sleep would correlate with lower velocities and heights.

Velocity measurements may also be used to modulate, in real time, one or both of the volume (sets×repetitions) and load (e.g., weight) in an exercise training session. Velocity based training may be used in barbell lifts, such as in weightlifting (e.g., clean and jerk, snatch) and powerlifting (e.g., bench press, squat, and deadlift). Traditionally, training in these barbell lifts used a single-factor equation of how much weight was used in these lifts and ignored the velocity at which the lift was performed. To determine the loads used in training (which are typically submaximal loads), a one rep maximum (1 RM) representing how much load an individual can maximally lift in a single all-out effort would first be established. By way of example, if an individual squatted 200 lbs. in a single all-out effort, that individual's 1 RM would be 200 lbs. A breakdown of submaximal weights could then be calculated using percentages of the 1 RM. For example:

|  | LBS |
| --- | --- |
| 1RM | 200 |
| 95% | 190 |
| 90% | 180 |
| 85% | 170 |
| 80% | 160 |
| 75% | 150 |
| 70% | 140 |
| 65% | 130 |
| 60% | 120 |
| 55% | 110 |
| 50% | 100 |

These percentages (also referred to as "intensities") convey much information informing, e.g., how many reps or sets to perform, when and how frequently in a training cycle they should be used, and what adaptation (e.g., muscle size, endurance, strength, etc.) will likely be stimulated in an individual. The intensities determined according to the methods of the instant disclosure can further be used in a variety of ways.

For example, an estimation may be used to determine the number of repetitions possible at one of these submaximal intensities, as depicted in the following chart:

|  | LBS | Est. Maximum Reps |
| --- | --- | --- |
| 1RM | 200 | 1 |
| 95% | 190 | 3 |
| 90% | 180 | 5 |
| 85% | 170 | 6 |
| 80% | 160 | 8 |
| 75% | 150 | 10 |
| 70% | 140 | 12 |
| 65% | 130 | 15 |
| 60% | 120 | 20 |
| 55% | 110 | 20+ |
| 50% | 100 | 20+ |

The 1 RM value shown in the chart may be estimated using a submaximal load. For example, if an individual was able to maximally squat 10 repetitions at 150 lbs., an assumption may be made that 150 lbs. is 75% of the 1 RM, thus the 1 RM is estimated to be 200 lbs. While this chart is only an estimate (as a variety of variables are involved, such as skill level), it provides a useful model for creating an exercise training regimen.

Relying on the relationship between velocity and readiness, velocity's influence on this model may be ascertained. As readiness improves or regresses, an individual's 1 RM may fluctuate. This fluctuation affects all submaximal loading in the exercise training regimen for the individual. Thus, velocity is a valuable tool that may be used in conjunction with the load in prescribing an exercise routine.

This may be illustrated using the chart below in which a new column for velocity is added to the previous 1 RM chart:

|  | LBS | Maximum Reps | Velocity (meters/second) |
| --- | --- | --- | --- |
| 1RM | 200 | 1 | .10 m/s |
| 95% | 190 | 3 | .20 m/s |
| 90% | 180 | 5 | .25 m/s |
| 85% | 170 | 6 | .30 m/s |
| 80% | 160 | 8 | .40 m/s |
| 75% | 150 | 10 | .45 m/s |
| 70% | 140 | 12 | .50 m/s |
| 65% | 130 | 15 | .60 m/s |
| 60% | 120 | 20 | .70 m/s |
| 55% | 110 | 20+ | .75 m/s |
| 50% | 100 | 20+ | .80 m/s |

Using the above model, if an exercise program of a user 112 called for a set of 5 squats at 165 lbs. (80-85%), but the user 112 performed the squats at only 0.20 m/s, then the system (e.g., 100, 102, 1200, 1220) may determine that the readiness of the user is likely lower than normal and therefore the user's 1 RM is no longer 200 lbs. (as 0.20 m/s is the expected velocity for a much higher intensity (e.g., at 95%, not 80-85%). System 100 may therefore modulate the exercise program for the user for the day based on the velocity value. As an example, the system 100 could adjust the load for the repetitions based on the following exemplary chart as may be measured for a user 112 in a particular workout instance:

|      | LBS | Maximum Reps | Velocity (meters/second) |
| ---- | --- | ------------ | ------------------------ |
| 1RM  | 174 | 1            | N/A                      |
| 95%  | 165 | 3            | .20 m/s                  |
| 90%  | 157 | 5            | .25 m/s                  |
| 85%  | 148 | 6            | .30 m/s                  |
| 80%  | 139 | 8            | .40 m/s                  |
| 75%  | 131 | 10           | .45 m/s                  |
| 70%  | 122 | 12           | .50 m/s                  |
| 65%  | 113 | 15           | .60 m/s                  |
| 60%  | 104 | 20           | .70 m/s                  |
| 55%  | 96  | 20+          | .75 m/s                  |
| 50%  | 87  | 20+          | .80 m/s                  |

The user may then proceed with squat sets at a new prescribed load of 140-145 lbs.

In various embodiments, system 100 expands velocity based training to exercises outside of the traditional lifts (e.g., clean and jerk, snatch, bench press, squat, and deadlift) to any suitable exercises with or without weights. In some embodiments, system 100 may utilize devices 114 to capture video of the user 112 and computing device 118 (or other computing device(s)) to calculate velocities of one or more body parts (e.g., any of those described above, other joints or body segments, etc.) of user 112 over one or more phases or other portions of a repetition of an activity and then use the calculated velocities to dynamically adjust the workout of the user 112.

Accordingly, system 100 may provide real time velocity monitoring of any suitable activity (e.g., in conjunction with computer vision and an expert recommendation system) to generate workouts personally tailored to an individual in real time. The workouts may be customized at various levels of granularity. For example, the system 100 may use the velocity feedback to adjust, e.g., an overall workout regime, a particular workout schedule for a day, multiple sets of a particular activity, or even an individual set of one activity. The adjustments could include adjustments to one or more loads and/or repetitions to be performed for one or more activities.

System 100 may generate an individual workout plan and schedule specific workouts for a user 112 (e.g., based on any suitable information contained in a profile of a user and/or based on other suitable information described herein). Because system 100 is able to detect the user's skeleton in real time, it is capable of detecting velocity of movement in the key joints or other body segments of the body for specific exercises. These velocity indicators may be utilized to determine the level of the user's fatigue and readiness. Depending on these readings, system 100 may automatically adjust a current workout and use a velocity history to adjust user workouts in real time.

The following tables list example velocities of a joint or other body part and corresponding possible reps. The velocities may be indicative of a level of fatigue of the user.

|                 | % RM   | Avg m/s   | Reps per set possible |
| --------------- | ------ | --------- | --------------------- |
| Goblet Squat    |        |           |                       |
| Easy (1)        | 0-20   | 1.16-.99  | 48+                   |
| Moderate (2)    | 20-40  | .99-.82   | 36-48                 |
| Challenging (3) | 40-60  | .82-.65   | 24-36                 |
| Hard (4)        | 60-80  | .65-.47   | 12-24                 |
| Very Hard (5)   | 80-100 | .47-.31   | 1-12                  |

|                       | % RM   | Avg m/s    | Reps per set possible |
| --------------------- | ------ | ---------- | --------------------- |
| Single DB Closed Chain Row |   |            |                       |
| Easy (1)              | 0-20   | 1.83-1.64  | 48+                   |
| Moderate (2)          | 20-40  | 1.64-1.44  | 36-48                 |
| Challenging (3)       | 40-60  | 1.44-1.24  | 24-36                 |
| Hard (4)              | 60-80  | 1.24-1.04  | 12-24                 |
| Very Hard (5)         | 80-100 | 1.04-.84   | 1-12                  |

When the system 100 measures an average velocity in one or more key body parts (e.g., knee joints, hip joints, elbow joints, shoulder joints, ankle joints, etc.) in a certain range during one or more repetitions of an activity (where the joints that are measured may be specific to the activity being performed), it may adjust a workout for the user to change the number of reps and/or the load in the next set (or multiple future sets). For example, if system 100 detects an average m/s reading of 0.4 for a set of goblet squats, system 100 may adjust the workout and instruct the user to perform fewer reps in the next set or to lower the weight used in the next set. As another example, if the average m/s reading is 1.2, the system 100 may instruct the user to perform additional reps and increased weight.

In addition or as an alternative to velocity measurements, system 100 (or other systems and/or devices described herein) may use any suitable collection of information to customize workout plans for user 112. For example, system 100 may utilize physical attributes of the user (e.g., age, height, weight, sex, diet, availability for workouts). As another example, system 100 may utilize previous workout performances (e.g., activities, velocities, repetitions, loads used, etc.). As another example, system 100 may utilize a fitness goal (e.g., lose weight, increase endurance, increase strength, build muscle, improve 1 RM, etc.). As another example, system 100 may utilize the order of the workout to adjust parameters for individual exercises (e.g., more sets, repetitions, or increased load may be used for a particular exercise if it is placed at the beginning of a workout as opposed to later in the workout when the user is expected to be fatigued). Any suitable parameters may be provided (e.g., to a machine learning model or other logic of the system) to generate the workout plans for the user. In various embodiments, any of the above characteristics (or other suitable information associated with a user), such as user attributes, fitness goals, workout history, or planned workouts may be stored in a profile of the user as a set of parameters.

Figure 24:
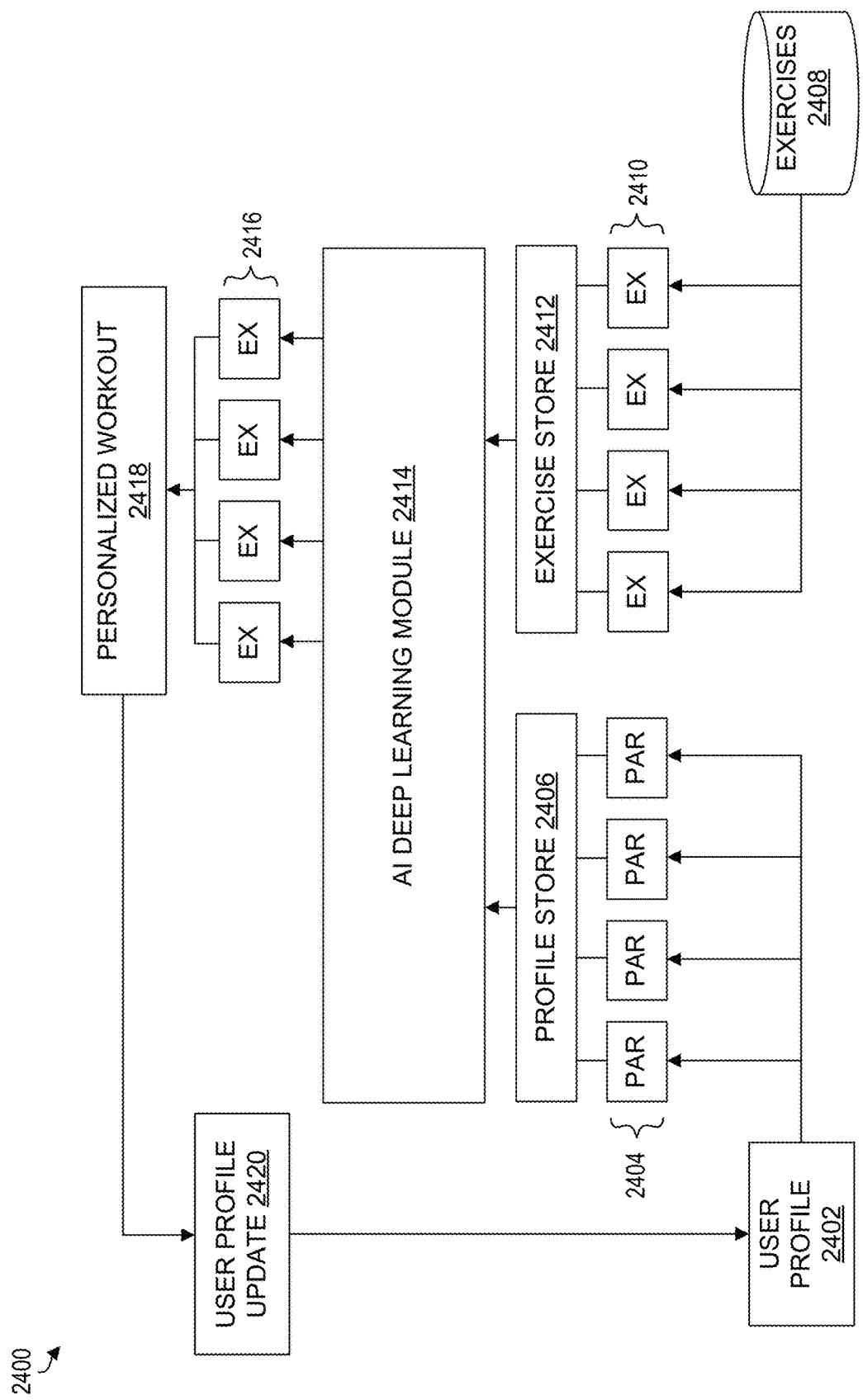
FIG. 24 illustrates a system to generate a personalized workout in accordance with certain embodiments.

FIG. 24 illustrates a system 2400 for generating a personalized workout 2418. System 2400 may be a part of any of the other systems or devices described herein (or may be implemented using any suitable computing system). The system utilizes a user profile 2402 including various parameters associated with a user. At least some of the parameters 2404 may be stored in profile store 2406 in a format that is usable by the AI deep learning module 2414.

System 2400 may also include or be in communication with a database of exercises 2408 and at least some of these exercises 2410 may be stored in exercise store 2412 in a format usable by the AI deep learning module 2414.

A machine learning module (e.g., AI deep learning module 2414) may select a plurality of personalized exercises 2416 for a user to form a personalized workout 2418 based on the parameters 2404. In one embodiment, module 2414 may implement an autoregressive model in which, during the first iteration, the module 2414 predicts a first exercise based solely on the parameters 2404 of the user profile 2402. This selected exercise may then be added as one of the parameters of the user profile 2402 by the user profile update module 2420. The module 2414 may then select an additional exercise based on the updated user profile 2402 (with the first selected exercise also used as an input parameter). The additional exercise may become part of the user profile 2402 in like manner and is also provided as input to the module 2414 to select a third exercise, and so on, until a complete workout is generated. In future iterations of personalized workout generation, one or more past workouts with their constituent exercises may be provided as parameters to the module 2414 as inputs for exercise selection.

Any of the components of FIG. 24 may be implemented by any of the components of a computing system, such as 100 or 1200, or other suitable logic. For example, the AI deep learning module 2414 may be implemented by computing device 118, backend system 104, other component of system 100, or a combination of these.

In various embodiments, system 100 may collect workout data from many different users 112. For example, system 102 may sense or otherwise collect workout data from multiple users and/or system 100 may include many geographically dispersed motion capture and feedback systems 102 that are each operable to record workout data from one or more users 112. The workout data may be stored, e.g., by backend system 104.

The stored workout data may include data derived from image data (e.g., point cloud information) detected by devices 114 (e.g., translations into a user's skeleton in 3D space, velocities of key joints or other user body portions). This data may be stored in the backend system 104 and may be used to assess the progress of various users and make recommendations based thereon. In one embodiment, parameters derived from such information may be provided to the module 2414 for use in workout selection.

In some embodiments, backend system 104 or other computing system or device may utilize a machine learning algorithm to use the data to give optimal advice as to how a particular user can reach a fitness goal (e.g., losing weight, improving a one rep maximum for a particular exercise, etc.). The machine learning algorithm may assess thousands of sessions over time to determine a workout schedule for a user 112 with a given set of attributes to achieve the fitness goal within a specified interval. For example, system 100 may recommend a workout frequency and specific exercises and intensities for the user 112 to perform to promote the likelihood that the user 112 will achieve the fitness goal. As another example, system 100 may use other information, such as the number and/or length of workouts performed by the user over a time period (e.g., a month) or a number and/or length of workouts expected to be performed by the user to tailor the workout plan for the user based on the user's goals (e.g., system 100 may suggest a different workout if the user plans to exercise daily as opposed to only once or twice per week). As just one example, if a user plans to exercise daily, the generated workouts may alternate muscle groups daily whereas if the user plans to exercise once per week, the workouts may target a larger range of muscle groups.

In various embodiments, a system implementing a machine learning algorithm may be trained on data (e.g., planned workouts) provided by human experts (e.g., through expert network system 108) for particular individuals (which may or may not be users 112) along with any suitable data of profiles of the individuals (such as any of the profile data described herein). Thus, the system may generate personalized workouts for a particular user 112 based on workouts generated by human experts for other individuals based on similarities and/or differences between profile parameters of the individuals and profile parameters of the user 112.

"Logic" as used herein, may include but not be limited to hardware, firmware, software and/or combinations of each to perform a function(s) or an action(s), and/or to cause a function or action from another logic, method, and/or system. In various embodiments, logic may include a software controlled microprocessor, discrete logic (e.g., an application specific integrated circuit (ASIC)), a programmed logic device (e.g., a field programmable gate array (FPGA)), a memory device containing instructions, combinations of logic devices, or the like. Logic may include one or more gates, combinations of gates, or other circuit components. Logic may also be fully embodied as software.

While the present disclosure has been described with respect to a limited number of embodiments, those skilled in the art will appreciate numerous modifications and variations therefrom. It is intended that the appended claims cover all such modifications and variations as fall within the true spirit and scope of this present disclosure. Although this disclosure has been described in terms of certain implementations and generally associated methods, alterations and permutations of these implementations and methods will be apparent to those skilled in the art. For example, the actions described herein can be performed in a different order than as described and still achieve the desirable results. As one example, the processes depicted in the accompanying figures do not necessarily require the particular order shown, or sequential order, to achieve the desired results. In certain implementations, multitasking and parallel processing may be advantageous. Other variations are within the scope of the following claims.

The architectures presented herein are provided by way of example only, and are intended to be non-exclusive and non-limiting. Furthermore, the various parts disclosed are intended to be logical divisions only, and need not necessarily represent physically separate hardware and/or software components. Certain computing systems may provide memory elements in a single physical memory device, and in other cases, memory elements may be functionally distributed across many physical devices. In the case of virtual machine managers or hypervisors, all or part of a function may be provided in the form of software or firmware running over a virtualization layer to provide the disclosed logical function.

Note that with the examples provided herein, interaction may be described in terms of a single computing system. However, this has been done for purposes of clarity and example only. In certain cases, it may be easier to describe one or more of the functionalities of a given set of flows by only referencing a single computing system. Moreover, the system for deep learning and malware detection is readily scalable and can be implemented across a large number of components (e.g., multiple computing systems), as well as more complicated/sophisticated arrangements and configurations. Accordingly, the examples provided should not limit the scope or inhibit the broad teachings of the computing system as potentially applied to a myriad of other architectures.

As used herein, unless expressly stated to the contrary, use of the phrase 'at least one of' refers to any combination of the named items, elements, conditions, or activities. For example, 'at least one of X, Y, and Z' is intended to mean any of the following: 1) at least one X, but not Y and not Z; 2) at least one Y, but not X and not Z; 3) at least one Z, but not X and not Y; 4) at least one X and at least one Y, but not Z;

5) at least one X and at least one Z, but not Y; 6) at least one Y and at least one Z, but not X; or 7) at least one X, at least one Y, and at least one Z.

Additionally, unless expressly stated to the contrary, the terms 'first', 'second', 'third', etc., are intended to distinguish the particular nouns (e.g., element, condition, module, activity, operation, claim element, etc.) they modify, but are not intended to indicate any type of order, rank, importance, temporal sequence, or hierarchy of the modified noun. For example, 'first X' and 'second X' are intended to designate two separate X elements that are not necessarily limited by any order, rank, importance, temporal sequence, or hierarchy of the two elements.

References in the specification to "one embodiment," "an embodiment," "some embodiments," etc., indicate that the embodiment(s) described may include a particular feature, structure, or characteristic, but every embodiment may or may not necessarily include that particular feature, structure, or characteristic. Moreover, such phrases are not necessarily referring to the same embodiment.

While this specification contains many specific implementation details, these should not be construed as limitations on the scope of any embodiments or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, the separation of various system components and modules in the embodiments described above should not be understood as requiring such separation in all embodiments. It should be understood that the described program components, modules, and systems can generally be integrated together in a single software product or packaged into multiple software products.

Use of the phrase 'configured to,' in one embodiment, refers to arranging, putting together, manufacturing, offering to sell, importing and/or designing an apparatus, hardware, logic, or element to perform a designated or determined task. In this example, an apparatus or element thereof that is not operating is still 'configured to' perform a designated task if it is designed, coupled, and/or interconnected to perform said designated task. Note once again that use of the term 'configured to' does not require operation, but instead focus on the latent state of an apparatus, hardware, and/or element, where in the latent state the apparatus, hardware, and/or element is designed to perform a particular task when the apparatus, hardware, and/or element is operating.

Furthermore, use of the phrases 'to,' 'capable of/to,' and or 'operable to,' in one embodiment, refers to some apparatus, logic, hardware, and/or element designed in such a way to enable use of the apparatus, logic, hardware, and/or element in a specified manner. Note as above that use of to, capable to, or operable to, in one embodiment, refers to the latent state of an apparatus, logic, hardware, and/or element, where the apparatus, logic, hardware, and/or element is not operating but is designed in such a manner to enable use of an apparatus in a specified manner.

The embodiments of methods, hardware, software, firmware or code set forth above may be implemented via instructions or code stored on a machine-accessible, machine readable, computer accessible, or computer readable medium which are executable by a processing element. A machine-accessible/readable medium includes any mechanism that provides (e.g., stores and/or transmits) information in a form readable by a machine, such as a computer or electronic system. For example, a non-transitory machine-accessible medium includes random-access memory (RAM), such as static RAM (SRAM) or dynamic RAM (DRAM); ROM; magnetic or optical storage medium; flash memory devices; electrical storage devices; optical storage devices; acoustical storage devices; other form of storage devices for holding information received from transitory (propagated) signals (e.g., carrier waves, infrared signals, digital signals); etc., which are to be distinguished from the non-transitory mediums that may receive information there from.

Instructions used to program logic to perform embodiments of the invention may be stored within a memory in the system, such as DRAM, cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magneto-optical disks, Read-Only Memory (ROMs), Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the computer-readable medium includes any type of tangible machine-readable medium suitable for storing or transmitting electronic instructions or information in a form readable by a machine (e.g., a computer).

Numerous other changes, substitutions, variations, alterations, and modifications may be ascertained to one skilled in the art and it is intended that the present disclosure encompass all such changes, substitutions, variations, alterations, and modifications as falling within the scope of the appended claims.

Example 1 includes a method, comprising generating, for display to a user, a representation of the user performing a movement pattern of an activity from a first point of view; sensing a deviation of movement of the user from a model movement pattern for the activity; selecting a second point of view based on a type of the deviation; and generating, for display to the user, a representation of the user performing the movement pattern for the activity from the second point of view.

Example 2 includes the subject matter of Example 1, and further including providing, for display to the user, a representation of a trainer performing an example movement pattern of the activity from the first point of view; and providing, for display to the user, a representation of the trainer performing the example movement pattern of the activity from the second point of view responsive to sensing the deviation of the user from the model movement pattern.

Example 3 includes the subject matter of any of Examples 1 and 2, and further including generating a guide skeleton to be overlaid on the representation of the user.

Example 4 includes the subject matter of any of Examples 1-3, and further including changing a color or brightness of a segment of the guide skeleton responsive to alignment of a body segment of the user with the segment of the guide skeleton.

Example 5 includes the subject matter of any of Examples 1-4, and further including causing display of the guide skeleton responsive to a determination that the user is near a target position associated with the deviation.

Example 6 includes the subject matter of any of Examples 1-5, and wherein the representation of the user performing the movement pattern from the first point of view and the representation of the user performing the movement pattern from the second point of view is based on video data captured by image sensors on separate motion capture devices while the user maintains the same orientation with respect to the image sensors.

Example 7 includes the subject matter of any of Examples 1-6, and further including generating a score indicative of a similarity between the movement of the user and the model movement pattern for display to the user.

Example 8 includes at least one non-transitory computer-readable storage medium including machine-readable instructions which, when executed, cause a machine to generate, for display to a user, a representation of the user performing a movement pattern of an activity from a first point of view; sense a deviation of movement of the user from a model movement pattern for the activity; select a second point of view based on a type of the deviation; and generate, for display to the user, a representation of the user performing the movement pattern for the activity from the second point of view.

Example 9 includes the subject matter of Example 8, the instructions, when executed, to cause the machine to provide, for display to the user, a representation of a trainer performing an example movement pattern of the activity from the first point of view; and provide, for display to the user, a representation of the trainer performing the example movement pattern of the activity from the second point of view responsive to sensing the deviation of the user from the model movement pattern.

Example 10 includes the subject matter of any of Examples 8-9, the instructions, when executed, to cause the machine to generate a guide skeleton to be overlaid on the representation of the user.

Example 11 includes the subject matter of any of Examples 8-10, the instructions, when executed, to cause the machine to change a color or brightness of a segment of the guide skeleton responsive to alignment of a body segment of the user with the segment of the guide skeleton.

Example 12 includes the subject matter of any of Examples 8-11, the instructions, when executed, to cause the machine to cause display of the guide skeleton responsive to a determination that the user is near a target position associated with the deviation.

Example 13 includes the subject matter of any of Examples 8-12, and wherein the representation of the user performing the movement pattern from the first point of view and the representation of the user performing the movement pattern from the second point of view is based on video data captured by image sensors on separate motion capture devices while the user maintains the same orientation with respect to the image sensors.

Example 14 includes the subject matter of any of Examples 8-13, the instructions, when executed, to cause the machine to generate a score indicative of a similarity between the movement of the user and the model movement pattern for display to the user.

Example 15 includes a system comprising a computing system comprising a memory to store information indicative of a model movement pattern for an activity; and at least one processor to generate, for display to a user, a representation of the user performing a movement pattern of the activity from a first point of view; sense a deviation of movement of the user from the model movement pattern for the activity; select a second point of view based on a type of the deviation; and generate, for display to the user, a representation of the user performing the movement pattern for the activity from the second point of view.

Example 16 includes the subject matter of Example 15, and further including a plurality of motion capture devices to capture positional data representing the movement of the user.

Example 17 includes the subject matter of any of Examples 15 and 16, and wherein the representation of the user performing the movement pattern from the first point of view and the representation of the user performing the movement pattern from the second point of view is based on video data captured by image sensors on the motion capture devices while the user maintains the same orientation with respect to the image sensors.

Example 18 includes the subject matter of any of Examples 15-17, and further including a display coupled to the computing system, the display to display the representation of the user from the first and second points of view.

Example 19 includes the subject matter of any of Examples 15-18, and wherein the computing system is to provide, for display to the user, a representation of a trainer performing an example movement pattern of the activity from the first point of view; and provide, for display to the user, a representation of the trainer performing the model movement pattern of the activity from the second point of view responsive to sensing the deviation of the user from the model movement pattern.

Example 20 includes the subject matter of any of Examples 15-19, and wherein the computing system is to generate a guide skeleton to be overlaid on the representation of the user.

Example 21 includes a method, comprising providing playback of one or more sets of three dimensional positional data of a subject performing an activity; detecting input from an editor respective to the playback of the one or more sets of three dimensional positional data; and storing parameters of the activity based on the detected input in an activity profile for use in movement based instruction.

Example 22 includes the subject matter of Example 21, and wherein the input from the editor respective to the playback comprises at least one capture of the subject, wherein each capture of the at least one capture is associated with a respective timepoint of the playback and at least one body part of the subject, wherein each capture is associated with a position of each body part of the associated at least one body part at the respective timepoint.

Example 23 includes the subject matter of any of Examples 21 and 22, and wherein the input from the editor respective to the playback comprises association of a first capture of the subject with a first phase of the activity and association of a second capture of the subject with a second phase of the activity.

Example 24 includes the subject matter of any of Examples 21-23, and further including detecting a selection by the editor of one or more body parts to be associated with a first capture of the at least one capture of the subject.

Example 25 includes the subject matter of any of Examples 21-24, and wherein the parameters comprise positions associated with the at least one capture of the subject.

Example 26 includes the subject matter of any of Examples 21-25, and further including using at least one position associated with the first capture and at least one position associated with the second capture to detect a repetition of the activity to update a counter.

Example 27 includes the subject matter of any of Examples 21-26, and further including using at least one position associated with the first capture and at least one position associated with the second capture to score a quality of a repetition of the activity.

Example 28 includes the subject matter of any of Examples 21-27, and wherein the input from the editor respective to the playback comprises weights specified by the editor for one or more body parts, the weights specifying a relative importance of the one or more body parts.

Example 29 includes the subject matter of any of Examples 21-28, and wherein the input from the editor respective to the playback comprises an association of the at least one capture to a scheme for detecting a mistake.

Example 30 includes the subject matter of any of Examples 21-29, and wherein the input from the editor respective to the playback comprises an association of the at least one capture to a scheme for correcting a mistake.

Example 31 includes the subject matter of any of Examples 21-30, and wherein the input from the editor respective to the playback includes an optimal point of view of the mistake.

Example 32 includes the subject matter of any of Examples 21-31, and further including storing, in the activity profile, at least one corrective prompt provided by the editor to be displayed responsive to detection of the mistake.

Example 33 includes an apparatus comprising memory to store one or more sets of three dimensional positional data of a subject performing an activity; and at least one processor comprising circuitry, the processor to provide playback of the one or more sets of three dimensional positional data of a subject performing an activity; detect input from an editor respective to the playback of the one or more sets of three dimensional positional data; and store parameters of the activity based on the detected input in an activity profile for use in movement based instruction.

Example 34 includes the subject matter of Example 33, and wherein the input from the editor respective to the playback comprises at least one capture of the subject, wherein each capture of the at least one capture is associated with a respective timepoint of the playback and at least one body part of the subject, wherein each capture is associated with a position of each body part of the associated at least one body part at the respective timepoint.

Example 35 includes the subject matter of any of Examples 33 and 34, and wherein the input from the editor respective to the playback comprises association of a first capture of the subject with a first phase of the activity and association of a second capture of the subject with a second phase of the activity.

Example 36 includes the subject matter of any of Examples 33-35, and wherein the input from the editor respective to the playback comprises an association of the at least one capture to a scheme for detecting a mistake.

Example 37 includes one or more non-transitory computer-readable media comprising instructions to cause an electronic device, upon execution of the instructions by one or more processors of the electronic device, to provide playback of one or more sets of three dimensional positional data of a subject performing an activity; detect input from an editor respective to the playback of the one or more sets of three dimensional positional data; and store parameters of the activity based on the detected input in an activity profile for use in movement based instruction.

Example 38 includes the subject matter of Example 37, and wherein the input from the editor respective to the playback comprises at least one capture of the subject, wherein each capture of the at least one capture is associated with a respective timepoint of the playback and at least one body part of the subject, wherein each capture is associated with a position of each body part of the associated at least one body part at the respective timepoint.

Example 39 includes the subject matter of any of Examples 37 and 38, and wherein the input from the editor respective to the playback comprises association of a first capture of the subject with a first phase of the activity and association of a second capture of the subject with a second phase of the activity.

Example 40 includes the subject matter of any of Examples 37-39, and wherein the input from the editor respective to the playback comprises an association of the at least one capture to a scheme for detecting a mistake.

Example 41 includes a method comprising utilizing at least one image sensor and at least one processor to measure a velocity of a body part of a user during an exercise performed by the user; and determining at least one of a number of repetitions or a load for the user for a set of a workout based at least in part on the measured velocity.

Example 42 includes the subject matter of Example 41, and wherein the velocity of the body part is measured during a first set of an exercise and the determination of at least one of the number of repetitions or the load is made for a second set of the exercise.

Example 43 includes the subject matter of any of Examples 41 and 42, and wherein the exercise is an exercise that does not use an external load.

Example 44 includes the subject matter of any of Examples 41-43, and further including determining at least one of repetitions or loads to be used for a plurality of different exercises of the workout based at least in part on the measured velocity.

Example 45 includes the subject matter of any of Examples 41-44, and wherein the body part is a joint of the user.

Example 46 includes the subject matter of any of Examples 41-45, and wherein the determination is further based on additional information about the user.

Example 47 includes the subject matter of any of Examples 41-46, and wherein the additional information about the user comprises at least one of a fitness goal of the user, a weight of the user, a second velocity measured during a previous set of the exercise, or one or more other velocities measured previously in the workout or a different workout for one or more different exercises, a measured or estimated one repetition maximum of the user, and an intensity preference selected the user.

Example 48 includes the subject matter of any of Examples 41-47, and wherein the determination is further based on measured velocities of body parts of other users during performance of the exercise.

Example 49 includes an apparatus comprising means to perform one or more elements of a method of any one of examples 41-48.

Example 50 includes one or more non-transitory computer-readable media comprising instructions to cause an electronic device, upon execution of the instructions by one or more processors of the electronic device, to perform one or more elements of a method of any one of examples 41-48.

Example 51 includes machine-readable storage including machine-readable instructions which, when executed, implement the method of any one of examples 41-48.

Example 52 includes an apparatus comprising one or more processors and one or more computer-readable media comprising instructions that, when executed by the one or more processors, cause the one or more processors to perform the method of any one of examples 41-48.

Example 53 includes a method comprising receiving, at a computing system, a feature set of a user, the computing system implementing a machine learning algorithm trained on feature sets of a plurality of users and corresponding workout feedback sets provided by a plurality of human advisors; and using the machine learning algorithm to generate a workout feedback set for the user feature set.

Example 54 includes the subject matter of Example 53, and wherein the feature set of the user comprises a fitness goal of the user.

Example 55 includes the subject matter of any of Examples 53 and 54, and wherein the feature set comprises at least one measured velocity of a body part of the user for at least one exercise.

Example 56 includes the subject matter of any of Examples 53-55, and wherein the feature set comprises information indicating how often the user is available to workout.

Example 57 includes the subject matter of any of Examples 53-56, and wherein the feature set comprises information indicating how often the user has worked out in the past.

Example 58 includes the subject matter of any of Examples 53-57, and wherein the feature set comprises information indicating physical attributes of the user.

Example 59 includes the subject matter of any of Examples 53-58, and wherein the feature set comprises information about a diet of the user.

Example 60 includes the subject matter of any of Examples 53-59, and wherein the workout feedback set comprises a workout schedule for the user to perform.

Example 61 includes the subject matter of any of Examples 53-60, and wherein the workout schedule specifies exercises to be performed by the user.

Example 62 includes the subject matter of any of Examples 53-61, and wherein the workout schedule specifies a number of sets and repetitions for the exercises.

Example 63 includes an apparatus comprising means to perform one or more elements of a method of any one of examples 53-62.

Example 64 includes one or more non-transitory computer-readable media comprising instructions to cause an electronic device, upon execution of the instructions by one or more processors of the electronic device, to perform one or more elements of a method of any one of examples 53-62.

Example 65 includes machine-readable storage including machine-readable instructions which, when executed, implement the method of any one of examples 53-62.

Example 66 includes an apparatus comprising one or more processors and one or more computer-readable media comprising instructions that, when executed by the one or more processors, cause the one or more processors to perform the method of any one of examples 53-62.

Example 67 includes a system comprising a motion capture system comprising at least one sensor to capture first three dimensional positional data of a subject performing an activity; a computing system to provide a playback of the first three dimensional positional data to an editor; receive input from the editor, the input comprising a definition of a mistake illustrated in the playback and an optimal point of view for the mistake; and request generation of an activity profile based on the first three dimensional positional data and the input from the editor; and a motion capture and feedback system comprising a display and at least one sensor to capture second three dimensional positional data of a user performing the activity, the motion capture and feedback system to provide movement based instruction to the user based on the second three dimensional positional data and the activity profile, wherein provision of the movement based instruction comprises displaying the user from the optimal point of view responsive to detecting the mistake.

Example 68 includes a method for generating a movement based instruction program based on three dimensional positional data, the method comprising using a plurality of first motion capture devices positioned at different poses relative to a subject to capture three dimensional positional data representing the subject performing an activity; providing a visual representation of the captured three dimensional positional data of the subject; creating an activity profile based on the three dimensional positional data and input received from an editor, the input comprising parameters associated with a correct movement pattern and at least one incorrect movement pattern for the activity; using a plurality of second motion capture devices positioned at different angles relative to a user to capture three dimensional positional data representing the user performing the activity; and generating feedback for the user based on the three dimensional positional data of the user and the activity profile, the feedback comprising an indication of a quality of movement of the user and a view of the user from an optimal point of view.

Example 69 includes the subject matter of Example 68, and wherein the three dimensional positional data comprises point clouds.

The invention claimed is:

1. A method, comprising:
providing playback of one or more sets of three dimensional positional data of a subject performing an activity;
detecting input from an editor respective to the playback of the one or more sets of three dimensional positional data, wherein the input from the editor respective to the playback comprises at least one capture of the subject, wherein each capture of the at least one capture is associated with a respective timepoint of the playback and at least one body part of the subject, wherein each capture is associated with a position of each body part of the associated at least one body part at the respective timepoint; and
storing parameters of the activity based on the detected input in an activity profile for use in movement based instruction.

2. The method of claim 1, wherein the input from the editor respective to the playback comprises association of a first capture of the subject with a first phase of the activity and association of a second capture of the subject with a second phase of the activity.

3. The method of claim 2, further comprising using at least one position associated with the first capture and at least one position associated with the second capture to detect a repetition of the activity to update a counter.

4. The method of claim 2, further comprising using at least one position associated with the first capture and at least one position associated with the second capture to score a quality of a repetition of the activity.

5. The method of claim 1, further comprising detecting a selection by the editor of one or more body parts to be associated with a first capture of the at least one capture of the subject.

6. The method of claim 1, wherein the parameters comprise positions associated with the at least one capture of the subject.

7. The method of claim 1, wherein the input from the editor respective to the playback comprises weights specified by the editor for one or more body parts, the weights specifying a relative importance of the one or more body parts.

8. The method of claim 1, wherein the input from the editor respective to the playback comprises an association of the at least one capture to a scheme for detecting a mistake.

9. The method of claim 8, wherein the input from the editor respective to the playback includes an optimal point of view of the mistake.

10. The method of claim 8, further comprising storing, in the activity profile, at least one corrective prompt provided by the editor to be displayed responsive to detection of the mistake.

11. The method of claim 1, wherein the input from the editor respective to the playback comprises an association of the at least one capture to a scheme for correcting a mistake.

12. An apparatus comprising:
    memory to store one or more sets of three dimensional positional data of a subject performing an activity; and
    at least one processor comprising circuitry, the processor to:
        provide playback of the one or more sets of three dimensional positional data of a subject performing an activity;
        detect input from an editor respective to the playback of the one or more sets of three dimensional positional data, wherein the input from the editor respective to the playback comprises at least one capture of the subject, wherein each capture of the at least one capture is associated with a respective timepoint of the playback and at least one body part of the subject, wherein each capture is associated with a position of each body part of the associated at least one body part at the respective timepoint; and
        store parameters of the activity based on the detected input in an activity profile for use in movement based instruction.

13. The apparatus of claim 12, wherein the input from the editor respective to the playback comprises association of a first capture of the subject with a first phase of the activity and association of a second capture of the subject with a second phase of the activity.

14. The apparatus of claim 12, wherein the input from the editor respective to the playback comprises an association of the at least one capture to a scheme for detecting a mistake.

15. One or more non-transitory computer-readable media comprising instructions to cause an electronic device, upon execution of the instructions by one or more processors of the electronic device, to:
    provide playback of one or more sets of three dimensional positional data of a subject performing an activity;
    detect input from an editor respective to the playback of the one or more sets of three dimensional positional data, wherein the input from the editor respective to the playback comprises at least one capture of the subject, wherein each capture of the at least one capture is associated with a respective timepoint of the playback and at least one body part of the subject, wherein each capture is associated with a position of each body part of the associated at least one body part at the respective timepoint; and
    store parameters of the activity based on the detected input in an activity profile for use in movement based instruction.

16. The media of claim 15, wherein the input from the editor respective to the playback comprises at least one capture of the subject, wherein each capture of the at least one capture is associated with a respective timepoint of the playback and at least one body part of the subject, wherein each capture is associated with a position of each body part of the associated at least one body part at the respective timepoint.

17. The media of claim 16, wherein the input from the editor respective to the playback comprises association of a first capture of the subject with a first phase of the activity and association of a second capture of the subject with a second phase of the activity.

18. The media of claim 16, wherein the input from the editor respective to the playback comprises an association of the at least one capture to a scheme for detecting a mistake.

19. A system comprising:
    a motion capture system comprising at least one sensor to capture first three dimensional positional data of a subject performing an activity;
    a computing system to:
        provide a playback of the first three dimensional positional data to an editor;
        receive input from the editor, the input comprising a definition of a mistake illustrated in the playback and an optimal point of view for the mistake, wherein the input further comprises at least one capture of the subject, wherein each capture of the at least one capture is associated with a respective timepoint of the playback and at least one body part of the subject, wherein each capture is associated with a position of each body part of the associated at least one body part at the respective timepoint; and
    request generation of an activity profile based on the first three dimensional positional data and the input from the editor; and
    a motion capture and feedback system comprising a display and at least one sensor to capture second three dimensional positional data of a user performing the activity, the motion capture and feedback system to provide movement based instruction to the user based on the second three dimensional positional data and the activity profile, wherein provision of the movement based instruction comprises displaying the user from the optimal point of view responsive to detecting the mistake.

* * * * *